US007960358B2

(12) United States Patent
Bhanot et al.

(10) Patent No.: US 7,960,358 B2
(45) Date of Patent: Jun. 14, 2011

(54) ANTISENSE MODULATION OF STEAROYL-COA DESATURASE EXPRESSION

(75) Inventors: Sanjay Bhanot, Carlsbad, CA (US); Kenneth W. Dobie, Del Mar, CA (US); John G. Geisler, Vista, CA (US); Mark J. Graham, San Clemente, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 510 days.

(21) Appl. No.: 11/613,144

(22) Filed: Dec. 19, 2006

(65) Prior Publication Data

US 2008/0153766 A1  Jun. 26, 2008

Related U.S. Application Data

(63) Continuation of application No. 10/619,253, filed on Jul. 15, 2003, now abandoned.

(51) Int. Cl.
*A61K 31/70* (2006.01)
*C07H 21/04* (2006.01)

(52) U.S. Cl. .......................................... 514/44; 536/24.5

(58) Field of Classification Search ........................ None
See application file for complete search history.

(56) References Cited

U.S. PATENT DOCUMENTS

| 5,741,666 | A | * | 4/1998 | Tartaglia | .................. 435/69.1 |
|---|---|---|---|---|---|
| 5,801,154 | A | | 9/1998 | Baracchini et al. | |
| 5,998,148 | A | | 12/1999 | Bennett et al. | |
| 6,030,837 | A | | 2/2000 | McKay et al. | |
| 6,077,672 | A | | 6/2000 | Monia et al. | |
| 6,261,840 | B1 | | 7/2001 | Cowsert et al. | |
| 6,355,635 | B1 | * | 3/2002 | Elliott et al. | ............... 514/231.5 |
| 6,582,908 | B2 | | 6/2003 | Fodor et al. | |
| 2001/0053519 | A1 | | 12/2001 | Fodor et al. | |
| 2002/0151018 | A1 | | 10/2002 | Prouty et al. | |
| 2003/0064950 | A1 | | 4/2003 | Ntambi et al. | |
| 2003/0083282 | A1 | | 5/2003 | Crooke et al. | |
| 2003/0157552 | A1 | * | 8/2003 | Hayden et al. | .................. 435/7.1 |
| 2003/0228597 | A1 | | 12/2003 | Cowsert et al. | |

FOREIGN PATENT DOCUMENTS

| EP | 238 198 A2 | 9/1987 |
|---|---|---|
| WO | WO 96/18736 | 6/1996 |
| WO | WO 99/63979 | 12/1999 |
| WO | WO 99/67378 | 12/1999 |
| WO | WO 00/09754 | 2/2000 |
| WO | WO 01/62954 | 8/2001 |
| WO | WO 03/012031 | 2/2003 |
| WO | WO 03/070885 | 8/2003 |
| WO | WO 2004/047746 | 6/2004 |
| WO | WO 2005014607 A2 * | 2/2005 |

OTHER PUBLICATIONS

Miyazaki et al. (2000) "The biosynthesis of hepatic cholesterol esters and triglycerides is impaired in mice with a disruption of the gene for stearoyl-CoA desaturase 1" J. Biol. Chem. 275:30132-138.*
Bennett et al. (1999) "Antisense oligonucleotides as a tool for gene functionalization and target validation" Biochimica Biophysica Acta 1489:19-30.*

Bakker et al. (2000) "Cytosolic triglycerides and oxidative stress in central obesity: the missing link between excessive atherosclerosis, endothelial dysfunction, and β-cell failure?" Atherosclerosis 148:17-21.*
Bhatti (2001) "Lipid profile in obesity" J. Ayub. Med. Coll. Abbottabad. Jan.-Mar.;13(1):31-3.*
Diot et al., "Stearoyl-CoA desaturase 1 coding sequences and antisense RNA affect lipid secretion in transfected chicken LMH hepatoma cells," *Archives Biochem. and Biophys.* 380(2):243-250 (2000).
Ahuja et al., "Differential Effects of Rexinoids and Thiazolidinediones on Metabolic Gene Expression in Diabetic Rodents," *Mol. Pharmacol.* (2001) 59:765-773.
Agrawal et al., "Antisense Therapeutics: is it simple as complementary base recognition?," *Molecular Medicine Today* (2000) 6:72-81.
Bene et al., "Cloning and Characterization of the Human Stearoyl-CoA Desaturase Gene Promotor: Transcriptional Activation by Sterol Regulartory Element Binding Protein and Repression by polyunsaturated Fatty Acids and Cholesterol," *Biochemistry and Biophysical Research Communications* (2001) 284:1194-1198.
Branch, A.D., "A good antisense molecule is hard to find," *TIBS* (1998) 45-50.
Diot et al., "Stearoyl-CoA Desaturase 1 Coding Sequences and Antisense RNA Affect Lipid Secretion in Transfected Chicken LMH Hepatoma Cells," *Archives of Biochemistry and Biophysics* (2000) 380(2):243-250.
Green et al., "Antisense Oligonucleotides: An Evolving Technology for the Modulation of Gene Expression in Human Disease," *Am. Coll. Surg.* (2000) 93-105.
Jen et al., "Suppression of Gene Expression by Targeted Disruption of Messenger RNA: Available Options and Current Strategies," *Stem Cells* (2000) 18(5): 307-319.
Jones et al., "Adipose tissue stearoyl-CoA desaturase mRNA is increased by obesity and decreased by polyunsaturated fatty acids," *Am. J. Physiol.* (1996) 271(1):E44-49.
Kim et al., "Differential regulation of the stearoyl-CoA desaturase genes by thiazolidinediones in 3T3-L1 adipocytes," *J. Lipid Res.* (2000) 41(8):1310-1316.
Li et al., "Partial Characterization of a cDNA for Human Stearoyl-CoA Desaturase and Changes in its mRNA Expression in Some Normal and Malignant Tissue," *Int. J. Cancer* (1994) 57:348-352.
Milner, N. et al., "Selecting effective antisense reagents on combinatorial oligonucleotide arrays," *Nature Biotechnology* (1997)15:537-541.
Ntambi, J.M., "The Regulation of Stearoyl-CoA Desaturase (SCD)," *Prog. Lipid Res.* (1995) 34(2):139-150.
Ntambi, J.M., "Regulation of stearoyl-CoA desaturase by polyunsaturated fatty acids and cholesterol," *J. Lipid Res.* (1999) 40:1549-1558.

(Continued)

*Primary Examiner* — Tracy Vivlemore
(74) *Attorney, Agent, or Firm* — Jones Day

(57) ABSTRACT

Antisense compounds, compositions and methods are provided for modulating the expression of stearoyl-CoA desaturase. The compositions comprise antisense compounds, particularly antisense oligonucleotides, targeted to nucleic acids encoding stearoyl-CoA desaturase. Methods of using these compounds for modulation of stearoyl-CoA desaturase expression and for treatment of diseases associated with expression of stearoyl-CoA desaturase are provided.

17 Claims, No Drawings

OTHER PUBLICATIONS

Opalinska, J., "Nucleic-Acid Therapeutics: Basic Principles and Recent Applications," *Nature Reviews Drug Discovery* (2002) 1:503-514.

Sessler et al., "Regulation of Stearoyl-C-A Desaturase 1 mRNA Stability by Polyunsaturated Fatty Acids in 3T3-L1 Adipocytes," *J. Biol. Chem* (1996) 271(947):29854-29858.

Taylor, M. et al., "Antisense Oligonucleotides: A Systematic High-Throughput Approach to Target Validation and Gene Function Determination," *DDT* (1999) 4(12):562-567.

Zhang et al., "Human stearoyl-CoA desaturase: alternative transcripts generated from a single gene by usage of tandem polyadenylation sites," *Biochem. J.* (1999) 340:255-264.

Zhang et al., "Isolation and characterization of the human stearoyl-CoA desaturase gene promoter: requirement of a conserved CCAAT cis-element," *Biochem. J.* (2001) 357:183-193.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

* cited by examiner

ANTISENSE MODULATION OF STEAROYL-CoA DESATURASE EXPRESSION

CROSS-REFERENCE TO RELATED APPLICATIONS

This application is a continuation of U.S. patent application Ser. No. 10/619,253, filed Jul. 15, 2003; which is a continuation-in-part of U.S. patent application Ser. No. 09/918,187, filed Jul. 30, 2001, now issued as U.S. Pat. No. 7,132,529.

INCORPORATION OF SEQUENCE LISTING

The present application is being filed along with a Sequence Listing in electronic format. The Sequence Listing is provided as a file entitled ISPH0590USC1SEQ.txt created Dec. 19, 2006, which is 122 Kb in size. The information in the electronic format of the sequence listing is incorporated herein by reference in its entirety.

BACKGROUND OF THE INVENTION

Saturated fatty acids are known to be the precursors of unsaturated fatty acids in higher organisms. However, the control mechanisms that govern the conversion of saturated fatty acids to unsaturated fatty acids are not well understood. The relative amounts of different fatty acids have effects on the physical properties of membranes. Furthermore, regulation of unsaturated fatty acids is important because they play a role in cellular activity, metabolism and nuclear events that govern gene transcription.

A critical committed step in the biosynthesis of monounsaturated fatty acids is the introduction of the first cis-double bond in the delta-9 position (between carbons 9 and 10). This oxidative reaction is catalyzed by stearoyl-CoA desaturase (SCD, also known as delta-9-desaturase) and involves cytochrome $b_5$, NADH (P)-cytochrome $b_5$ reductase and molecular oxygen (Ntambi, *J. Lipid Res.*, 1999, 40, 1549-1558). Although the insertion of the double bond occurs in several different methylene-interrupted fatty acyl-CoA substrates, the preferred substrates are palmitoyl- and stearoyl-CoA, which are converted to palmitoleoyl- and oleoyl-CoA respectively (Ntambi, J *Lipid Res.*, 1999, 40, 1549-1558).

It has been recognized that, regardless of diet, the major storage fatty acids in human adipose tissue are oleic acid, an 18 carbon unsaturated fatty acid, and palmitoleic acid, a 16 carbon unsaturated fatty acid (Ntambi, *J. Lipid Res.*, 1999, 40, 1549-1558). During the de novo synthesis of fatty acids, the fatty acid synthase enzyme stops at palmitoleic acid but the end product of the pathway is usually oleic acid (Ntambi, J *Lipid Res.*, 1999, 40, 1549-1558).

The stearoyl-CoA desaturase gene was partially characterized in 1994 via isolation of a 0.76 kb partial cDNA from human adipose tissue (Li et al., *Int. J. Cancer*, 1994, 57, 348-352). Increased levels of stearoyl-CoA desaturase mRNA were found in colonic and esophageal carcinomas and in hepatocellular carcinoma (Li et al., *Int. J. Cancer*, 1994, 57, 348-352). The gene was fully characterized in 1999 and it was found that alternative usage of polyadenylation sites generates two transcripts of 3.9 and 5.2 kb (Zhang et al., *Biochem. J.*, 1999, 340, 255-264). Two loci for the stearoyl-CoA desaturase gene were mapped to chromosomes 10 and 17 and it was determined that the chromosome 17 loci encodes a transcriptionally inactive pseudogene (Ntambi, *J. Lipid Res.*, 1999, 40, 1549-1558).

A nucleic acid molecule encoding the human stearoyl-CoA desaturase and a nucleic acid molecule, which under suitable conditions, specifically hybridizes to the nucleic acid molecule encoding the human stearoyl-CoA desaturase, have been described (Stenn et al., International patent publication WO 00/09754, 2000).

Stearoyl-CoA desaturase affects the ratio of stearate to oleate, which in turn, affects cell membrane fluidity. Alterations of this ratio have been implicated in various disease states including cardiovascular disease, obesity, non-insulin-dependent diabetes mellitus, skin disease, hypertension, neurological diseases, immune disorders and cancer (Ntambi, *J. Lipid Res.*, 1999, 40, 1549-1558). Stearoyl-CoA desaturase has been viewed as a lipogenic enzyme not only for its key role in the biosynthesis of monounsaturated fatty acids, but also for its pattern of regulation by diet and insulin (Ntambi, *J. Lipid Res.*, 1999, 40, 1549-1558).

The regulation of stearoyl-CoA desaturase is therefore of considerable physiologic importance and its activity is sensitive to dietary changes, hormonal imbalance, developmental processes, temperature changes, metals, alcohol, peroxisomal proliferators and phenolic compounds (Ntambi, J *Lipid Res.*, 1999, 40, 1549-1558).

Animal models have been very useful in investigations of the regulation of stearoyl-CoA by polyunsaturated fatty acids (PUFAs). For example, in adipose tissue of lean and obese Zucker rats, a 75% decrease in stearoyl-CoA desaturase mRNA was observed when both groups were fed a diet high in PUFAs relative to a control diet (Jones et al., *Am. J. Physiol.*, 1996, 271, E44-49).

Similar results have been obtained with tissue culture systems. In the murine 3T3-L1 adipocyte cell line, arachidonic linoleic, linolenic, and eicosapentanenoic acids decreased stearoyl-CoA desaturase expression in a dose-dependent manner (Sessler et al., *J. Biol. Chem.*, 1996, 271, 29854-29858).

The molecular mechanisms by which PUFAs regulate stearoyl-CoA desaturase gene expression in different tissues are still poorly understood. The current understanding of the regulatory mechanism involves binding of PUFAs to a putative PUFA-binding protein, after which repression transcription occurs via binding of the PUFA-binding protein to a cis-acting PUFA response element of the stearoyl-CoA desaturase gene (SREBP) (Ntambi, *J. Lipid Res.*, 1999, 40, 1549-1558; Zhang et al., *Biochem. J.*, 2001, 357, 183-193).

Cholesterol has also been identified as a regulator of stearoyl-CoA desaturase gene expression by a mechanism involving repression of the maturation of the sterol regulatory element binding protein (Bene et al., *Biochem. Biophys. Res. Commun.*, 2001, 284, 1194-1198; Ntambi, *J. Lipid Res.*, 1999, 40, 1549-1558).

Thiazolidinediones have been employed as regulators of stearoyl-CoA desaturase activity in murine 3T3-L1 adipocytes (Kim et al., *J. Lipid Res.*, 2000, 41, 1310-1316), and in diabetic rodents (Singh Ahuja et al., *Mol. Pharmacol.*, 2001, 59, 765-773).

Compositions comprising a saponin in an amount effective to inhibit stearoyl-CoA desaturase enzyme activity were described. The saponin was derived from a source selected from the group consisting of *Quillaja saponaria, Panax trifolium, Panax quinquefolium* and *Glycyrrhiza glabra* (Chavali and Forse, International patent publication No. WO 99/63979 1999).

An inhibitor of stearoyl-CoA desaturase was prepared in a form suitable for oral, parenteral, rectal or dermal administration for use in modifying the lipid structure of cell membranes. The inhibitor was described as consisting of a saturated fatty acid having from 12 to 28 carbon atoms in the alkyl chain, e.g. stearic acid, or a pharmaceutically acceptable derivative thereof prepared in a form suitable for parenteral, rectal or dermal administration (Wood et al., European Patent No. EP 238198 1987). A stearoyl-CoA desaturase antisense vector has been used to reduce expression levels of stearoyl-CoA desaturase in chicken LMH hepatoma cells (Diot et al., *Arch. Biochem. Biophys.*, 2000, 380, 243-250).

To date, investigative strategies aimed at inhibiting stearoyl-CoA desaturase function include the previously cited uses of polyunsaturated fatty acids, saturated fatty acids, thiazolidinediones, cholesterol, and an antisense vector. However, these strategies are untested as therapeutic protocols. Consequently, there remains a long felt need for additional agents capable of effectively inhibiting stearoyl-CoA desaturase.

SUMMARY OF THE INVENTION

The present invention provides compositions and methods for modulating the expression of stearoyl-CoA desaturase. Such compositions and methods are shown to modulate the expression of stearoyl-CoA desaturase, including inhibition of both isoforms of stearoyl-CoA desaturase.

In particular, this invention relates to compounds, particularly oligonucleotides, specifically hybridizable with nucleic acids encoding stearoyl-CoA desaturase. Such compounds, particularly antisense oligonucleotides, are targeted to a nucleic acid encoding stearoyl-CoA desaturase, and modulate the expression of stearoyl-CoA desaturase. Pharmaceutical and other compositions comprising the compounds of the invention are also provided.

Further provided are methods of modulating the expression of stearoyl-CoA desaturase in cells or tissues comprising contacting the cells or tissues with one or more of the antisense compounds or compositions of the invention. Further provided are methods of treating an animal, particularly a human, suspected of having or being prone to a disease or condition associated with expression of stearoyl-CoA desaturase, by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding stearoyl-CoA desaturase, ultimately modulating the amount of stearoyl-CoA desaturase produced. This is accomplished by providing antisense compounds that specifically hybridize with one or more nucleic acids encoding stearoyl-CoA desaturase.

Antisense technology is emerging as an effective means of reducing the expression of specific gene products and is uniquely useful in a number of therapeutic, diagnostic and research applications involving modulation of stearoyl-CoA desaturase expression.

As used herein, the terms "target nucleic acid" and "nucleic acid encoding stearoyl-CoA desaturase" encompass DNA encoding stearoyl-CoA desaturase, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds that specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of stearoyl-CoA desaturase. In the context of the present invention, "modulation" means either an increase (stimulation) or a decrease (inhibition) in the expression of a gene. In one embodiment of the present invention, inhibition is a preferred form of modulation of gene expression and MRNA is a preferred target.

For example, in one embodiment of the present invention, the compounds of the present invention inhibit expression of stearoyl-CoA desaturaseby at least 10% as measured in a suitable assay, such as those described in the examples below. In another embodiment, the compounds of the present invention inhibit expression of stearoyl-CoA desaturase by at least 25%. In still another embodiment of the invention, the compounds of the present invention inhibit expression of stearoyl-CoA desaturase by at least 40%. In yet a further embodiment of this invention, the compounds of the present invention inhibit expression of stearoyl-CoA desaturase by at least 50%. In a further embodiment of this invention, the compounds of the present invention inhibit expression of stearoyl-CoA desaturase by at least 60%. In another embodiment of this invention, the compounds of the present invention inhibit expression of stearoyl-CoA desaturase by at least 70%. In still another embodiment of this invention, the compounds of this invention inhibit expression of stearoyl-CoA desaturase by at least 80%. In another embodiment of this invention, the compounds of this invention inhibit expression of stearoyl-CoA desaturase by at least 90% or higher. Exemplary compounds are illustrated in Examples 15, and 17 to 24 below.

It is preferred to target specific nucleic acids for antisense. "Targeting" an antisense compound to a particular nucleic acid, in the context of this invention, is a multistep process. The process as described herein begins with the identification of a nucleic acid sequence encoding stearoyl-CoA desaturase. This may be, for example, a cellular gene (or mRNA transcribed from the gene). The targeting process also includes determination of a site or sites within this gene for the antisense interaction to occur such that the desired effect, e.g., detection or modulation of expression of the protein, results. In one embodiment of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an MRNA molecule transcribed from a gene encoding stearoyl-CoA desaturase, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is another embodiment of a region of the nucleic acid sequence encoding stearoyl-CoA desaturase which may be targeted effectively. Other target regions of this invention include the 5' untranslated region (5'UTR) of the nucleic acid sequence encoding stearoyl-CoA desaturase, known in the art to refer to the portion of an mRNA in the 5' direction from the translation initiation codon, and thus including nucleotides between the 5' cap site and the translation initiation codon of an mRNA or corresponding nucleotides on the gene. Still another target region is the 3' untranslated region (3'UTR) of the nucleic acid sequence encoding stearoyl-CoA desaturase, known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region of the nucleic acid sequence encoding stearoyl-CoA desaturase may also be a preferred target region.

Although some eukaryotic mRNA transcripts are directly translated, many contain one or more regions, known as "introns," which are excised from a transcript before it is translated. The remaining (and therefore translated) regions are known as "texons" and are spliced together to form a continuous MRNA sequence. mRNA splice sites, i.e., intron-exon junctions, of the nucleic acid sequence encoding stearoyl-CoA desaturase may also be preferred target regions, and are particularly useful in situations where aberrant splicing is implicated in disease, or where an overproduction of a particular niRNA splice product is implicated in disease. Aberrant fusion junctions of the nucleic acid sequence encoding stearoyl-CoA desaturase, due to rearrangements or deletions, are also preferred targets. In another embodiment of this invention, introns of the nucleic acid sequence encoding stearoyl-CoA desaturase can also be effective target regions for antisense compounds targeted, for example, to DNA or pre-mRNA of the nucleic acid sequence encoding stearoyl-CoA desaturase.

Once one or more target sites have been identified, oligonucleotides are chosen which are sufficiently complementary to the target, i.e., hybridize sufficiently well and with sufficient specificity, to give the desired effect. See, e.g., Tables 1-5 below.

For example, Tables 1 and 2 illustrate antisense oligonucleotides that hybridize to target regions of nucleotide 9 to 5100 of the nucleotide sequence of human stearoyl CoA desaturase SEQ ID NO: 3. In one embodiment, for example, desirable oligonucleotides target regions within nucleotides 13 to 71. In another example, desirable oligonucleotides target regions within nucleotides 178 to 247. In another example, desirable oligonucleotides target regions within nucleotides 482 to 843. In another example, desirable oligonucleotides target regions within nucleotides 892 to 1064. In another example, desirable oligonucleotides target regions within nucleotides 1303-1502. In another example, desirable oligonucleotides target regions within nucleotides 1597-2233. In another example, desirable oligonucleotides target regions within nucleotides 2245-2589. In another example, desirable oligonucleotides target regions within nucleotides 2676-3278. In another example, desirable oligonucleotides target regions within nucleotides 3342-3499. In another example, desirable oligonucleotides target regions within nucleotides 3655-3674. In another example, desirable oligonucleotides target regions within nucleotides 3707-3790. In another example, desirable oligonucleotides target regions within nucleotides 3825-3853. In another example, desirable oligonucleotides target regions within nucleotides 3911-4072. In another example, desirable oligonucleotides target regions within nucleotides 4132-4224. In another example, desirable oligonucleotides target regions within nucleotides 4261-4398. In another example, desirable oligonucleotides target regions within nucleotides 4420-4554. In another example, desirable oligonucleotides target regions within nucleotides 4645-4677. In another example, desirable oligonucleotides target regions within nucleotides 4834-4865. In another example, desirable oligonucleotides target regions within nucleotides 4892-5100. Oligonucletides that target any nucleotide sequence within SEQ ID NO: 3, with the explicit exclusion of target regions between nucleotides 70-91, 242-262 and 860-882, are included within this invention.

As another example, Table 2 indicates illustrative oligonucleotides that hybridize to target regions found within nucleotides 505 to 14020 of the nucleotide sequence of human stearoyl CoA desaturase SEQ ID NO: 81.

Tables 3-5 illustrate oligonucleotides that bind to target regions within nucleotides 1 to 5366 of the nucleotide sequence of mouse stearoyl CoA desaturase SEQ ID NO: 222. In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the target nucleic acid sequence (DNA or RNA) encoding stearoyl-CoA desaturase.

It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility of the stearoyl-CoA desaturase enzyme. There also must be a sufficient degree of complementarity to avoid non-specific binding of the antisense compound to non-stearoyl-CoA desaturase target sequences under conditions in which specific binding is desired. Such conditions include physiological conditions in the case of in vivo assays or therapeutic treatment, and in the case of in vitro assays, include conditions in which the assays are performed.

For example, in one embodiment, the antisense compounds of the present invention comprise at least 80% sequence complementarity to a target region within the target nucleic acid of stearoyl-CoA desaturase to which they are targeted. In another embodiment, the antisense compounds of the present invention comprise at least 90% sequence complementarity to a target region within the target nucleic acid of stearoyl-CoA desaturase to which they are targeted. In still another embodiment of this invention, the antisense compounds of the present invention comprise at least 95% sequence complementarity to a target region within the target nucleic acid sequence of stearoyl-CoA desaturase to which they are targeted. For example, an antisense compound in which 18 of 20 nucleobases of the antisense compound are complementary, and would therefore specifically hybridize, to a target region would represent 90 percent complementarity. Percent complementarity of an antisense compound with a region of a target nucleic acid can be determined routinely using basic local alignment search tools (BLAST programs) (Altschul et al., *J. Mol. Biol.,* 1990, 215, 403-410; Zhang and Madden, *Genome Res.,* 1997, 7, 649-656).

Antisense and other compounds of the invention that hybridize to the target and inhibit expression of stearoyl-CoA desaturase are identified as taught herein. In one embodiment of this invention, the sequences of these compounds are hereinbelow identified as preferred embodiments of the invention (see, e.g., Tables 1-5). The target sites to which these preferred sequences are complementary are hereinbelow referred to as "active sites" and are therefore preferred sites for targeting (see, e.g., Tables 1-5). Therefore another embodiment of the invention encompasses compounds that hybridize to these active sites.

In one embodiment of this invention, the term "illustrative target region" is defined as a nucleobase sequence of a target region of stearoyl-CoA desaturase, to which an active antisense compound is targeted. For example, an illustrative target region may be at least 8 or at least 15 nucleobases in length. In still another embodiment an illustrative target region is at least 25 nucleobases of the nucleic acid sequence or molecule encoding stearoyl-CoA desaturase, to which an active antisense compound is targeted. In still another embodiment an illustrative target region is at 35 nucleobases. In yet another embodiment an illustrative target region is at least 50 nucleobases of the nucleic acid sequence or molecule encoding stearoyl-CoA desaturase, to which an active antisense compound is targeted. In still another embodiment an illustrative target region is at least 70 nucleobases. In another embodiment an illustrative target region is at least 80 nucleobases or more. In still another embodiments, the illustrative target regions consist of consecutive nucleobases of the lengths identified above.

Exemplary additional target regions include DNA or RNA sequences that comprise at least the 8 consecutive nucleobases from the 5'-terminus of one of the illustrative target regions (the remaining nucleobases being a consecutive stretch of the same DNA or RNA beginning immediately upstream of the 5'-terminus of the target region and continuing until the DNA or RNA contains about 8 to about 80 nucleobases). Similarly additional target regions are represented by DNA or RNA sequences that comprise at least the 8 consecutive nucleobases from the 3'-terminus of one of the illustrative target regions (the remaining nucleobases being a consecutive stretch of the same DNA or RNA beginning immediately downstream of the 3'-terminus of the target region and continuing until the DNA or RNA contains about 8 to about 80 nucleobases).

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J Cancer,* 1999, 35, 1895-904) and mass spectrometry methods (reviewed in (To, *Comb. Chem. High Throughput Screen,* 2000, 3, 235-41).

The specificity and sensitivity of antisense is also harnessed by those of skill in the art for therapeutic uses. Antisense oligonucleotides have been employed as therapeutic moieties in the treatment of disease states in animals, particularly mammals, and including man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. Antisense compounds include ribozymes, external guide sequence (EGS) oligonucleotides (oligozymes), and other short catalytic RNAs or catalytic oligonucleotides that hybridize to the target nucleic acid encoding stearoyl-CoA desaturase and modulate expression of that enzyme.

The antisense compounds in accordance with this invention preferably comprise from at least 8 nucleobases (i.e. about 8 linked nucleosides). Particularly preferred antisense compounds are antisense oligonucleotides. In one embodiment, antisense compounds of this invention are antisense oligonucleotides of at least about 15 nucleobases in length. In another embodiment, antisense compounds of this invention comprise about 25 nucleobases in length. In still another embodiment, antisense compounds of this invention comprise about 35 nucleobases in length. In yet another embodiment, antisense compounds of this invention comprise about 40 nucleobases in length. In still another embodiment, antisense compounds of this invention comprise about 50 nucleobases in length. In another embodiment, antisense compounds of this invention comprise about 60 nucleobases in length. In still another embodiment, antisense compounds of this invention comprise about 70 nucleobases in length. In yet another embodiment, antisense compounds of this invention comprise about 80 nucleobases in length.

In other embodiments, exemplary antisense compounds include DNA or RNA sequences that comprise at least the 8 consecutive nucleobases from the 5'-terminus of one of the illustrative antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly, in another embodiment, such antisense compounds include at least 12 consecutive nucleobases from the 5'-terminus of one of the illustrative antisense compounds. In yet another embodiment, the antisense compound includes at least 25 consecutive nucleobases from the 5'-terminus of one of the illustrative antisense compounds. In a further embodiment, the antisense compound includes at least 30 consecutive nucleobases from the 5'-terminus of one of the illustrative antisense compounds. In yet another embodiment, the antisense compound includes at least 50 consecutive nucleobases from the 5'-terminus of one of the illustrative antisense compounds. In still another embodiment, the antisense compound includes at least 60 or more consecutive nucleobases from the 5'-terminus of one of the illustrative antisense compounds.

Similarly in another embodiment antisense compounds are represented by DNA or RNA sequences that comprise at least the 8 consecutive nucleobases from the 3'-terminus of one of the illustrative antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). In another embodiment, such antisense compounds include at least 12 consecutive nucleobases from the 3'-terminus of one of the illustrative antisense compounds. In yet another embodiment, the antisense compound includes at least 25 consecutive nucleobases from the 3'-terminus of one of the illustrative antisense compounds. In a further embodiment, the antisense compound includes at least 30 consecutive nucleobases from the 3'-terminus of one of the illustrative antisense compounds. In yet another embodiment, the antisense compound includes at least 50 consecutive nucleobases from the 3'-terminus of one of the illustrative antisense compounds. In still another embodiment, the antisense compound includes at least 60 or more consecutive nucleobases from the 3'-terminus of one of the illustrative antisense compounds. One having skill in the art, once armed with the antisense compounds illustrated, and other teachings herein will be able, without undue experimentation, to identify further antisense compounds of this invention.

Specific sequences of particular exemplary target regions of stearoyl-CoA desaturase and representative antisense and other compounds of the invention, which hybridize to the target, and inhibit expression of the target, are identified below are set forth below in Tables 1-5. One of skill in the art will recognize that these serve to illustrate and describe particular embodiments within the scope of the present invention. Once armed with the teachings of the illustrative target regions described herein may without undue experimentation identify further target regions, as described above. In addition, one having ordinary skill in the art using the teachings contained herein will also be able to identify additional compounds, including oligonucleotide probes and primers, that specifically hybridize to these illustrative target regions using techniques available to the ordinary practitioner in the art.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage, i.e. a single inverted nucleoside residue that may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 30 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240.

Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylamino-ethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in International patent publication Nos. WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thyrnine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Another modification of the oligonucleotides of the invention involves chemically linking to the oligonucleotide one or more moieties or conjugates that enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharnacokinetic properties, in the context of this invention, include groups that improve oligomer uptake, distribution, metabolism or excretion. Representative conjugate groups are disclosed in International Patent Publication No. WO93/07883 (Application PCT/US92/09196, filed Oct. 23, 1992) the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. NY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in International Patent Publication Nos. WO 93/24510 to Gosselin et al., published Dec. 9, 1993 or WO 94/26764, and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylene-diamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1-19). The base addition salts of the acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder that can be treated by modulating the expression of stearoyl-CoA desaturase is treated by administering antisense compounds in accordance with this invention. Among such diseases or disorder are included, for example, cardiovascular disease, obesity, non-insulin-dependent diabetes mellitus, skin disease, hypertension, neurological diseases, immune disorders and cancer.

The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically to prevent such diseases or disorders, e.g., to prevent or delay infection, undue weight gain, inflammation or tumor formation, for example.

The antisense compounds of the invention are useful for research and diagnostics, because these compounds hybridize to nucleic acids encoding stearoyl-CoA desaturase, enabling sandwich and other assays to easily be constructed to exploit this fact. Hybridization of the antisense oligonucleotides of the invention with a nucleic acid encoding stearoyl-CoA desaturase can be detected by means known in the art. Such means may include conjugation of an enzyme to the oligonucleotide, radiolabelling of the oligonucleotide or any other suitable detection means. Kits using such detection means for detecting the level of stearoyl-CoA desaturase in a sample may also be prepared.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315, 298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers, surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyomithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. Published Patent Application No. 2003/0040497 (Feb. 27, 2003) and its parent applications; U.S. Published Patent Application No. 2003/0027780 (Feb. 6, 2003) and its parent applications; and U.S. patent application Ser. No. 09/082,624 (filed May 21, 1998), each of which is incorporated herein by reference in their entirety.

Compositions and formulations for parenteral, intrathecal or intraventricular administration may include sterile aqueous solutions, which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug, which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, cited above).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, cited above). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, cited above).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, cited above).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture has been reviewed in the literature (Idson, cited above). Emulsion formulations for oral delivery have been very widely used because of reasons of ease of formulation, efficacy from an absorption and bioavailability standpoint (Rosoff, cited above; Idson, cited above). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile, which is a single optically isotropic and thermodynamically stable liquid solution (Rosoff, cited above). Typically microemulsions are systems that are prepared by first dispersing an oil in an aqueous surfactant solution and then adding a sufficient amount of a fourth component; generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, cited above; Block, cited above). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., 1994 cited above; Ho et al., *J. Pharm. Sci.*, 1996, 85, 138-143). Often microemulsions may form spontaneously when their components are brought together at ambient temperature. This may be particularly advantageous when formulating thermo-labile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastro-intestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome that is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, cited above). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. *Commun.*, 1987, 147, 980-985).

Liposomes that are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410).

Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes. This latter term, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N. Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and International Patent Publication No. WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in International Patent Publication No. WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and International Patent Publication No. WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in International Patent Publication No. WO 91/05545 and U.S. Pat. No. 5,225,212 (both to Martin et al.) and in International Patent Publication No. WO 94/20073 (Zalipsky et al.) Liposomes comprising PEG-modified ceramide lipids are described in International Patent Publication No. WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. International Patent Publication No. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. International Patent Publication No. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets that are so highly deformable that they are easily able to penetrate through pores that are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, cited above).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, cited above).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., 1991, cited above); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., 1991, p. 92, cited above; Muranishi, *Critical Reviews in Therapeutic Drug Carrier Systems*, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The *Pharmacological Basis of Therapeutics*, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., 1991, page 92, cited above; Swinyard, Chapter 39 *In: Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1-33; Yamamoto et al., *J. Pharm. Exp. Ther.*, 1992, 263, 25; Yamashita et al., *J. Pharm. Sci.*, 1990, 79, 579-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315-339). Chelating agents of the invention include but are not limited to disodium ethylenediamine tetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., 1991, page 92, cited above; Muranishi, 1990, cited above; Buur et al., *J. Control Rel.*, 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, 1990, cited above). This class of penetration enhancers include, for example, unsaturated cyclic ureas, 1-alkyl- and 1-alkenylazacyclo-alkanone derivatives (Lee et al., 1991, page 92, cited above); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., International Patent Publication No. WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activityper se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115-121; Takakura et al., *Antisense & Nucl. Acid Drug Dev.,* 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration that do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration that do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances that increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The *Merck Manual of Diagnosis and Therapy,* 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The *Merck Manual of Diagnosis and Therapy,* 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research*, 1993, 21, 3197-3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2, 2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486-504.

2,2'-Anhydro [1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5α-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (790 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(iso-propyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites 2'-(Dimethylaniinooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 =eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-0-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O—[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoram (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2$^1$-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee et al., International Patent Publication No. WO 94/02501). Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published International Patent Publication Nos. WO 94/17093 and WO 94/02499, herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)]Chimeric Phosphorothioate Oligonucleotides

[2'-O-(2-methoxyethyl)]—[2'-deoxy]—[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl)Phosphodiester]Chimeric Oligonucleotides

[2'-O-(2-methoxyethyl phosphodiester]—[2'-deoxy phosphorothioate]—[2'-O-(methoxyethyl)phosphodiester]chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full-length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The fill-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multichannel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following seven cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HepG2 Cells:

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

AML12 Cells:

AML12 (alpha mouse liver 12) cell line was established from hepatocytes from a mouse (CD1 strain, line MT42) transgenic for human TGF alpha. Cells are cultured in a 1:1 mixture of Dulbecco's modified Eagle's medium and Ham's F12 medium with 0.005 mg/ml insulin, 0.005 mg/ml transferrin, 5 ng/ml selenium, and 40 ng/ml dexamethasone, and 90%; 10% fetal bovine serum. For subculturing, spent medium is removed; and fresh media of 0.25% trypsin, 0.03% EDTA solution is added. Fresh trypsin solution (1 to 2 ml) is added and the culture is left to sit at room temperature until the cells detach.

Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

Primary Mouse Hepatocytes:

Primary mouse hepatocytes were prepared from CD-1 mice purchased from Charles River Labs (Wilmington, Mass.) and were routinely cultured in Hepatoyte Attachment Media (Gibco) supplemented with 10% Fetal Bovine Serum (Gibco/Life Technologies, Gaithersburg, Md.), 250 nM dexamethasone (Sigma), and 10 nM bovine insulin (Sigma). Cells were seeded into 96-well plates (Falcon-Primaria #3872) at a density of 10000 cells/well for use in RT-PCR analysis.

For Northern blotting or other analyses, cells are plated onto 100 mm or other standard tissue culture plates coated with rat tail collagen (200 µg/ mL) (Becton Dickinson) and treated similarly using appropriate volumes of medium and oligonucleotide.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 medium containing 3.75 µg/mL LIPOFECTIN™ reagent (Gibco BRL) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Stearoyl-CoA Desaturase Expression

Antisense modulation of stearoyl-CoA desaturase expression can be assayed in a variety of ways known in the art. For example, stearoyl-CoA desaturase mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of stearoyl-CoA desaturase can be quantitated in a variety of ways well known in the art, such as immunoprecipitation, Western blot analysis (immunoblotting), ELISA or fluorescence-activated cell sorting (FACS). Antibodies directed to stearoyl-CoA desaturase can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758-1764. Other methods for poly (A)+ mRNA isolation are taught in, for example, Ausubel, F. M. et al., *Current Protocols in Molecular Biology*, Volume 1, pp. 4.5.1-4.5.3, John Wiley & Sons, Inc., 1993. Briefly, for cells grown on 96-well plates, growth medium was removed from the cells and each well was washed with 200 µL cold PBS, 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Stearoyl-CoA Desaturase mRNA Levels

Quantitation of stearoyl-CoA desaturase mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the 10 PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™ reagent, and 12.5 Units MuLV reV rse transcriptase) to 96 well plates containing 25 µL total RNA solution. The RT reaction was carried out by incubation for 30 minutes at 48° C. Following a 10 minute incubation at 95° C. to activate the AMPLITAQ GOLD™ reagent, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ reagent (Molecular Probes, Inc. Eugene, Oreg.). GAPDH expression is quantified by real time RT-PCR, by being run simultaneously with the target, multiplexing, or separately. Total RNA is quantified using RiboGreenTm RNA quantification reagent from Molecular Probes. Methods of RNA quantification by RiboGreen™ reagent are taught in Jones, L. J., et al, *Analytical Biochemistry*, 1998, 265, 368-374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human stearoyl-CoA desaturase were designed to hybridize to a human stearoyl-CoA desaturase sequence, using published sequence information (GenBank accession number AF097514, incorporated herein as SEQ ID NO: 3). For human stearoyl-CoA desaturase the PCR primers were:
forward primer: GATCCCGGCATCCGAGA (SEQ ID NO: 4)
reverse primer: GGTATAGGAGCTAGAGATATCGTCCTG (SEQ ID NO: 5) and the PCR
probe was: FAM-CCAAGATGCCGGCCCACTTGC-TAMRA
(SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:
forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTC-CCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Stearoyl-CoA Desaturase mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 apparatus (Stratagene, Inc, La Jolla, Calif.) and then robed using QUICKHYB™ hybridization solution (Stratagene, La Jolla, Calif.) using manufacturer's recommendations for stringent conditions.

To detect human stearoyl-CoA desaturase, a human stearoyl-CoA desaturase specific probe was prepared by PCR using the forward primer GATCCCGGCATCCGAGA (SEQ ID NO: 4) and the reverse primer GGTATAGGAGCTA-GAGATATCGTCCTG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ apparatus and IMAGEQUANT™ Software V3.3 (Molecular Dynamics, Sunnyvale, Calif.). Data was normalized to GAPDH levels in untreated controls.

Example 15

Antisense Inhibition of Human Stearoyl-CoA Desaturase Expression by Chimeric Phosphorothioate Oligonucleotides having 2'-MOE Wings and a Deoxy Gap In accordance with the present invention, a series of oligonucleotides was designed to target different regions of the human stearoyl-CoA desaturase RNA, using published sequence (GenBank accession number AF097514, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human stearoyl-CoA desaturase mRNA levels in HepG2 cells by quantitative real-time PCR as described in other examples herein. Data are averages from two experiments. If present, "N.D." indicates "no data".

TABLE 1

Inhibition of human stearoyl-CoA desaturase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147899 | 5'UTR | 3 | 9 | GTCCGGTATTTCCTCAGCCC | N.D. | 10 |
| 147900 | 5'UTR | 3 | 72 | CCGCGGTGCGTGGAGGTCCC | N.D. | 11 |
| 147901 | 5'UTR | 3 | 121 | TACGCGCTGAGCCGCGGCGC | N.D. | 12 |
| 147902 | 5'UTR | 3 | 141 | GCGGTTTCGAAGCCCGCCGG | N.D. | 13 |
| 147903 | Coding | 3 | 311 | CCTCCATTCTGCAGGACCCT | N.D. | 14 |
| 147904 | Coding | 3 | 471 | TCCCAAGTGTAGCAGAGACA | N.D. | 15 |
| 147905 | Coding | 3 | 571 | CTCCTGCTGTTATGCCCAGG | N.D. | 16 |
| 147906 | Coding | 3 | 691 | CACGGTGGTCACGAGCCCAT | N.D. | 17 |
| 147907 | Coding | 3 | 771 | CAGCCAACCCACGTGAGAGA | 22 | 18 |
| 147908 | Coding | 3 | 824 | GACAAGTCTAGCGTACTCCC | 49 | 19 |
| 147909 | Coding | 3 | 1011 | GTTCACCAGCCAGGTGGCAT | 10 | 20 |
| 147910 | Coding | 3 | 1111 | TGTGGAAGCCCTCACCCACA | 0 | 21 |
| 147911 | Coding | 3 | 1171 | AGTTGATGTGCCAGCGGTAC | 6 | 22 |
| 147912 | Stop Codon | 3 | 1307 | GGACCCCAAACTCAGCCACT | 25 | 23 |
| 147913 | 3'UTR | 3 | 1581 | TGCCTGGGAGGCAATAAGGG | 8 | 24 |
| 147914 | 3'UTR | 3 | 1861 | ATACATGCTAACTCTCTCCC | 10 | 25 |
| 147915 | 3'UTR | 3 | 1941 | AAGTCCTCATTAGGTAGGCA | 37 | 26 |
| 147916 | 3'UTR | 3 | 2241 | TGTAATGAGCAGCTCATGGA | 0 | 27 |
| 147917 | 3'UTR | 3 | 2616 | TCAGTAACCTTCTCAAGCCC | 0 | 28 |
| 147918 | 3'UTR | 3 | 2980 | GGAGCTGCCTGGACAGCAAG | 16 | 29 |
| 147919 | 3'UTR | 3 | 3011 | TCAGTGACCCTGAGCATTCT | 30 | 30 |
| 147920 | 3'UTR | 3 | 3231 | TGGCTGGCCCACTGGCTCAA | 11 | 31 |
| 147921 | 3'UTR | 3 | 3291 | GCATGCCCTCTGGTTCTGAC | 7 | 32 |
| 147922 | 3'UTR | 3 | 3471 | GCTTTGCAGTTCACCCTGAC | 23 | 33 |
| 147923 | 3'UTR | 3 | 3502 | GTGGTATCTCAAATCCCAGG | 0 | 34 |
| 147924 | 3'UTR | 3 | 3791 | TAGTCCAGGCTAACCCCTGT | 0 | 35 |
| 147925 | 3'UTR | 3 | 3851 | GTGATCTTCCCTTAGATCCT | 0 | 36 |
| 147926 | 3'UTR | 3 | 4101 | CTCAGCAGACACACTCCCAC | 3 | 37 |
| 147927 | 3'UTR | 3 | 4226 | GCTAAGTTGTCAGCACACCC | 0 | 38 |
| 147928 | 3'UTR | 3 | 4406 | AAGTTTCCAGAATGAAGCCC | 25 | 39 |

TABLE 1-continued

Inhibition of human stearoyl-CoA desaturase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147929 | 3'UTR | 3 | 4571 | AGAGAATACACCCAAGATAC | 0 | 40 |
| 147930 | 3'UTR | 3 | 4708 | TAGTTAAGTGACTTGCCCAG | 0 | 41 |
| 147931 | 3'UTR | 3 | 4771 | GCCCTTTGAGGTAGGTCAGT | 4 | 42 |
| 147932 | 3'UTR | 3 | 4921 | CCATATAGACTAATGACAGC | 10 | 43 |
| 147933 | 3'UTR | 3 | 5021 | CTGTATGTTTCCGTGGCAAT | 11 | 44 |
| 168231 | 5'UTR | 3 | 101 | CTTGCACGCTAGCTGGTTGT | N.D. | 45 |
| 168232 | Coding | 3 | 331 | GCATCGTCTCCAACTTATCT | N.D. | 46 |
| 168233 | Coding | 3 | 451 | TAAGGATGATGTTTCTCCAG | N.D. | 47 |
| 168234 | Coding | 3 | 526 | CCCAAAGCCAGGTGTAGAAC | N.D. | 48 |
| 168235 | Coding | 3 | 601 | TGTAAGAGCGGTGGCTCCAC | N.D. | 49 |
| 168236 | Coding | 3 | 661 | CATTCTGGAATGCCATTGTG | N.D. | 50 |
| 168237 | Coding | 3 | 731 | TTATGAGGATCAGCATGTGT | N.D. | 51 |
| 168238 | Coding | 3 | 861 | CCTCTGGAACATCACCAGTT | N.D. | 52 |
| 168239 | Coding | 3 | 901 | GGATGAAGCACATCAGCAGC | N.D. | 53 |
| 168240 | Coding | 3 | 936 | TTCACCCCAGAAATACCAGG | N.D. | 54 |
| 168241 | Coding | 3 | 1082 | GAAACCAGGATATTCTCCCG | N.D. | 55 |
| 168242 | Coding | 3 | 1151 | TCACTGGCAGAGTAGTCATA | N.D. | 56 |
| 168243 | Coding | 3 | 1261 | TAATCCTGGCCAAGATGGCG | N.D. | 57 |
| 168244 | 3'UTR | 3 | 1401 | TCATCATCTTTAGCATCCTG | N.D. | 58 |
| 168245 | 3UTR | 3 | 1601 | GCAAAGACTGACCAGCTGCT | N.D. | 59 |
| 168246 | 3'UTR | 3 | 1748 | GACTACCCAGAAGATTCTGT | N.D. | 60 |
| 168247 | 3'UTR | 3 | 1881 | CTTCCCTCATCCTTACATTC | N.D. | 61 |
| 168248 | 3'UTR | 3 | 1985 | CCCGAGCCAGGAGAGAAAGG | N.D. | 62 |
| 168249 | 3'UTR | 3 | 2102 | CTTCCCCAGCAGAGACCACT | N.D. | 63 |
| 168250 | 3'UTR | 3 | 2281 | CCAATATCCTGAAGATGGCA | N.D. | 64 |
| 168251 | 3'UTR | 3 | 2481 | CCCAACTAATTCCTCCTCTC | N.D. | 65 |
| 168252 | 3'UTR | 3 | 2541 | TATAGATCCTGTCCCTCAGC | N.D. | 66 |
| 168253 | 3'UTR | 3 | 2631 | CTCCCAATAACTCACTCAGT | N.D. | 67 |
| 168254 | 3'UTR | 3 | 2826 | AAGAGATTCCTAACCCTGCC | N.D. | 68 |
| 168255 | 3'UTR | 3 | 2941 | CACACAAAGGAGGCTGCCTG | N.D. | 69 |
| 168256 | 3'UTR | 3 | 3051 | AAGTGGCAGCTAGCTCTACT | N.D. | 70 |
| 168257 | 3'UTR | 3 | 3321 | CACCCTCACCAAGTAAGCAG | N.D. | 71 |
| 168258 | 3'UTR | 3 | 3401 | TGCTTCTTCCCAGTGAGAAC | N.D. | 72 |
| 168259 | 3'UTR | 3 | 3941 | ATCAAGCAGGCATCTGATGA | N.D. | 73 |
| 168260 | 3'UTR | 3 | 4052 | CCCTCAGCCTGAGGTGCCAT | N.D. | 74 |
| 168261 | 3'UTR | 3 | 4357 | ATAATCCTCCACTCAGGCCC | N.D. | 75 |
| 168262 | 3'UTR | 3 | 4431 | CACTTAAGAAAAGCAGCCCT | N.D. | 76 |

TABLE 1-continued

Inhibition of human stearoyl-CoA desaturase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 168263 | 3'UTR | 3 | 4681 | CAGCAAGTCAGTGGCACAGT | N.D. | 77 |
| 168264 | 3'UTR | 3 | 4971 | GGCTAGTTATCCACCGCTTC | N.D. | 78 |
| 168265 | 3'UTR | 3 | 5044 | CCCAATCACAGAAAAGGCAT | N.D. | 79 |
| 168266 | 3'UTR | 3 | 5081 | AACTACTATATCCCACATAA | N.D. | 80 |

As shown in Table 1, SEQ ID NOs 18, 19, 20, 23, 25, 26, 29, 30, 31, 33, 39, 43 and 44 demonstrated at least 10% inhibition of human stearoyl-CoA desaturase expression in this assay. The target sites to which these preferred sequences are complementary are herein referred to as "active sites" and are therefore preferred sites for targeting by compounds of the present invention.

Example 16

Western Blot Analysis of Stearoyl-CoA Desaturase Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to stearoyl-CoA desaturase is used, with a radiolabelled or fluorescently labeled secondary antibody directed against the primary antibody species. Bands are visualized using a PHOSPHORIMAGER™ apparatus(Molecular Dynamics, Sunnyvale Calif.).

Example 17

Antisense Inhibition of Human Stearoyl-CoA Desaturase Expression by Chimeric Phosphorothioate Oligonucleotides having 2'-MOE Wings and a Deoxy Gap In accordance with the present invention, a series of oligonucleotides was designed to target different regions of the human stearoyl-CoA desaturase RNA, using published sequence (GenBank accession number AF097514, incorporated herein as SEQ ID NO: 3 and nucleotides 7371062 to 7389569 of the nucleotide sequence with the GenBank accession number NT_030059.7, incorporated herein as SEQ ID NO: 81). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human stearoyl-CoA desaturase mRNA levels in HepG2 cells by quantitative real-time PCR as described in other examples herein. The positive control oligonucleotide is ISIS 18078 (GTGCGCGCGAGCCGAAATC, SEQ ID NO: 82), a 2'-O-methoxyl gapmer (2'-O-methoxyethyls shown in bold) with a phosphorothioate backbone, which is targeted to human Jun-N-terminal kinase-2 (JNK2). Data are averages from two experiments and are shown in Table 2. If present, "N.D." indicates "no data".

TABLE 2

Inhibition of human stearoyl-CoA desaturase mRNA levels by chimeric phosphorothioate oligonucleotides having 2'-MOE wings and a deoxy gap

| ISIS # | Region | Target Seq ID | Target Site | SEQUENCE | % Inhib | Seq ID No | Control SEQ ID NO |
|---|---|---|---|---|---|---|---|
| 300870 | 5'UTR | 3 | 13 | ccgtgtccggtatttcctca | 53 | 83 | 82 |
| 300871 | 5'UTR | 3 | 25 | ggcaacgggtgaccgtgtcc | 75 | 84 | 82 |
| 300872 | 5'UTR | 3 | 42 | atttaaaggctagagctggc | 60 | 85 | 82 |
| 300873 | 5'UTR | 3 | 52 | cgagccgggaatttaaaggc | 40 | 86 | 82 |
| 300874 | 5'UTR | 3 | 178 | gaggctccggagcggagttc | 63 | 87 | 82 |
| 300875 | 5'UTR | 3 | 215 | ttggctctcggatgccggga | 69 | 88 | 82 |
| 300876 | Start Codon | 3 | 228 | gtgggccggcatcttggctc | 54 | 89 | 82 |
| 300877 | Coding | 3 | 239 | tcctgcagcaagtgggccgg | 88 | 90 | 82 |
| 300878 | Coding | 3 | 253 | agctagagatatcgtcctgc | 82 | 91 | 82 |

TABLE 2-continued

Inhibition of human stearoyl-CoA desaturase mRNA levels by chimeric phosphorothioate oligonucleotides having 2'-MOE wings and a deoxy gap

| ISIS # | Region | Target Seq ID | Target Site | SEQUENCE | % Inhib | Seq ID No | Control SEQ ID NO |
|---|---|---|---|---|---|---|---|
| 300879 | Coding | 3 | 482 | ccatacagggctcccaagtg | 42 | 92 | 82 |
| 300880 | Coding | 3 | 513 | gtagaacttgcaggtaggaa | 57 | 93 | 82 |
| 300881 | Coding | 3 | 566 | gctgttatgcccagggcact | 93 | 94 | 82 |
| 300882 | Coding | 3 | 667 | agacatcattctggaatgcc | 76 | 95 | 82 |
| 300883 | Coding | 3 | 709 | ctgaaaacttgtggtgggca | 42 | 96 | 82 |
| 300884 | Coding | 3 | 715 | gtgtttctgaaaacttgtgg | 60 | 97 | 82 |
| 300885 | Coding | 3 | 821 | aagtctagcgtactcccctt | 69 | 98 | 82 |
| 300886 | Coding | 3 | 873 | tttgtagtacctcctctgga | 36 | 99 | 82 |
| 300887 | Coding | 3 | 1045 | cataaggacgatatccgaag | 52 | 100 | 82 |
| 300888 | Stop Codon | 3 | 1303 | cccaaactcagccactcttg | 50 | 101 | 82 |
| 300889 | 3'UTR | 3 | 1347 | aaacctctgcctggctggtt | 87 | 102 | 82 |
| 300890 | 3'UTR | 3 | 1381 | gtagcattattcagtagtta | 58 | 103 | 82 |
| 300891 | 3'UTR | 3 | 1419 | tactggaatgggttaacatc | 42 | 104 | 82 |
| 300892 | 3'UTR | 3 | 1484 | tcagcttagcatcataaagg | 71 | 105 | 82 |
| 300893 | 3'UTR | 3 | 1597 | agactgaccagctgcttgcc | 45 | 106 | 82 |
| 300894 | 3'UTR | 3 | 1613 | gctggacactgagcaaagac | 65 | 107 | 82 |
| 300895 | 3'UTR | 3 | 1620 | tttggaagctggacactgag | 51 | 108 | 82 |
| 300896 | 3'UTR | 3 | 1668 | tctggagcaaagaccattcg | 91 | 109 | 82 |
| 300897 | 3'UTR | 3 | 1704 | cttcaaagctcacaacagct | 69 | 110 | 82 |
| 300898 | 3'UTR | 3 | 1711 | ccacctacttcaaagctcac | 68 | 111 | 82 |
| 300899 | 3'UTR | 3 | 1716 | tcaagccacctacttcaaag | 45 | 112 | 82 |
| 300900 | 3'UTR | 3 | 1723 | ctctagctcaagccacctac | 57 | 113 | 82 |
| 300901 | 3'UTR | 3 | 1814 | tgtgtcaaatgaagttgctt | 66 | 114 | 82 |
| 300902 | 3'UTR | 3 | 1842 | cccgacaatttacctgcttt | 75 | 115 | 82 |
| 300903 | 3'UTR | 3 | 1869 | ttacattcatacatgctaac | 22 | 116 | 82 |
| 300904 | 3'UTR | 3 | 1915 | tgtctgatcatggcgagagg | 90 | 117 | 82 |
| 300905 | 3'UTR | 3 | 1969 | aaggaagcatgctatgtggt | 87 | 118 | 82 |
| 300906 | 3'UTR | 3 | 1976 | ggagagaaaggaagcatgct | 81 | 119 | 82 |
| 300907 | 3'UTR | 3 | 2040 | aactatatgttgcggcattg | 59 | 120 | 82 |
| 300908 | 3'UTR | 3 | 2781 | tagatgttaacagagacccc | 15 | 121 | 82 |
| 300909 | 3'UTR | 3 | 2839 | aatcagggtagtgaagagat | 27 | 122 | 82 |
| 300910 | 3'UTR | 3 | 2859 | gggtagagccaggaatcaag | 32 | 123 | 82 |
| 300911 | 3'UTR | 3 | 3020 | agcagtggttcagtgaccct | 83 | 124 | 82 |
| 300912 | 3'UTR | 3 | 3035 | tactttcaaaagagaagcag | 27 | 125 | 82 |
| 300913 | 3'UTR | 3 | 3056 | cgtgaaagtggcagctagct | 81 | 126 | 82 |
| 300914 | 3'UTR | 3 | 3122 | ccttgtcttgagccatcagt | 77 | 127 | 82 |
| 300915 | 3'UTR | 3 | 3132 | ggtttgccagccttgtcttg | 78 | 128 | 82 |

TABLE 2-continued

Inhibition of human stearoyl-CoA desaturase mRNA levels by chimeric phosphorothioate oligonucleotides having 2'-MOE wings and a deoxy gap

| ISIS # | Region | Target Seq ID | Target Site | SEQUENCE | % Inhib | Seq ID No | Control SEQ ID NO |
|---|---|---|---|---|---|---|---|
| 300916 | 3'UTR | 3 | 3222 | cactggctcaacatgagcgc | 71 | 129 | 82 |
| 300917 | 3'UTR | 3 | 3238 | tgctctgtggctggcccact | 93 | 130 | 82 |
| 300918 | 3'UTR | 3 | 3252 | aataaaccctcttttgctct | 52 | 131 | 82 |
| 300919 | 3'UTR | 3 | 3259 | gactgaaaataaaccctctt | 54 | 132 | 82 |
| 300920 | 3'UTR | 3 | 3342 | agagcactgactcaggcggg | 81 | 133 | 82 |
| 300921 | 3'UTR | 3 | 3357 | ttgcactgccagctgagagc | 88 | 134 | 82 |
| 300922 | 3'UTR | 3 | 3371 | tacttctacaagcattgcac | 83 | 135 | 82 |
| 300923 | 3'UTR | 3 | 3383 | actgtttcctcctacttcta | 63 | 136 | 82 |
| 300924 | 3'UTR | 3 | 3409 | cttgcccttgcttcttccca | 70 | 137 | 82 |
| 300925 | 3'UTR | 3 | 3432 | tttcgaggtgaggcacttgg | 60 | 138 | 82 |
| 300926 | 3'UTR | 3 | 3480 | tcagccaaagctttgcagtt | 77 | 139 | 82 |
| 300927 | 3'UTR | 3 | 3655 | ttctgctttgatgactgagc | 86 | 140 | 82 |
| 300928 | 3'UTR | 3 | 2052 | atcctcggcctcaactatat | 58 | 141 | 82 |
| 300929 | 3'UTR | 3 | 2136 | tccttgttattaaagaaaaa | 35 | 142 | 82 |
| 300930 | 3'UTR | 3 | 2146 | ctaagaaatctccttgttat | 28 | 143 | 82 |
| 300931 | 3'UTR | 3 | 2162 | cttcttgatatatgaactaa | 11 | 144 | 82 |
| 300932 | 3'UTR | 3 | 2171 | acttcaagacttcttgatat | 45 | 145 | 82 |
| 300933 | 3'UTR | 3 | 2214 | aaattccatgagctgctgtt | 27 | 146 | 82 |
| 300934 | 3'UTR | 3 | 2245 | gaactgtaatgagcagctca | 36 | 147 | 82 |
| 300935 | 3'UTR | 3 | 2272 | tgaagatggcagagcagaaa | 27 | 148 | 82 |
| 300936 | 3'UTR | 3 | 2321 | tggaaatgccacagccatct | 70 | 149 | 82 |
| 300937 | 3'UTR | 3 | 2361 | cgacttcacctccttaaatc | 56 | 150 | 82 |
| 300938 | 3'UTR | 3 | 2397 | gcaatgtatatatgtatata | 31 | 151 | 82 |
| 300939 | 3'UTR | 3 | 2506 | ccagcagtggagaggaaatt | 27 | 152 | 82 |
| 300940 | 3'UTR | 3 | 2525 | cagcctctccatctcatgtc | 61 | 153 | 82 |
| 300941 | 3'UTR | 3 | 2570 | ctatgtgaagttcgctctta | 66 | 154 | 82 |
| 300942 | 3'UTR | 3 | 2589 | cgtgttctcagatcccttcc | 0 | 155 | 82 |
| 300943 | 3'UTR | 3 | 2676 | aactaattaatgaatggacc | 36 | 156 | 82 |
| 300944 | 3'UTR | 3 | 2700 | ttactcatttcaaggagaaa | 54 | 157 | 82 |
| 300945 | 3'UTR | 3 | 2715 | gaagccttctagttttttact | 55 | 158 | 82 |
| 300946 | 3'UTR | 3 | 2726 | cactgtggagagaagccttc | 71 | 159 | 82 |
| 300947 | 3'UTR | 3 | 2732 | gcacaacactgtggagagaa | 58 | 160 | 82 |
| 300948 | 3'UTR | 3 | 3679 | aatcttaatagagcaaagcc | 0 | 161 | 82 |
| 300949 | 3'UTR | 3 | 3707 | gactgagtgtttggtagtgt | 26 | 162 | 82 |
| 300950 | 3'UTR | 3 | 3771 | agcctctacgcaattaacac | 38 | 163 | 82 |
| 300951 | 3'UTR | 3 | 3825 | ctgaggtgaatagctcaaaa | 51 | 164 | 82 |
| 300952 | 3'UTR | 3 | 3834 | ccttttctactgaggtgaat | 65 | 165 | 82 |

TABLE 2-continued

Inhibition of human stearoyl-CoA desaturase mRNA levels by chimeric phosphorothioate oligonucleotides having 2'-MOE wings and a deoxy gap

| ISIS # | Region | Target Seq ID | Target Site | SEQUENCE | % Inhib | Seq ID No | Control SEQ ID NO |
|---|---|---|---|---|---|---|---|
| 300953 | 3'UTR | 3 | 3911 | tagaaataccagcagacatt | 37 | 166 | 82 |
| 300954 | 3'UTR | 3 | 3993 | gcacacgattacaataggaa | 62 | 167 | 82 |
| 300955 | 3'UTR | 3 | 3999 | tccatggcacacgattacaa | 64 | 168 | 82 |
| 300956 | 3'UTR | 3 | 4004 | tcagatccatggcacacgat | 54 | 169 | 82 |
| 300957 | 3'UTR | 3 | 4041 | aggtgccatccagccttatg | 12 | 170 | 82 |
| 300958 | 3'UTR | 3 | 4053 | gccctcagcctgaggtgcca | 21 | 171 | 82 |
| 300959 | 3'UTR | 3 | 4132 | agctttagaatcttgaaaat | 25 | 172 | 82 |
| 300960 | 3'UTR | 3 | 4150 | aatgtgtcacttgaattgag | 26 | 173 | 82 |
| 300961 | 3'UTR | 3 | 4193 | ctgttagaaatccggactct | 33 | 174 | 82 |
| 300962 | 3'UTR | 3 | 4205 | ccaaagcagggactgttaga | 41 | 175 | 82 |
| 300963 | 3'UTR | 3 | 4261 | caacactgtgattagaaaag | 20 | 176 | 82 |
| 300964 | 3'UTR | 3 | 4321 | cttcagtagggtctcaggtg | 43 | 177 | 82 |
| 300965 | 3'UTR | 3 | 4331 | ctaccagccacttcagtagg | 37 | 178 | 82 |
| 300966 | 3'UTR | 3 | 4347 | actcaggccccttttctac | 34 | 179 | 82 |
| 300967 | 3'UTR | 3 | 4364 | gatactgataatcctccact | 18 | 180 | 82 |
| 300968 | 3'UTR | 3 | 4379 | aatcctgcaaatcgtgatac | 34 | 181 | 82 |
| 300969 | 3'UTR | 3 | 4420 | agcagccctaacaaaagttt | 34 | 182 | 82 |
| 300970 | 3'UTR | 3 | 4535 | aaattttccattttaaatgc | 23 | 183 | 82 |
| 300971 | 3'UTR | 3 | 4578 | cacttacagagaatacaccc | 38 | 184 | 82 |
| 300972 | 3'UTR | 3 | 4584 | gagctacacttacagagaat | 26 | 185 | 82 |
| 300973 | 3'UTR | 3 | 4628 | aacatggccacctcgctttt | 16 | 186 | 82 |
| 300974 | 3'UTR | 3 | 4645 | gccttaaccaccagcataac | 40 | 187 | 82 |
| 300975 | 3'UTR | 3 | 4653 | aggccctggccttaaccacc | 60 | 188 | 82 |
| 300976 | 3'UTR | 3 | 4658 | tggagaggccctggccttaa | 55 | 189 | 82 |
| 300977 | 3'UTR | 3 | 4786 | tcatgcctcaaaactgccct | 34 | 190 | 82 |
| 300978 | 3'UTR | 3 | 4800 | ctaaaaagcattagtcatgc | 0 | 191 | 82 |
| 300979 | 3'UTR | 3 | 4834 | agaattcctgtgctgaagga | 13 | 192 | 82 |
| 300980 | 3'UTR | 3 | 4841 | ggtcttgagaattcctgtgc | 47 | 193 | 82 |
| 300981 | 3'UTR | 3 | 4846 | actcaggtcttgagaattcc | 43 | 194 | 82 |
| 300982 | 3'UTR | 3 | 4868 | ggacattcctattataaaaa | 9 | 195 | 82 |
| 300983 | 3'UTR | 3 | 4892 | acacggacgtatcaagttca | 41 | 196 | 82 |
| 300984 | 3'UTR | 3 | 5024 | cctctgtatgtttccgtggc | 67 | 197 | 82 |
| 300985 | exon | 81 | 505 | tgcgaggagttgactggcgc | 39 | 198 | 82 |
| 300986 | exon | 81 | 512 | ggcaaagtgcgaggagttga | 45 | 199 | 82 |
| 300987 | exon:intron | 81 | 799 | ggaaactcacatcgtcctgc | 33 | 200 | 82 |
| 300988 | exon:intron | 81 | 1614 | ggctgcttaccccaaagcca | 29 | 201 | 82 |
| 300989 | intron | 81 | 2854 | ctcagttgcatttcactgta | 45 | 202 | 82 |

TABLE 2-continued

Inhibition of human stearoyl-CoA desaturase mRNA levels by chimeric phosphorothioate oligonucleotides having 2'-MOE wings and a deoxy gap

| ISIS # | Region | Target Seq ID | Target Site | SEQUENCE | % Inhib | Seq ID No | Control SEQ ID NO |
|---|---|---|---|---|---|---|---|
| 300990 | intron | 81 | 3557 | gtgggaagagaagatgtcca | 4 | 203 | 82 |
| 300991 | intron | 81 | 5287 | gccttctctaaggttttaag | 50 | 204 | 82 |
| 300992 | intron:exon | 81 | 5633 | tagaataccoctgccaggag | 34 | 205 | 82 |
| 300993 | exon:intron | 81 | 5764 | aacttcttacctggaatgcc | 18 | 206 | 82 |
| 300994 | intron | 81 | 7232 | ccttgcaaaagagctcatac | 56 | 207 | 82 |
| 300995 | exon:intron | 81 | 7900 | cttcactcacctcctctgga | 0 | 208 | 82 |
| 300996 | intron | 81 | 8630 | tttgcactgtctctccccac | 13 | 209 | 82 |
| 300997 | intron | 81 | 8878 | tcagtggtttcttacacttg | 77 | 210 | 82 |
| 300998 | intron:exon | 81 | 9799 | tttgtagtacctacattgac | 4 | 211 | 82 |
| 300999 | exon:intron | 81 | 10032 | gctgacttacccacagctcc | 10 | 212 | 82 |
| 301000 | intron | 81 | 10163 | tactgcccctaattttata | 0 | 213 | 82 |
| 301001 | intron | 81 | 12377 | ccatttgcgatacaggaaac | 27 | 214 | 82 |
| 301002 | intron:exon | 81 | 14001 | aagccctcacctgaaacaaa | 22 | 215 | 82 |

As shown in Table 2, SEQ ID NOs 83, 84, 85, 87, 88, 89, 90, 91, 93, 94, 95, 97, 98, 100, 101, 102, 103, 105, 107, 108, 109, 110, 111, 113, 114, 115, 117, 118, 119, 120, 124, 126, 127, 128, 129, 130, 131, 132, 133, 134, 135, 136, 137, 138, 139, 140, 141, 149, 150, 153, 154, 157, 158, 159, 160, 164, 165, 167, 168, 169, 188, 189, 197, 204, 207 and 210 demonstrated at least 50% inhibition of human stearoyl-CoA desaturase expression in this assay. Preferred antisense oligonucleotide sequences are SEQ ID NOs 94, 130, 140 and 134. The target sites to which these preferred sequences are complementary are herein referred to as "active sites" and are therefore preferred sites for targeting by compounds of the present invention.

Example 18

Antisense Inhibition of Mouse Stearoyl-CoA Desaturase Expression by Chimeric Phosphorothioate Oligonucleotides having 2'-MOE Wings and a Deoxy Gap In accordance with the present invention, a series of oligonucleotides was designed to target different regions of the mouse stearoyl-CoA desaturase RNA, using published sequence (GenBank Accession number M21280.1, incorporated herein as SEQ ID NO: 216; GenBank Accession number M21281.1, incorporated herein as SEQ ID NO: 217; GenBank Accession number M21282.1, incorporated herein as SEQ ID NO: 218; GenBank Accession number M21283.1, incorporated herein as SEQ ID NO: 219; GenBank Accession number M21284.1, incorporated herein as SEQ ID NO: 220; GenBank Accession number M21285.1, incorporated herein as SEQ ID NO: 221; the concatenation of SEQ ID NOs 216, 217, 218, 219, 220 and 221, incorporated herein as SEQ ID NO: 222). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

TABLE 3

Chimeric phosphorothioate oligonucleotides having 2'-MOE wings and a deoxy gap targeted to mouse stearoyl-CoA

| ISIS # | Region | Target SEQ ID NO | Target Site | Sequence | SEQ ID NO |
|---|---|---|---|---|---|
| 180548 | 5'UTR | 222 | 9 | agatctcttggagcatgtgg | 223 |
| 180549 | 5'UTR | 222 | 71 | cttctctcgttcatttccgg | 224 |
| 180550 | 5'UTR | 222 | 126 | cttctttcatttcaggacgg | 225 |
| 180551 | 5'UTR | 222 | 161 | tccctcctcatcctgatagg | 226 |

TABLE 3-continued

Chimeric phosphorothioate oligonucleotides having 2'-MOE wings and a deoxy gap targeted to mouse stearoyl-CoA

| ISIS # | Region | Target SEQ ID NO | Target Site | Sequence | SEQ ID NO |
|---|---|---|---|---|---|
| 180552 | 5'UTR | 222 | 191 | cctccagacgtactccagct | 227 |
| 180553 | 5'UTR | 222 | 211 | aggaccatgagaatgatgtt | 228 |
| 180554 | 5'UTR | 222 | 231 | acaggcctcccaagtgcagc | 229 |
| 180555 | 5'UTR | 222 | 250 | ggaaccagtatgatcccgta | 230 |
| 180557 | 5'UTR | 222 | 291 | agtagaaaatcccgaagagg | 231 |
| 180558 | 5'UTR | 222 | 321 | cggctgtgatgcccagagcg | 232 |
| 180559 | 5'UTR | 222 | 341 | gctccagaggcgatgagccc | 233 |
| 180560 | 5'UTR | 222 | 361 | cgagccttgtaagttctgtg | 234 |
| 180561 | 5'UTR | 222 | 391 | gcaatgattaggaagatccg | 235 |
| 180562 | 5'UTR | 222 | 421 | tacacgtcattttggaacgc | 236 |
| 180563 | 5'UTR | 222 | 441 | ggtgatctcgggcccagtcg | 237 |
| 180564 | 5'UTR | 222 | 471 | cgtgtgtttctgagaacttg | 238 |
| 180565 | 5'UTR | 222 | 591 | cggctttcaggtcagacatg | 239 |
| 180566 | 5'UTR | 222 | 611 | ctggaacatcaccagcttct | 240 |
| 180567 | 5'UTR | 222 | 648 | agcacatcagcaggaggccg | 241 |
| 180568 | 5'UTR | 222 | 651 | tgaagcacatcagcaggagg | 242 |
| 180569 | 5'UTR | 222 | 691 | gtctcgcccagcagtacca | 243 |
| 180570 | 5'UTR | 222 | 741 | gcaccagagtgtatcgcaag | 244 |
| 180571 | 5'UTR | 222 | 761 | caccagccaggtggcgttga | 245 |
| 180572 | 5'UTR | 222 | 781 | tagagatgcgcggcactgtt | 246 |
| 180573 | 5'UTR | 222 | 812 | ttgaatgttcttgtcgtagg | 247 |
| 180574 | Start Codon | 222 | 855 | cctcgcccacggcacccagg | 248 |
| 180575 | Coding | 222 | 869 | gtagttgtggaagccctcgc | 249 |
| 180576 | Coding | 222 | 881 | gaaggtgtggtggtagttgt | 250 |
| 180577 | Coding | 222 | 911 | gcggtactcactggcagagt | 251 |
| 180578 | Coding | 222 | 929 | ggtgaagttgatgtgccagc | 252 |
| 180579 | Coding | 222 | 1011 | tcctggctaagacagtagcc | 253 |
| 180580 | Coding | 222 | 1031 | cccgtctccagttctcttaa | 254 |
| 180581 | Coding | 222 | 1039 | ttgtgactcccgtctccagt | 255 |
| 180582 | Coding | 222 | 1049 | tcagctactcttgtgactcc | 256 |

In a further embodiment of the present invention, a series of oligonucleotides was designed to target different regions of the mouse stearoyl-CoA desaturase RNA, using published sequences (GenBank Accession number M21280.1, incorporated herein as SEQ ID NO: 216; GenBank Accession number M21281.1, incorporated herein as SEQ ID NO: 217; GenBank Accession number M21282.1, incorporated herein as SEQ ID NO: 218; GenBank Accession number M21283.1, incorporated herein as SEQ ID NO: 219; GenBank Accession number M21284.1, incorporated herein as SEQ ID NO: 220; GenBank Accession number M21285.1, incorporated herein as SEQ ID NO: 221; the concatenation of SEQ ID NOs 216, 217, 218, 219, 220 and 221, incorporated herein as SEQ ID NO: 222). The oligonucleotides are shown in Table 4. "Target site" indicates the first (5'-most) nucleotide number on the particular target sequence to which the oligonucleotide binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

Probes and primers to mouse stearoyl-CoA desaturase were designed to hybridize to a mouse stearoyl-CoA desaturase sequence, using published sequence information (SEQ ID NO: 222). For mouse stearoyl-CoA desaturase the PCR primers were:
forward primer: ACACCAGAGACATGGGCAAGT (SEQ ID NO: 257)
reverse primer: CATCACACACTGGCTTCAGGAA (SEQ ID NO: 258) and the PCR probe was: FAM-CTGAAGT-GAGGTCCATTAG-TAMRA
(SEQ ID NO: 259) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:
forward primer: GAAGGTGAAGGTCGGAGTC (SEQ ID NO:260)
reverse primer: GAAGATGGTGATGGGATTTC (SEQ ID NO:261) and the PCR probe was: 5' JOE-CAAGCTTC-CCGTTCTCAGCC-TAMRA 3' (SEQ ID NO: 262) where JOE is the fluorescent reporter dye and TAMRA is the quencher dye.

The compounds were analyzed for their effect on mouse stearoyl-CoA desaturase MRNA levels in b.END cells by quantitative real-time PCR as described in other examples herein. The positive control oligonucleotide is ISIS 18078 (GTGCGCGCGAGCCCGAAATC, SEQ ID NO: 82), a 2'-O-methoxyl gapmer (2'-O-methoxyethyls shown in bold) with a phosphorothioate backbone, which is targeted to human Jun-N-terminal kinase-2 (JNK2). Data are averages from two experiments and are shown in Table 4. If present, "N.D." indicates "no data".

TABLE 4

Inhibition of mouse stearoyl-CoA desaturase mRNA levels by chimeric phosphorothioate oligonucleotides having 2'-MOE wings and a deoxy gap

| Isis # | Region | Target SEQ ID NO | Target Site | Sequence | % Inhib | SEQ ID NO | Control SEQ ID NO |
|---|---|---|---|---|---|---|---|
| 185154 | exon:intron | 216 | 876 | ggaagctcacctcttggagc | 48 | 263 | 82 |
| 185155 | exon:intron | 217 | 269 | ctgctcaccgaagagggcag | 0 | 264 | 82 |
| 185156 | intron:exon | 218 | 1 | gtagtagaaaatccctgcaa | 6 | 265 | 82 |
| 185157 | exon:intron | 219 | 202 | tcccttacctcctctggaac | 0 | 266 | 82 |
| 185158 | exon:intron | 220 | 228 | tgacttacccacggcaccca | 41 | 267 | 82 |
| 185159 | intron:exon | 221 | 1 | gtggaagccctcgcctgcaa | 83 | 268 | 82 |
| 185160 | 5'UTR | 222 | 68 | ctggctaccgccactcacaa | 0 | 269 | 82 |
| 185161 | 5'UTR | 222 | 142 | aagcctaggactttggtctg | 51 | 270 | 82 |
| 185162 | 5'UTR | 222 | 148 | gtgtgcaagcctaggacttt | 0 | 271 | 82 |
| 185163 | 5'UTR | 222 | 156 | taggaattgtgtgcaagcct | 0 | 272 | 82 |
| 185164 | 5'UTR | 222 | 275 | atctgctgttccctctgcct | 0 | 273 | 82 |
| 185165 | 5'UTR | 222 | 445 | tccagagtagaccttggagg | 15 | 274 | 82 |
| 185166 | 5'UTR | 222 | 571 | ctagccaaggaagccaggcg | 12 | 275 | 82 |
| 185167 | 5'UTR | 222 | 581 | gcagagatagctagccaagg | 2 | 276 | 82 |
| 185168 | 5'UTR | 222 | 612 | ttttatcggctgccagcaaa | 41 | 277 | 82 |
| 185169 | 5'UTR | 222 | 644 | ggatgaccgtgttcagtatt | 41 | 278 | 82 |
| 185170 | 5'UTR | 222 | 697 | tggctgtgcacagatctcct | 82 | 279 | 82 |
| 185171 | 5'UTR | 222 | 708 | tcagcccggtctggctgtgc | 56 | 280 | 82 |
| 185172 | 5'UTR | 222 | 748 | gcgcttggaaacctgccctc | 59 | 281 | 82 |
| 185173 | 5'UTR | 222 | 768 | tgtaggcgagtggcggaact | 43 | 282 | 82 |
| 185174 | 5'UTR | 222 | 795 | gtggacttcggttccggagc | 31 | 283 | 82 |
| 185175 | 5'UTR | 222 | 830 | ttgctcgcctcactttccca | 79 | 284 | 82 |
| 185176 | 5'UTR | 222 | 854 | gtgggccggcatgatgatag | 67 | 285 | 82 |
| 185177 | 5'UTR | 222 | 877 | gaactggagatctcttggag | 51 | 286 | 82 |
| 185178 | Coding | 222 | 1150 | tagaaaatcccgaagagggc | 0 | 287 | 82 |
| 185179 | Coding | 222 | 1160 | ggtcatgtagtagaaaatcc | 10 | 288 | 82 |

TABLE 4-continued

Inhibition of mouse stearoyl-CoA desaturase mRNA levels by chimeric phosphorothioate oligonucleotides having 2'-MOE wings and a deoxy gap

| Isis # | Region | Target SEQ ID NO | Target Site | Sequence | % Inhib | SEQ ID NO | Control SEQ ID NO |
|---|---|---|---|---|---|---|---|
| 185180 | Coding | 222 | 1165 | gcgctggtcatgtagtagaa | 40 | 289 | 82 |
| 185181 | Coding | 222 | 1676 | ggattgaatgttcttgtcgt | 81 | 290 | 82 |
| 185182 | Coding | 222 | 1681 | tcccgggattgaatgttctt | 46 | 291 | 82 |
| 185183 | Coding | 222 | 1688 | gatattctcccgggattgaa | 39 | 292 | 82 |
| 185184 | Coding | 222 | 1858 | gtagccttagaaactttctt | 52 | 293 | 82 |
| 185185 | Stop Codon | 222 | 1918 | cccaaagctcagctactctt | 65 | 294 | 82 |
| 185186 | 3'UTR | 222 | 1934 | aacaggaactcagaagccca | 90 | 295 | 82 |
| 185187 | 3'UTR | 222 | 1967 | cagaatattaaatctctgcc | 48 | 296 | 82 |
| 185188 | 3'UTR | 222 | 1984 | agttgttagttaatcaacag | 0 | 297 | 82 |
| 185189 | 3'UTR | 222 | 2159 | aattgtatatgcatttatca | 62 | 298 | 82 |
| 185190 | 3'UTR | 222 | 2208 | ctgtatagaatgttcaaatt | 2 | 299 | 82 |
| 185191 | 3'UTR | 222 | 2236 | acagcatgttccttggcttt | 51 | 300 | 82 |
| 185192 | 3'UTR | 222 | 2246 | tagcatcaaaacagcatgtt | 46 | 301 | 82 |
| 185193 | 3'UTR | 222 | 2259 | accatgctcaccctagcatc | 45 | 302 | 82 |
| 185194 | 3'UTR | 222 | 2408 | aaggatcagtatttcagaaa | 39 | 303 | 82 |
| 185195 | 3'UTR | 222 | 2552 | tctctcgagacaatctactt | 67 | 304 | 82 |
| 185196 | 3'UTR | 222 | 2821 | cttcagttaccaaaagctaa | 37 | 305 | 82 |
| 185197 | 3'UTR | 222 | 2887 | aaatgtcagctgtttagtta | 0 | 306 | 82 |
| 185198 | 3'UTR | 222 | 3002 | ggcaacccaggcaacacctc | 39 | 307 | 82 |
| 185199 | 3'UTR | 222 | 3017 | gccacgaaagaaactggcaa | 23 | 308 | 82 |
| 185200 | 3'UTR | 222 | 3102 | atgttccccaagggcttcat | 86 | 309 | 82 |
| 185201 | 3'UTR | 222 | 3112 | tccctggcagatgttcccca | 76 | 310 | 82 |
| 185202 | 3'UTR | 222 | 3427 | ctggctctgcttcctgaagc | 48 | 311 | 82 |
| 185203 | 3'UTR | 222 | 3569 | gctgagctgttaactcacaa | 71 | 312 | 82 |
| 185204 | 3'UTR | 222 | 3640 | cacacaccgagacagatcaa | 79 | 313 | 82 |
| 185205 | 3TUTR | 222 | 3828 | caggaagcagaccctcttcc | 42 | 314 | 82 |
| 185206 | 3'UTR | 222 | 3958 | aatactgatgtgatgttttc | 65 | 315 | 82 |
| 185207 | 3'UTR | 222 | 3968 | atggttctaaaatactgatg | 36 | 316 | 82 |
| 185208 | 3'UTR | 222 | 4046 | actgagtgtttggcacctta | 79 | 317 | 82 |
| 185209 | 3'UTR | 222 | 4066 | ggctctgattctacaagtga | 61 | 318 | 82 |
| 185210 | 3'UTR | 222 | 4116 | tcaacaaaacagctcagagc | 83 | 319 | 82 |
| 185211 | 3'UTR | 222 | 4127 | gattttctacttcaacaaaa | 56 | 320 | 82 |
| 185212 | 3'UTR | 222 | 4333 | cttaaagacaccaggacctc | 56 | 321 | 82 |
| 185213 | 3'UTR | 222 | 4387 | catctggaaactgttataaa | 45 | 322 | 82 |
| 185214 | 3'UTR | 222 | 4466 | ctaagggaaggagtgagact | 42 | 323 | 82 |
| 185215 | 3'UTR | 222 | 4608 | ttacttcccaccaaatttga | 59 | 324 | 82 |
| 185216 | 3'UTR | 222 | 4652 | tgacaatgataacgaggacg | 81 | 325 | 82 |

TABLE 4-continued

Inhibition of mouse stearoyl-CoA desaturase mRNA levels by chimeric phosphorothioate oligonucleotides having 2'-MOE wings and a deoxy gap

| Isis # | Region | Target SEQ ID NO | Target Site | Sequence | % Inhib | SEQ ID NO | Control SEQ ID NO |
|---|---|---|---|---|---|---|---|
| 185217 | 3'UTR | 222 | 4760 | cagatggtggctttgctaac | 0 | 326 | 82 |
| 185218 | 3'UTR | 222 | 4825 | ttgttacaagagaaaggata | 68 | 327 | 82 |
| 185219 | 3'UTR | 222 | 4884 | tcagatacttagcccaggag | 74 | 328 | 82 |
| 185220 | 3'UTR | 222 | 4902 | tgttgagatgtgagactgtc | 50 | 329 | 82 |
| 185221 | 3'UTR | 222 | 5010 | cacctcagaactgcccttga | 73 | 330 | 82 |
| 185222 | 3'UTR | 222 | 5018 | gctctaatcacctcagaact | 84 | 331 | 82 |
| 185223 | 3'UTR | 222 | 5074 | ggagtctgtatgaatacctc | 64 | 332 | 82 |
| 185224 | 3'UTR | 222 | 5132 | tctctgggaagagcaatgta | 58 | 333 | 82 |
| 185225 | 3'UTR | 222 | 5170 | gtaggtagtcttgcactttg | 36 | 334 | 82 |
| 185226 | 3'UTR | 222 | 5211 | aggaagggaaaggtttcctg | 38 | 335 | 82 |
| 185227 | 3'UTR | 222 | 5268 | tacacttgggtcacaaataa | 49 | 336 | 82 |
| 185228 | 3'UTR | 222 | 5280 | aatcatccaaattacacttg | 50 | 337 | 82 |
| 185229 | 3'UTR | 222 | 5303 | cttcaagagttgatattaat | 60 | 338 | 82 |
| 185230 | 3'UTR | 222 | 5329 | atacaatctcaatcagtaca | 76 | 339 | 82 |
| 185231 | 3'UTR | 222 | 5347 | cacttttattaggaacaaat | 0 | 340 | 82 |

As shown in Table 4, SEQ ID NOs 263, 267, 268, 270, 277, 278, 279, 280, 281, 282, 284, 285, 286, 289, 290, 291, 293, 294, 295, 296, 298, 300, 301, 302, 304, 309, 310, 311, 312, 313, 314, 315, 317, 318, 319, 320, 321, 322, 323, 324, 325, 327, 328, 329, 330, 331, 332, 333, 336, 337, 338, 339 demonstrated at least 40% inhibition of stearoyl-CoA desaturase in this experiment and are therefore preferred. More preferred are SEQ ID NOs 295, 331 and 268. The target regions to which these preferred sequences are complementary are herein referred to as "preferred target segments" and are therefore preferred for targeting by compounds of the present invention.

In a further embodiment of the present invention, a series of oligonucleotides was designed to target different regions of the mouse stearoyl-CoA desaturase RNA, using published sequences (GenBank Accession number M21280.1, incorporated herein as SEQ ID NO: 216; GenBank Accession number M21281.1, incorporated herein as SEQ ID NO: 217; GenBank Accession number M21282.1, incorporated herein as SEQ ID NO: 218; GenBank Accession number M21283.1, incorporated herein as SEQ ID NO: 219; GenBank Accession number M21284.1, incorporated herein as SEQ ID NO: 220; GenBank Accession number M21285.1, incorporated herein as SEQ ID NO: 221; the concatenation of SEQ ID NOs 216, 217, 218, 219, 220 and 221, incorporated herein as SEQ ID NO: 222). The oligonucleotides are shown in Table 5. "Target site" indicates the first (5'-most) nucleotide number on the particular target sequence to which the oligonucleotide binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

Probes and primers to mouse stearoyl-CoA desaturase were designed to hybridize to a mouse stearoyl-CoA desaturase sequence, using published sequence information (SEQ ID NO: 222). For mouse stearoyl-CoA desaturase the PCR primers were:
forward primer: TTCCGCCACTCGCCTACA (SEQ ID NO: 341)
reverse primer: CTTTCCCAGTGCTGAGATCGA (SEQ ID NO: 342) and the PCR probe was:
FAM-CAACGGGCTCCGGAACCGAA-TAMRA
(SEQ ID NO: 343) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:
forward primer: GAAGGTGAAGGTCGGAGTC (SEQ ID NO:261)
reverse primer: GAAGATGGTGATGGGATTTC (SEQ ID NO:262) and the PCR probe was: 5' JOE-CAAGCTTC-CCGTTCTCAGCC-TAMRA 3' (SEQ ID NO: 263) where JOE is the fluorescent reporter dye and TAMRA is the quencher dye.

The compounds were analyzed for their effect on mouse stearoyl-CoA desaturase mRNA levels in primary mouse hepatocytes by quantitative real-time PCR as described in other examples herein. The positive control oligonucleotide is ISIS 18078 (GTGCGCGCGAGCCCGAAATC, SEQ ID NO: 82), a 2'-O-methoxyl gapmer (2'-O-methoxyethyls shown in bold) with a phosphorothioate backbone, which is targeted to human Jun-N-terminal kinase-2 (JNK2). Data are averages from two experiments and are shown in Table 5. If present, "N.D." indicates "no data".

TABLE 5

Inhibition of mouse stearoyl-CoA desaturase mRNA levels by chimeric phosphorothioate oligonucleotides having 2'-MOE wings and a deoxy gap

| Isis # | Region | Target SEQ ID NO | Target Site | Sequence | % Inhib | SEQ ID NO | Control SEQ ID NO |
|---|---|---|---|---|---|---|---|
| 180556 | 5'UTR | 222 | 261 | gcttgcaggagggaaccagt | 40 | 344 | 82 |
| 244459 | 5'UTR | 222 | 138 | ctaggactttggtctggcgc | 6 | 345 | 82 |
| 244461 | 5'UTR | 222 | 280 | gcgcaatctgctgttccctc | 0 | 346 | 82 |
| 244464 | 5'UTR | 222 | 401 | agggcgcgctgctccaaccc | 0 | 347 | 82 |
| 244467 | 5'UTR | 222 | 462 | aagaaagcaagtagattcc | 0 | 348 | 82 |
| 244470 | 5'UTR | 222 | 692 | gtgcacagatctcctgggct | 35 | 349 | 82 |
| 244472 | 5'UTR | 222 | 736 | ctgccctcctgactctcggg | 54 | 350 | 82 |
| 244476 | Coding | 222 | 878 | agaactggagatctcttgga | 71 | 351 | 82 |
| 244479 | Coding | 222 | 1020 | cctcctcatcctgataggtg | 16 | 352 | 82 |
| 244481 | Coding | 222 | 1045 | acgtactccagcttgggcgg | 50 | 353 | 82 |
| 244484 | Coding | 222 | 1057 | atgttcctccagacgtactc | 33 | 354 | 82 |
| 244487 | Coding | 222 | 1062 | gaatgatgttcctccagacg | 43 | 355 | 82 |
| 244490 | Coding | 222 | 1068 | ccatgagaatgatgttcctc | 50 | 356 | 82 |
| 244493 | Coding | 222 | 1098 | tcccgtacaggcctcccaag | 54 | 357 | 82 |
| 244495 | Coding | 222 | 1128 | tgtagagcttgcaggaggga | 10 | 358 | 82 |
| 244498 | Coding | 222 | 1264 | gccatggtgttggcaatgat | 41 | 359 | 82 |
| 244501 | Coding | 222 | 1324 | tctgagaacttgtggtgggc | 18 | 360 | 82 |
| 244504 | Coding | 222 | 1329 | gtgtttctgagaacttgtgg | 50 | 361 | 82 |
| 244507 | Coding | 222 | 1334 | ggcgtgtgtttctgagaact | 63 | 362 | 82 |
| 244510 | Coding | 222 | 1347 | aattgtgagggtcggcgtgt | 11 | 363 | 82 |
| 244514 | Coding | 222 | 1357 | ccacggcgggaattgtgagg | 47 | 364 | 82 |
| 244517 | Coding | 222 | 1363 | aagaagccacggcgggaatt | 16 | 365 | 82 |
| 244520 | Coding | 222 | 1387 | agcagccaacccacgtgaga | 51 | 366 | 82 |
| 244523 | Coding | 222 | 1395 | tgcgcacaagcagccaaccc | 67 | 367 | 82 |
| 244526 | Coding | 222 | 1400 | gtgtttgcgcacaagcagcc | 52 | 368 | 82 |
| 244528 | Coding | 222 | 1408 | acagccgggtgtttgcgcac | 63 | 369 | 82 |
| 244532 | Coding | 222 | 1413 | ctttgacagccgggtgtttg | 3 | 370 | 82 |
| 244535 | Coding | 222 | 1418 | cttctctttgacagccgggt | 50 | 371 | 82 |
| 244538 | Coding | 222 | 1423 | ccgcccttctctttgacagc | 64 | 372 | 82 |
| 244541 | Coding | 222 | 1435 | atgtccagttttccgccctt | 55 | 373 | 82 |
| 244542 | Coding | 222 | 1440 | cagacatgtccagttttccg | 55 | 374 | 82 |
| 244546 | Coding | 222 | 1445 | caggtcagacatgtccagtt | 48 | 375 | 82 |
| 244549 | Coding | 222 | 1450 | gctttcaggtcagacatgtc | 49 | 376 | 82 |
| 244553 | Coding | 222 | 1455 | tctcggctttcaggtcagac | 50 | 377 | 82 |
| 244554 | Coding | 222 | 1460 | cagcttctcggctttcaggt | 37 | 378 | 82 |
| 244557 | Coding | 222 | 1465 | atcaccagcttctcggcttt | 20 | 379 | 82 |
| 244560 | Coding | 222 | 1470 | ggaacatcaccagcttctcg | 42 | 380 | 82 |

TABLE 5-continued

Inhibition of mouse stearoyl-CoA desaturase mRNA levels by chimeric phosphorothioate oligonucleotides having 2'-MOE wings and a deoxy gap

| Isis # | Region | Target SEQ ID NO | Target Site | Sequence | % Inhib | SEQ ID NO | Control SEQ ID NO |
|---|---|---|---|---|---|---|---|
| 244565 | Coding | 222 | 1477 | ctcctctggaacatcaccag | 17 | 381 | 82 |
| 244567 | Coding | 222 | 1486 | ttgtagtacctcctctggaa | 0 | 382 | 82 |
| 244569 | Coding | 222 | 1516 | aggatgaagcacatcagcag | 29 | 383 | 82 |
| 244572 | Coding | 222 | 1525 | agcgtgggcaggatgaagca | 45 | 384 | 82 |
| 244577 | Coding | 222 | 1538 | gtaccagggcaccagcgtgg | 37 | 385 | 82 |
| 244578 | Coding | 222 | 1543 | cagcagtaccagggcaccag | 25 | 386 | 82 |
| 244581 | Coding | 222 | 1548 | cgccccagcagtaccagggc | 13 | 387 | 82 |
| 244585 | Coding | 222 | 1583 | gaaggtgctaacgaacaggc | 18 | 388 | 82 |
| 244589 | Coding | 222 | 1627 | ctgttcaccagccaggtggc | 37 | 389 | 82 |
| 244591 | Coding | 222 | 1633 | gcggcactgttcaccagcca | 3 | 390 | 82 |
| 244595 | Coding | 222 | 1693 | accaggatattctcccggga | 62 | 391 | 82 |
| 244598 | Coding | 222 | 1732 | tggtagttgtggaagccctc | 54 | 392 | 82 |
| 244599 | Coding | 222 | 1768 | tactcactggcagagtagtc | 19 | 393 | 82 |
| 244602 | Coding | 222 | 1773 | agcggtactcactggcagag | 31 | 394 | 82 |
| 244607 | Coding | 222 | 1778 | gtgccagcggtactcactgg | 5 | 395 | 82 |
| 244609 | Coding | 222 | 1783 | ttgatgtgccagcggtactc | 29 | 396 | 82 |
| 244613 | Coding | 222 | 1792 | gtggtgaagttgatgtgcca | 40 | 397 | 82 |
| 244615 | Coding | 222 | 1798 | aagaacgtggtgaagttgat | 12 | 398 | 82 |
| 244619 | Coding | 222 | 1860 | cagtagccttagaaactttc | 75 | 399 | 82 |
| 244620 | Coding | 222 | 1885 | ccagttctcttaatcctggc | 63 | 400 | 82 |
| 244623 | Coding | 222 | 1891 | ccgtctccagttctcttaat | 37 | 401 | 82 |
| 244626 | 3'UTR | 222 | 2006 | taacaccccgatagcaatat | 59 | 402 | 82 |
| 244630 | 3'UTR | 222 | 2365 | gagggtggacagacacaggc | 4 | 403 | 82 |
| 244633 | 3'UTR | 222 | 2445 | cttgaagctaggaacaagga | 68 | 404 | 82 |
| 244636 | 3'UTR | 222 | 2647 | tatggctacctctctctctc | 82 | 405 | 82 |
| 244639 | 3'UTR | 222 | 2920 | ttttcatagtttcacaccat | 47 | 406 | 82 |
| 244643 | 3'UTR | 222 | 2970 | tattttctaagtgaaatagt | 5 | 407 | 82 |
| 244644 | 3'UTR | 222 | 3243 | taggcagcactaggcaggct | 33 | 408 | 82 |
| 244647 | 3'UTR | 222 | 3373 | aggaacaggcctggacagca | 36 | 409 | 82 |
| 244650 | 3'UTR | 222 | 4168 | gagggctataggtcagtaga | 34 | 410 | 82 |
| 244655 | 3'UTR | 222 | 4329 | aagacaccaggacctcaatg | 18 | 411 | 82 |
| 244656 | 3'UTR | 222 | 4532 | ccaatgtactgatgactctc | 62 | 412 | 82 |
| 244660 | 3'UTR | 222 | 4737 | tcacaccacctcactggagc | 62 | 413 | 82 |
| 244663 | 3'UTR | 222 | 4987 | agtaggtcagtattaataac | 35 | 414 | 82 |
| 244667 | 3'UTR | 222 | 5220 | atctcattcaggaagggaaa | 0 | 415 | 82 |
| 244668 | 3'UTR | 222 | 5272 | aaattacacttgggtcacaa | 57 | 416 | 82 |
| 244673 | 3'UTR | 222 | 5326 | caatctcaatcagtacaagt | 37 | 417 | 82 |

As shown in Table 5, SEQ ID NOs 344, 350, 351, 353, 355, 356, 357, 359, 361, 362, 364, 366, 367, 368, 369, 371, 372, 373, 374, 375, 376, 377, 380, 384, 391, 392, 397, 399, 400, 402, 404, 405, 406, 412, 413, 416 exhibited at least 40% inhibition of stearoyl-CoA desaturase in this experiment. A more preferred sequence is SEQ ID NO: 373. The target regions to which these preferred sequences are complementary are herein referred to as "preferred target segments" are therefore preferred for targeting by compounds of the present invention.

Example 19

Effects of Antisense Inhibition of Mouse Stearoyl-CoA Desaturase Expression in Mice: mRNA Levels in Liver and Fat Tissue Ob/ob mice harbor a mutation in the leptin gene. The leptin mutation on a C57B1/6 background yields a db/db phenotype, characterized by, hyperglycemia, obesity, hyperlipidemia, and insulin resistance. However, a mutation in the leptin gene on a different mouse background can produce obesity without diabetes, and these mice are referred to as ob/ob mice. Leptin is a hormone that regulates appetite. Leptin deficiency results in obesity in animals and humans.

In accordance with the present invention, ISIS 185222 (SEQ ID NO: 332) was further investigated for its ability to reduce target levels in liver and fat tissue in ob/ob mice maintained on a high-fat (11% kcal-from fat) or low-fat (2% from fat) diet.

ISIS 141923 (CCTTCCCTGAAGGTTCCTCC, SEQ ID NO: 418) is a scrambled control oligonucleotide. ISIS 141923 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

Eight-week old male ob/ob mice were dosed twice weekly by intraperitoneal injection with saline or 25 mg/kg of ISIS 185222 or ISIS 141923. Mice were maintained on a low-fat or high-fat diet. At the end of the ten-week investigation period, mice were sacrificed and evaluated for stearoyl-CoA desaturase and stearoyl-CoA desaturase-2 mRNA levels in liver and fat tissue. Inhibition of mRNA expression was determined by quantitative real-time PCR as described in other examples herein. The data are the averages of mRNA levels from nine mice per group and are presented in Table 6.

TABLE 6

Antisense inhibition of stearoyl-CoA desaturase in mouse liver and fat tissue

| | | Percent Inhibition | | | | | |
|---|---|---|---|---|---|---|---|
| | | Saline control | | ISIS 185222 | | ISIS 141923 | |
| mRNA | Diet | Liver | Fat | Liver | Fat | Liver | Fat |
| stearoyl-CoA | High-fat | 0 | 0 | 93 | 96 | 29 | 28 |
| desaturase | Low-fat | 0 | 0 | 94 | 98 | 0 | 0 |
| stearoyl-CoA | High-fat | 0 | 0 | 37 | 40 | 52 | 5 |
| desaturase-2 | Low-fat | 0 | 0 | 37 | 0 | 0 | 0 |

The data demonstrate that the oligonucleotide of the present invention can inhibit the expression of stearoyl-CoA desaturase in vivo, in both liver and fat tissues. The data also suggest that antisense inhibition of stearoyl-CoA desaturase can reduce expression of stearoyl-CoA desaturase-2.

Example 20

Effects of Antisense Inhibition of Stearoyl-CoA Desaturase in a Mouse Model of Obesity: Organ Weights and Levels of Serum Cholesterol, Triglyceride and Liver Enzymes In accordance with the present invention, further investigation of the effects antisense inhibition of stearoyl-CoA desaturase was conducted in ob/ob mice. The saline-treated and antisense oligonucleotide-treated ob/ob mice described in Example 19 were also evaluated for body organ weight, levels of serum cholesterol and triglyceride and levels of liver enzymes ALT and AST at the end of the ten-week investigation period. Increased levels of ALT and AST are indicative of impaired liver function. Blood samples were collected and evaluated for cholesterol, triglyceride, ALT and AST levels. White adipose tissue (WAT), spleen and liver were individually weighed. Data are expressed as percent change relative to the saline control for the respective diet. The data represent the average of nine mice per treatment group and are presented in Table 7.

TABLE 7

Effects of antisense inhibtion of stearoyl-CoA desaturase on cholesterol, triglyceride, ALT, AST and organ weight

| | | Percent Change | | | | | | |
|---|---|---|---|---|---|---|---|---|
| | | Liver Enzymes | | | | Organ Weight | | |
| | | ALT | AST | CHOL | TRIG | Liver | Spleen | WAT |
| ISIS 185222 | High-fat | −76 | −72 | −11 | 3 | −8 | 19 | 2 |
| | Low-fat | −60 | −55 | 15 | 29 | −29 | −19 | −4 |
| ISIS 141923 | High-fat | −42 | −39 | −1 | −10 | −4 | 20 | 9 |
| | Low-fat | 45 | 34 | 50 | 70 | 31 | −41 | 27 |

The data demonstrate that, concomitant with reducing target mRNA expression (shown in Example 19), the oligonucleotide of the present invention lowers the levels of the liver enzyme ALT and AST in animals maintained on either a high-fat or low-fat diet, which is indicative of improved liver function. Histologically, mice treated with ISIS 185222 and maintained on a low-fat diet exhibit lowered hepatic fatty degeneration.

Example 21

Effects of Antisense Inhibition of Stearoyl-CoA Desaturase in a Mouse Model of Obesity: Plasma Glucose and Insulin, Body Weight, Food Consumption and Oxygen Consumption In accordance with the present invention, the ob/ob mice described in Example 19 were further evaluated to assess the effects of antisense inhibition of stearoyl-CoA desaturase.

Mice were evaluated for plasma glucose and oxygen consumption following three weeks of treatment. The glucose evaluation was conducted following an overnight fast. The oxygen consumption was determined by measuring metabolic rate (MR) and respiratory quotient (RER) during both light and dark cycles. Plasma glucose and insulin (both in non-fasting mice), food consumption, oxygen consumption and total body weight were measured throughout the ten-week treatment period. Shown in Table 8 are plasma insulin (non-fasting) following five weeks of treatment, food consumption following six weeks of treatment and plasma glucose (non-fasting) and total body weight following seven weeks of treatment. The data are the averages of measurements from seven to nine mice and are expressed as percent change relative to saline control for the respective diet. The data are presented in Table 8.

TABLE 8

Effects of antisense inhibtion of stearoyl-CoA desaturase on body weight, food consumption, insulin, glucose and oxygen consumption

| | | Percent Change | | | | | | | |
|---|---|---|---|---|---|---|---|---|---|
| | | Weight | | | | | | Oxygen consumption | |
| | | Total | Food | Insulin | Glucose | | MR | | RER | |
| | | Body | Consumed | Fed | Fed | Fast | Dark | Light | Dark | Light |
| ISIS 185222 | High-fat | −3 | −10 | −3 | 2 | −3 | 3 | 0 | 0 | 2 |
| | Low-fat | −60 | −55 | 15 | 29 | −29 | 4 | 11 | −6 | 0 |
| ISIS 141923 | High-fat | −42 | −39 | −1 | −10 | −4 | −5 | −5 | 3 | 0 |
| | Low-fat | 45 | 34 | 50 | 70 | 31 | 6 | 5 | 2 | 0 |

The data suggest that body weight and food consumption are lowered by treatment of ob/ob mice with the oligonucleotide of the present invention. Comparison of blood glucose, insulin and oxygen consumption in mice fed the same diet does not reveal any significant changes between saline-treated and antisense oligonucleotide-treated mice.

Example 22

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group, which has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., etal., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.).

Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 23

Design and Screening of Duplexed Antisense Compounds Targeting Stearoyl-CoA Desaturase In accordance with the present invention, a series of nucleic acid duplexes comprising the antisense compounds of the present invention and their complements can be designed to target stearoyl-CoA desaturase. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 419) and having a two-nucleobase overhang of deoxythymidine(dT) would have the following structure:

```
cgagaggcggacgggaccgTT  Antisense    (SEQ ID NO: 420)
|||||||||||||||||||    Strand
TTgcucuccgccugcccuggc  Complement   (SEQ ID NO: 421)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 μL of each strand is combined with 15 μL of a 5× solution of annealing buffer. The final concentration of the buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate stearoyl-CoA desaturase expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 medium containing 12 μg/mL LIPOFECTIN reagent (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 24

Design of Phenotypic Assays and In Vivo Studies for the Use of Stearoyl-CoA Desaturase Inhibitors Phenotypic Assays Once stearoyl-CoA desaturase inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of stearoyl-CoA desaturase in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with stearoyl-CoA desaturase inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the stearoyl-CoA desaturase inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or stearoyl-CoA desaturase inhibitor. Furthermore, to prevent the doctors from being biased in treatments, they are not informed as to whether the medication they are administering is a stearoyl-CoA desaturase inhibitor or a placebo. Using this randomization approach, each volunteer has the same chance of being given either the new treatment or the placebo.

Volunteers receive either the stearoyl-CoA desaturase inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding stearoyl-CoA desaturase or stearoyl-CoA desaturase protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/ great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and stearoyl-CoA desaturase inhibitor treatment. In general, the volunteers treated with placebo have little or no response to treatment, whereas the volunteers treated with the stearoyl-CoA desaturase inhibitor show positive trends in their disease state or condition index at the conclusion of the study.

The invention claimed is:

1. A method for improving liver function in an animal in need thereof comprising administering an effective amount of an antisense oligonucleotide that inhibits stearoyl-CoA desaturase (SCD1) to the animal in need of improved liver function, wherein the antisense oligonucleotide is 8 to 30 nucleobases in length targeted to a nucleic acid molecule encoding human SCD1, and wherein liver function is improved.

2. The method of claim 1, wherein the animal has elevated levels of alanine transaminase (ALT), aspartate transaminase (AST) or both.

3. The method of claim 2, wherein administration of the antisense oligonucleotide reduces ALT levels, AST levels or both levels in the animal.

4. The method of claim 1, wherein the antisense oligonucleotide is 20 nucleobases in length.

5. The method of claim 1, wherein the antisense oligonucleotide is at least 95% complementarity to nucleotides 13-71, 178-247, 482-843, 892-1064, 1597-2233, 2245-2589, 2676-3278, 2980-3054, 3342-3499, 3655-3674, 3707-3790, 3825-3853, 3911-4072, 4132-4224, 4261-4398, 4420-4554, 4645-4677, 4834-4865, or 4892-5100 of SEQ ID NO: 3.

6. The method of claim 5, wherein the antisense oligonucleotide is 100% complementary to SEQ ID NO: 3.

7. The method of claim 1, wherein the antisense oligonucleotide comprises at least one phosphorothioate linkage.

8. The method of claim 1, wherein the antisense oligonucleotide comprises at least one modified sugar moiety.

9. The method of claim 8, wherein the modified sugar moiety is a 2'-O-methoxyethyl sugar moiety.

10. The method of claim 1, wherein the antisense oligonucleotide comprises at least one 5-methylcytosine.

11. The method of claim 1, wherein the antisense oligonucleotide is a chimeric antisense oligonucleotide having a 2'-deoxynucleotide gap segment positioned between 5' and 3' wing segments, wherein each nucleotide of each wing segment comprises a modified sugar moiety.

12. The method of claim 11, wherein the modified sugar moiety is a 2'-methoxyethyl sugar moiety.

13. The method of claim 11, wherein the gap segment is 10 nucleotides in length and each of the wing segments is 5 nucleotides in length.

14. The method of claim 11, wherein the chimeric antisense oligonucleotide consists of 20 linked nucleosides.

15. The method of claim 14, wherein at least one internucleoside linkage is a phosphorothioate internucleoside linkage.

16. The method of claim 11, wherein the chimeric antisense oligonucleotide comprises at least one 5-methylcytosine.

17. The method of claim 1, wherein the antisense oligonucleotide further comprises a pharmaceutically acceptable carrier or diluent.

* * * * *

SEQUENCE LISTING

```
<160> NUMBER OF SEQ ID NOS: 421

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 5221
<212> TYPE: DNA
<213> ORGANISM: Homo sapiens
<220> FEATURE:
<221> NAME/KEY: CDS
<222> LOCATION: (236)...(1315)

<400> SEQUENCE: 3
ataaaagggg gctgaggaaa taccggacac ggtcacccgt tgccagctct agcctttaaa     60
ttcccggctc ggggacctcc acgcaccgcg gctagcgccg acaaccagct agcgtgcaag    120
gcgccgcggc tcagcgcgta ccggcgggct tcgaaaccgc agtcctccgg cgaccccgaa    180
ctccgctccg gagcctcagc cccctggaaa gtgatccgg catccgagag ccaag atg     238
                                                              Met
                                                                1 ccg gcc cac ttg ctg cag gac gat atc tct agc tcc tat acc acc acc     286
Pro Ala His Leu Leu Gln Asp Asp Ile Ser Ser Ser Tyr Thr Thr Thr
            5                  10                  15 acc acc att aca gcg cct ccc tcc agg gtc ctg cag aat gga gga gat     334
Thr Thr Ile Thr Ala Pro Pro Ser Arg Val Leu Gln Asn Gly Gly Asp
        20                  25                  30 aag ttg gag acg atg ccc ctc tac ttg gaa gac gac att cgc cct gat     382
```

```
Lys Leu Glu Thr Met Pro Leu Tyr Leu Glu Asp Asp Ile Arg Pro Asp
 35                  40                  45 ata aaa gat gat ata tat gac ccc acc tac aag gat aag gaa ggc cca       430
Ile Lys Asp Asp Ile Tyr Asp Pro Thr Tyr Lys Asp Lys Glu Gly Pro
 50                  55                  60                  65 agc ccc aag gtt gaa tat gtc tgg aga aac atc atc ctt atg tct ctg       478
Ser Pro Lys Val Glu Tyr Val Trp Arg Asn Ile Ile Leu Met Ser Leu
             70                  75                  80 cta cac ttg gga gcc ctg tat ggg atc act ttg att cct acc tgc aag       526
Leu His Leu Gly Ala Leu Tyr Gly Ile Thr Leu Ile Pro Thr Cys Lys
         85                  90                  95 ttc tac acc tgg ctt tgg ggg gta ttc tac tat ttt gtc agt gcc ctg       574
Phe Tyr Thr Trp Leu Trp Gly Val Phe Tyr Tyr Phe Val Ser Ala Leu
            100                 105                 110 ggc ata aca gca gga gct cat cgt ctg tgg agc cac cgc tct tac aaa       622
Gly Ile Thr Ala Gly Ala His Arg Leu Trp Ser His Arg Ser Tyr Lys
        115                 120                 125 gct cgg ctg ccc cta cgg ctc ttt ctg atc att gcc aac aca atg gca       670
Ala Arg Leu Pro Leu Arg Leu Phe Leu Ile Ile Ala Asn Thr Met Ala
130                 135                 140                 145 ttc cag aat gat gtc tat gaa tgg gct cgt gac cac cgt gcc cac cac       718
Phe Gln Asn Asp Val Tyr Glu Trp Ala Arg Asp His Arg Ala His His
                150                 155                 160 aag ttt tca gaa aca cat gct gat cct cat aat tcc cga cgt ggc ttt       766
Lys Phe Ser Glu Thr His Ala Asp Pro His Asn Ser Arg Arg Gly Phe
            165                 170                 175 ttc ttc tct cac gtg ggt tgg ctg ctt gtg cgc aaa cac cca gct gtc       814
Phe Phe Ser His Val Gly Trp Leu Leu Val Arg Lys His Pro Ala Val
        180                 185                 190 aaa gag aag ggg agt acg cta gac ttg tct gac cta gaa gct gag aaa       862
Lys Glu Lys Gly Ser Thr Leu Asp Leu Ser Asp Leu Glu Ala Glu Lys
195                 200                 205 ctg gtg atg ttc cag agg agg tac tac aaa cct ggc ttg ctg ctg atg       910
Leu Val Met Phe Gln Arg Arg Tyr Tyr Lys Pro Gly Leu Leu Leu Met
210                 215                 220                 225 tgc ttc atc ctg ccc acg ctt gtg ccc tgg tat ttc tgg ggt gaa act       958
Cys Phe Ile Leu Pro Thr Leu Val Pro Trp Tyr Phe Trp Gly Glu Thr
                230                 235                 240 ttt caa aac agt gtg ttc gtt gcc act ttc ttg cga tat gct gtg gtg      1006
Phe Gln Asn Ser Val Phe Val Ala Thr Phe Leu Arg Tyr Ala Val Val
            245                 250                 255 ctt aat gcc acc tgg ctg gtg aac agt gct gcc cac ctc ttc gga tat      1054
Leu Asn Ala Thr Trp Leu Val Asn Ser Ala Ala His Leu Phe Gly Tyr
        260                 265                 270 cgt cct tat gac aag aac att agc ccc cgg gag aat atc ctg gtt tca      1102
Arg Pro Tyr Asp Lys Asn Ile Ser Pro Arg Glu Asn Ile Leu Val Ser
275                 280                 285 ctt gga gct gtg ggt gag ggc ttc cac aac tac cac cac tcc ttt ccc      1150
Leu Gly Ala Val Gly Glu Gly Phe His Asn Tyr His His Ser Phe Pro
290                 295                 300                 305 tat gac tac tct gcc agt gag tac cgc tgg cac atc aac ttc acc aca      1198
Tyr Asp Tyr Ser Ala Ser Glu Tyr Arg Trp His Ile Asn Phe Thr Thr
                310                 315                 320 ttc ttc att gat tgc atg gcc gcc ctc ggt ctg gcc tat gac cgg aag      1246
Phe Phe Ile Asp Cys Met Ala Ala Leu Gly Leu Ala Tyr Asp Arg Lys
            325                 330                 335 aaa gtc tcc aag gcc gcc atc ttg gcc agg att aaa aga acc gga gat      1294
Lys Val Ser Lys Ala Ala Ile Leu Ala Arg Ile Lys Arg Thr Gly Asp
        340                 345                 350 gga aac tac aag agt ggc tga gtttggggtc cctcaggttt ccttttcaa          1345
```

Gly Asn Tyr Lys Ser Gly  *
   355

| | | | | | |
|---|---|---|---|---|---|
| aaaccagcca | ggcagaggtt | ttaatgtctg | tttattaact | actgaataat | gctaccagga | 1405 |
| tgctaaagat | gatgatgtta | acccattcca | gtacagtatt | cttttaaaat | tcaaaagtat | 1465 |
| tgaaagccaa | caactctgcc | tttatgatgc | taagctgata | ttatttcttc | tcttatcctc | 1525 |
| tctctcttct | aggcccattg | tcctcctttt | cactttattg | ctatcgccct | cctttccctt | 1585 |
| attgcctccc | aggcaagcag | ctggtcagtc | tttgctcagt | gtccagcttc | caaagcctag | 1645 |
| acaacctttc | tgtagcctaa | aacgaatggt | ctttgctcca | gataactctc | tttccttgag | 1705 |
| ctgttgtgag | ctttgaagta | ggtggcttga | gctagagata | aaacagaatc | ttctgggtag | 1765 |
| tccctgttg | attatcttca | gcccaggctt | ttgctagatg | gaatggaaaa | gcaacttcat | 1825 |
| ttgacacaaa | gcttctaaag | caggtaaatt | gtcggggag | agagttagca | tgtatgaatg | 1885 |
| taaggatgag | ggaagcgaag | caagaggaac | ctctcgccat | gatcagacat | acagctgcct | 1945 |
| acctaatgag | gacttcaagc | cccaccacat | agcatgcttc | ctttctctcc | tggctcgggg | 2005 |
| taaaaagtgg | ctgcggtgtt | tggcaatgct | aattcaatgc | cgcaacatat | agttgaggcc | 2065 |
| gaggataaag | aaaagacatt | ttaagtttgt | agtaaaagtg | gtctctgctg | gggaagggtt | 2125 |
| ttcttttctt | tttttcttta | ataacaagga | gatttcttag | ttcatatatc | aagaagtctt | 2185 |
| gaagttgggt | gtttccagaa | ttggtaaaaa | cagcagctca | tggaattttg | agtattccat | 2245 |
| gagctgctca | ttacagttct | ttcctctttc | tgctctgcca | tcttcaggat | attggttctt | 2305 |
| cccctcatag | taataagatg | gctgtggcat | ttccaaacat | ccaaaaaaag | ggaaggattt | 2365 |
| aaggaggtga | agtcgggtca | aaaataaaat | atatatacat | atatacattg | cttagaacgt | 2425 |
| taaactatta | gagtatttcc | cttccaaaga | gggatgtttg | gaaaaaactc | tgaaggagag | 2485 |
| gaggaattag | ttgggatgcc | aatttcctct | ccactgctgg | acatgagatg | gagaggctga | 2545 |
| gggacaggat | ctataggcag | cttctaagag | cgaacttcac | ataggaaggg | atctgagaac | 2605 |
| acgttgccag | gggcttgaga | aggttactga | gtgagttatt | gggagtctta | ataaaataaa | 2665 |
| ctagatatta | ggtccattca | ttaattagtt | ccagtttctc | cttgaaatga | gtaaaaacta | 2725 |
| gaaggcttct | ctccacagtg | ttgtgcccct | tcactcattt | tttttgagg | agaaggggt | 2785 |
| ctctgttaac | atctagccta | aagtatacaa | ctgcctgggg | ggcagggtta | ggaatctctt | 2845 |
| cactaccctg | attcttgatt | cctggctcta | ccctgtctgt | cccttttctt | tgaccagatc | 2905 |
| tttctcttcc | ctgaacgttt | tcttctttcc | ctggacaggc | agcctccttt | gtgtgtattc | 2965 |
| agaggcagtg | atgacttgct | gtccaggcag | ctccctcctg | cacacagaat | gctcagggtc | 3025 |
| actgaaccac | tgcttctctt | ttgaaagtag | agctagctgc | cactttcacg | tggcctccgc | 3085 |
| agtgtctcca | cctacacccc | tgtgctcccc | tgccacactg | atggctcaag | acaaggctgg | 3145 |
| caaaccctcc | cagaaacatc | tctggcccag | aaagcctctc | tctccctccc | tctctcatga | 3205 |
| ggcacagcca | agccaagcgc | tcatgttgag | ccagtgggcc | agcacagag | caaagaggg | 3265 |
| tttattttca | gtcccctctc | tctgggtcag | aaccagaggg | catgctgaat | gccccctgct | 3325 |
| tacttggtga | gggtgccccg | cctgagtcag | tgctctcagc | tggcagtgca | atgcttgtag | 3385 |
| aagtaggagg | aaacagttct | cactgggaag | aagcaagggc | aagaacccaa | gtgcctcacc | 3445 |
| tcgaaaggag | gccctgttcc | ctggagtcag | ggtgaactgc | aaagctttgg | ctgagacctg | 3505 |
| ggatttgaga | taccacaaac | cctgctgaac | acagtgtctg | ttcagcaaac | taaccagcat | 3565 |
| tccctacagc | ctagggcaga | caatagtata | gaagtctgga | aaaaacaaa | aacagaattt | 3625 |
| gagaaccttg | gaccactcct | gtccctgtag | ctcagtcatc | aaagcagaag | tctggctttg | 3685 |

```
ctctattaag attggaaatg tacactacca aacactcagt ccactgttga gccccagtgc    3745
tggaagggag gaaggccttt cttctgtgtt aattgcgtag aggctacagg ggttagcctg    3805
gactaaaggc atccttgtct tttgagctat tcacctcagt agaaaaggat ctaagggaag    3865
atcactgtag tttagttctg ttgacctgtg cacctacccc ttggaaatgt ctgctggtat    3925
ttctaattcc acaggtcatc agatgcctgc ttgataatat ataaacaata aaaacaactt    3985
tcacttcttc ctattgtaat cgtgtgccat ggatctgatc tgtaccatga ccctacataa    4045
ggctggatgg cacctcaggc tgagggcccc aatgtatgtg tggctgtggg tgtgggtggg    4105
agtgtgtctg ctgagtaagg aacacgattt tcaagattct aaagctcaat tcaagtgaca    4165
cattaatgat aaactcagat ctgatcaaga gtccggattt ctaacagtcc ctgctttggg    4225
gggtgtgctg acaacttagc tcaggtgcct tacatctttt ctaatcacag tgttgcatat    4285
gagcctgccc tcactccctc tgcagaatcc ctttgcacct gagacccytac tgaagtggct    4345 ggtagaaaaa ggggcctgag tggaggatta tcagtatcac gatttgcagg attcccttct    4405
gggcttcatt ctggaaactt ttgttagggc tgcttttctt aagtgcccac atttgatgga    4465
gggtggaaat aatttgaatg tatttgattt ataagttttt tttttttttt gggttaaaag    4525
atggttgtag catttaaaat ggaaaatttt ctccttggtt tgctagtatc ttgggtgtat    4585
tctctgtaag tgtagctcaa ataggtcatc atgaaaggtt aaaaaagcga ggtggccatg    4645
ttatgctggt ggttaaggcc agggcctctc caaccactgt gccactgact tgctgtgtga    4705
ccctgggcaa gtcacttaac tataaggtgc ctcagttttc cttctgttaa atggggata    4765 ataatactga cctacctcaa agggcagttt tgaggcatga ctaatgcttt ttagaaagca    4825
ttttgggatc cttcagcaca ggaattctca agacctgagt attttttata ataggaatgt    4885
ccaccatgaa cttgatacgt ccgtgtgtcc cagatgctgt cattagtcta tatggttctc    4945
caagaaactg aatgaatcca ttggagaagc ggtggataac tagccagaca aaatttgaga    5005
atacataaac aacgcattgc cacggaaaca tacagaggat gccttttctg tgattgggtg    5065
ggattttttc cctttttatg tgggatatag tagttacttg tgacaaaaat aattttggaa    5125
taatttctat taatatcaac tctgaagcta attgtactaa tctgagattg tgtttgttca    5185
taataaaagt gaagtgaatc taaaaaaaaa aaaaaa                              5221
```

<210> SEQ ID NO 4
<211> LENGTH: 17
<212> TYPE: DNA
<213> ORGANISM: Artificial Sequence
<220> FEATURE:
<223> OTHER INFORMATION: PCR Primer
<400> SEQUENCE: 4
gatcccggca tccgaga                                                   17

<210> SEQ ID NO 5
<211> LENGTH: 27
<212> TYPE: DNA
<213> ORGANISM: Artificial Sequence
<220> FEATURE:
<223> OTHER INFORMATION: PCR Primer
<400> SEQUENCE: 5
ggtataggag ctagagatat cgtcctg                                        27

<210> SEQ ID NO 6
<211> LENGTH: 21

```
<212> TYPE: DNA
<213> ORGANISM: Artificial Sequence
<220> FEATURE:
<223> OTHER INFORMATION: PCR Probe

<400> SEQUENCE: 6
ccaagatgcc ggcccacttg c                                              21

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
gtccggtatt tcctcagccc                                                20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
ccgcggtgcg tggaggtccc                                                20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
tacgcgctga gccgcggcgc                                                20
```

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
gcggtttcga agcccgccgg                                               20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
cctccattct gcaggaccct                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
tcccaagtgt agcagagaca                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
ctcctgctgt tatgcccagg                                               20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
cacggtggtc acgagcccat                                               20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cagccaaccc acgtgagaga                                               20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gacaagtcta gcgtactccc                                        20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttcaccagc caggtggcat                                        20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tgtggaagcc ctcacccaca                                        20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
agttgatgtg ccagcggtac                                        20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ggaccccaaa ctcagccact                                        20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tgcctgggag gcaataaggg                                        20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
atacatgcta actctctccc                                        20

<210> SEQ ID NO 26
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 26
aagtcctcat taggtaggca                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tgtaatgagc agctcatgga                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcagtaacct tctcaagccc                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggagctgcct ggacagcaag                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tcagtgaccc tgagcattct                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tggctggccc actggctcaa                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gcatgccctc tggttctgac                                               20
```

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gctttgcagt tcaccctgac                                          20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gtggtatctc aaatcccagg                                          20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tagtccaggc taaccctgt                                           20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gtgatcttcc cttagatcct                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ctcagcagac acactcccac                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gctaagttgt cagcacaccc                                          20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 39
aagtttccag aatgaagccc                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
agagaataca cccaagatac                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tagttaagtg acttgcccag                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gccctttgag gtaggtcagt                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ccatatagac taatgacagc                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ctgtatgttt ccgtggcaat                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cttgcacgct agctggttgt                                               20

<210> SEQ ID NO 46
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 46
gcatcgtctc caacttatct                                                    20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
taaggatgat gtttctccag                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
cccaaagcca ggtgtagaac                                                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tgtaagagcg gtggctccac                                                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
cattctggaa tgccattgtg                                                    20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ttatgaggat cagcatgtgt                                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cctctggaac atcaccagtt                                                    20
```

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
ggatgaagca catcagcagc					20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ttcaccccag aaataccagg					20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
gaaaccagga tattctcccg					20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tcactggcag agtagtcata					20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
taatcctggc caagatggcg					20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tcatcatctt tagcatcctg					20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 59
gcaaagactg accagctgct                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gactacccag aagattctgt                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cttccctcat ccttacattc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cccgagccag gagagaaagg                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cttccccagc agagaccact                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ccaatatcct gaagatggca                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cccaactaat tcctcctctc                                              20

<210> SEQ ID NO 66
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 66
tatagatcct gtccctcagc                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ctcccaataa ctcactcagt                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
aagagattcc taaccctgcc                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
cacacaaagg aggctgcctg                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
aagtggcagc tagctctact                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
caccctcacc aagtaagcag                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tgcttcttcc cagtgagaac                                               20
```

-continued

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
atcaagcagg catctgatga                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ccctcagcct gaggtgccat                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ataatcctcc actcaggccc                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cacttaagaa aagcagccct                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
cagcaagtca gtggcacagt                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ggctagttat ccaccgcttc                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 79
cccaatcaca gaaaaggcat                                                       20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
aactactata tcccacataa                                                       20

<210> SEQ ID NO 81
<211> LENGTH: 18508
<212> TYPE: DNA
<213> ORGANISM: H. sapiens

<400> SEQUENCE: 81
gagatgttag tggtgggcgc ccccgaggg ttcaccactg tttcctgaga aacttcccca            60
gtgcccaccc acccgttctc cgtgtgcccg agggccggtc ctgggctagg ctccgcgccc          120
cagccccaaa ccgggtcccc agcccttcc agagagaaag ctcccgacgc gggatgccgg           180
gcagaggccc agcggcgggt ggaagagaag ctgagaagga gaaacagagg ggaggggag            240
cgaggagctg gcggcagagg gaacagcaga ttgcgccgag ccaatggcaa cggcaggacg          300
aggtggcacc aaattccctt cggccaatga cgagccggaa tttacagaag cctcattagc          360
atttccccag aggcaggggc aggggcagag gccgggtggt gtggtgtcgg tgtcggcagc          420
atccccggcg ccctgctgcg gtcgccgcga gcctcggcct ctgtctcctc cccctcccgc          480
ccttacctcc acgcgggacc gcccgcgcca gtcaactcct cgcactttgc ccctgcttgg          540
cagcggataa aagggggctg aggaaatacc ggacacggtc acccgttgcc agctctagcc          600
tttaaattcc cggctcgggg acctccacgc accgcggcta gcgccgacaa ccagctagcg          660
tgcaaggcgc cgcggctcag cgcgtaccgg cgggcttcga aaccgcagtc ctccggcgac          720
cccgaactcc gctccggagc ctcagccccc tggaaagtga tccggcatc cgagagccaa           780
gatgccggcc cacttgctgc aggacgatgt gagtttccca gcctggcccc gtaccgccgg          840
gtcgcaggcg cgggctgggc ttccagggga cgggttggtg gcagaagaga ggggagagct          900
ccgcggagga cttggtcatc ttttcgagt tgtgctgcct tccgtgagtt gggaatgtgg           960
attgtaattt ggggacttga gtctccaact ttagtttctt aagctttaaa gaaaaatccg         1020
gtcgtgctgg tgcttttatg aattatgcgg ttttcctttt gtcttcgtgg ggatgtgagt         1080
gctttacttc tccttcctac tgccgcctcc cgataggttt cgcgcccctc gtcccctcg          1140
ccctccgccc ctaatgtatc tgtacagttt cagggaactt ttctccgttg cgtctcggat         1200
acaccctacc ctcagtgaac tacggcgctg cggaagggtc cgtactgtcc acccttcccc         1260
cagcgtgatt agagagcgga gtggcccag ctgcctccac gtgtctcttc tcctgactct          1320
cctcttcctc cccccttccag atctctagct cctataccac caccaccacc attacagcgc        1380
ctccctccag ggtcctgcag aatggaggag ataagttgga gacgatgccc ctctacttgg         1440
aagacgacat tcgccctgat ataaaagatg atatatatga ccccacctac aaggataagg         1500
aaggcccaag ccccaaggtt gaatatgtct ggagaaacat catccttatg tctctgctac         1560
acttgggagc cctgtatggg atcactttga ttcctacctg caagttctac acctggcttt         1620
ggggtaagca gcctccctgt cctcctgacc tagtcctcca ggtactcact gctcttttaa         1680
```

```
taaggtagga tcttacagag gacaccagcc cctcccagcc tcccggttgg ggttttctc    1740 aggcatttct ctttggttgc ttcaggccta gtgggctggg aagaacctgg gggtactgag    1800
atgcaggact gtcaatgctg ggggttgaga gctttggaac cttgtgcttg tgggctttga    1860
agtgtgctgt gctggagagt cagctttccc tgaaagagct tttctgtttg agtcatttgc    1920
ttggctgcct gtcccacccc tgccagccac aaaagaatca aaccctcta cctgggaggc    1980 atgggaacat ggtactaaac cattggcttt ctagggtttg tgttgagcaa tcataggcta    2040
gcacaaggga aactactcag ggagagagtt tattggaaag ggaggagaga gctcattgga    2100
aagagaggaa aagagaggtt gttatccaca aaactatttt gacctgaccc cttggccaga    2160
ccaggcttct tcgttacaga ggaagatgaa gctcccgtgc aacccaagtc acacaggtgt    2220
gtgttgctct gttactctac attccagggt gctgcacata ccagtcaaca aaatgctctt    2280
agaatgaaat caggctgaag atatgtttca tgttccatcc cccgtccagc ctgcttcagg    2340 ccccccctact gatgccatga agtgccaaga attctgcacc ttccaacacc agtcctaccc    2400
atccctcctt gccagggaca tcgaggccag gccagaaaag agagcccggt cttgaggctg    2460
ctgtaatgag ggagacagtt cccagtttgt ccccgacctg cccttagctc agctctttca    2520
gggacctgtt ggtgtggcct gatggcatgg ccctgccccc tggatacaca catgcgcttt    2580
gcaggctttt tcacctctgt cactatgagc ctaagttggg aagggaaagc agggagctct    2640
gcagatccag ggccctgca ctgctactct ctaaggggtg gtgagccagg acttctggtg    2700
tgggaaactt tctgacagct cgctcttgaa gggtagttat gcagaagggc tggtaggcca    2760
agttttagct gtttccctca ggacctctta ggtcttctga agatggtgag atctggttca    2820
ttgagctttt gtttccagaa atcctccagg tgctacagtg aaatgcaact gagaagagcc    2880
cctttgtcag gatctcagtt tttctaggta ccacctgtgg gcaacagtac ttttttagga    2940
tggggaaggt agcattcctt gggttacata tgtgtcacag ccgcagagac agaacaggcc    3000
aggtgcagat cagttcatct gcataccagg aagagctctt gtatttgtga ggggagggcg    3060
acatctgttg tctagcccct ctgaggatcc agcagaactt cagttgcagc tgagggatga    3120
ggagcaggga tagcattccc caggcagtct gtggatgcct ctctccaccc tttctcccca    3180
agaggatagt cttcacaagt agttttctct cctgcaagct ccttccagcc tcagcacccc    3240
ctgtaggttt cctgaagccc agagtttgac ccgattgcct ctgcttggtt atcctcagtt    3300
gctactgcaa ggagcagaat tccatcccaa agtgaaggct gtgcctgcta cattttttg    3360 gtgacctgcc catgggtgtg tgctgtgccc ttgggcagat aaatgtggct cacagagact    3420
agatggtaac ttattttact gggccctttg gtggatggct tagctgaaag aatgaccatg    3480
tcgatgtggg gatatcagaa ctcctctgtc ttgagaaaca aggagggtga ggggaggagg    3540
gtcagaggtc tcaacttgga catcttctct tcccaccttc agaatttagg agcttcacct    3600
ttcttgtttt aatccctatg gacaatgtta aattagcaac tggtcgtgat ccagcatttt    3660
cttatgactg agcactttg agagccttaa atctctttca ttttggagtc tcccaaagaa    3720
gcccttagga gaatgcctct ggcaacactg agagccagag gcaaaccatt caagtctct    3780 ttcttaaggc cagagcaatg agatgttgct taaccatcaa tctggacatt ttcctcccct    3840
ggggaggaga gaaggaataa atctccaact gatttaagcc cttctatttg ataggcttag    3900
aggtgtttct agaaaaggca ccagagtgcc tgagttcttt ccccaatttc cctgttaata    3960
taggatctta tatacgttct gagtcaacac tgccctaggg tcttgcagca aataacaacc    4020
ctagaagctc ccttgctcat tagagagagc tctggctcaa ctgatggttt cccgagtaag    4080
```

```
atgcaggtag atactgtatc tggggagatg tcagtcacca cttggcttga gggcagatca    4140 cctgggcct  cagtccccac tctgagggaa tgtggagaga gctcttgttg gggctgactg    4200
gctctgtggc tctcctggag atcttatagg aggaatagaa gagaagaaag gaggtagggt    4260 tgggggaaa  aggaggttgt ttaggaaaca gctatcaatg gctgcaaaag aacacaggac    4320
aatttgttac aatgtgtggt gtctccaact gcaactaagt tctgtggcca ctgaggatct    4380
attgtttcta gctgtttccc taggaatgaa acattgttaa gagtttctat caaggccaca    4440
gcttctgcct gctagagcta ctgaacagag gaagatatgg ggacgcccag cagcccactt    4500
cccagttaga gattatatct ggcacctcct gagcctgcag gcctccagga aggtgaggga    4560
agacaatggt ggggtgcttc actgacagct tgaagaatat cccaccattg tctagagagc    4620
gttgcccggt gagagtatgg gctgacaggg atgtggcaaa ggcgagacag aggagttgtg    4680
catgtatctt gggggaggtg gatggtatag ctggaacgtg aaatctttgg taaagcttaa    4740
gacactgtac aaattggatt tatgcacagg gctaattttt ccctgatttg ccacactga     4800 ctgcttgaat attaaatgc  ttttttgtac cagttgataa atggccatag tctgaatgcc    4860
ctaagagtcc cctacaacta agggcttctc aaattggtca gtgcccagat tgtactggct    4920
gttattttat ttttgagat  aaggtcttgc tgtgttgata aggcttgagt gcagtggcgc    4980
gatcttggct caccgcagcc tcgacctcct gagctcaaga gatcctccca cctcaacctc    5040
ttgagtagct gagaccacag gcaggtgcca ccatgccaag ctaattttta aaattatctg    5100
tagaggcaag gtctccctat gttatcccag ctggtcttga actcctgggc tcaagggat    5160 cttcctgcct tggcctccca aaatgctggg atgacaaagt ggttcatact acacctggcc    5220
ctctgctgtt attttaataa caccctggct tatgggttct gagctctgca ggagtagttt    5280
gtggccctta aaaccttaga gaaggcctag atagaggtga aggagatag  ctaggccctg    5340 ggagaatgcc tttaagatga agaatgagtg gtaagagcac tattctctct cctgcctttc    5400
tgactcctta gttcctggga ttctttagct tatctttttt tcctgggttg agaggttggg    5460
gggtgatatt tttcaagtgg taaaatctaa gggatgtggt tatccctaga gttcatggta    5520
aagccagttc tcacccaaag cctgacgaag acagtttcta gcatccagag agtgtctctg    5580
gcatcctttc ccagatggaa ctcacactga ttggtgactc ccccactgtc ttctcctggc    5640
aggggtattc tactattttg tcagtgccct gggcataaca gcaggagctc atcgtctgtg    5700
gagccaccgc tcttacaaag ctcggctgcc cctacggctc tttctgatca ttgccaacac    5760
aatggcattc caggtaagaa gttgtctctg ctcagctgtt tgtcctccac actattaatg    5820
atccggggac agaaaggagg gatcagcacc agagaggagc cacacctgac agccatttca    5880
ctttcctctc tcctgtagtc acctcaagtt ccagttcagt ccttaagtcc ataaagcatg    5940
aagagacttc tgagtcttgg aaaagggaac tggaagataa ttggaaaata ctcctgatgt    6000
gtaggaatat ttttgatcct aaggtccctg tgttgtcaca caatctggcc gttgtggctc    6060
ttcatcataa ggggctttgg cacataagcc agagactgac cttagattcc tgggcagaca    6120
ctggacaata aattcactat ttaaggtaaa tatcttaggg aggcagagct gggaggatca    6180
ctggagccca ggagtttgaa gctgcagtga gccatgatat caccactgca ctccagcctg    6240
ggtgacaaga cccccaacttt aaaaaaaaaa tttcaaaagt gaataactta ggactccacc    6300
acagtgggat tgaagttgat gttcccagac tcgtgaactc ttattttgag ataatgagag    6360
caaacacttt tattgcactg actatgagcc tggcactatt ctaagcattt gatataaagt    6420
cctcacaaaa atcttaggaa ataggtacta ttatccccat tttacagatg aggaaaccaa    6480
```

```
gttacagaga gattagatag accagcccaa cattgtggcc ctttcttggg ctgccatggt   6540
ggctaagtaa aacattgagg tttgttaagg caaaaaacaa acctgggcac ggtggctcac   6600
gcctgtaatc tcagaacttt ggaggccga ggtgggcaga tcacaaggtc aggagatcaa    6660
gatcatcctg gctaacacag tgaaactctg tctctactaa aaatacaaaa aattagccag   6720
gcgtggtggc gggcacctgt agtcccagct acgtgggagg ctgaggcagg agaatggtgt   6780
gaacctggga ggcagagctt gcagtgagct gagatcgcgc cactgcactc cagcctgggc   6840
aacagcaaga ctccatctca aaaaaaaaa aaaaaagtt tatagcaaag acagaatgaa     6900
gggaaatggg gaagggaat gcatcatagt cattaagctg tagcaatggg caaatgatag    6960
catgtggcgt ttggcttagc ttggagcaag aggaagaaag gaaaccaact tagtggtggc   7020
aatatcccaa gaacttgcca catttgcatg atcatctctg ccatagcagc ttataccttg   7080
aaggcttcca aagttgtcct gtggagcaaa aggaaggaag agagatattg gtacattctt   7140
taagggatgg aaaaagtcat gaagaagccc agaggtcgtt tgaaaatgca gtcatgatca   7200
cgagttgcat gcctggcctt gttattgggt tgtatgagct cttttgcaag gcaccagaat   7260
ggtgcaccct gcagctgcag cttatctact gattgagacc ctaggacaca aggctgcctg   7320
cctcatgttc cccatgccta gggattaggt accccatgag gatcttttcc aacattcctt   7380
gcttaaagaa ttgcaatgtt ctcacttctt gaaactctct gagctctgta tgatttacct   7440
ccgttccacc caccatataa ctttcaagaa acagcagttc tattgctatg gtcctgggac   7500
tttaagttgc ttttttctac ttaagcttca gtggcaagtt gggagaagaa gggaggcaac   7560
tccatgactc ctttggagcc cagattcctg ggtattttgt gaggttgggc tgagcgcctt   7620
gggctcttga tacctgtcca ttgggattct cctaataggg tgtctatcct caagccttac   7680
attcctcttc tctctctccc cagaatgatg tctatgaatg ggctcgtgac caccgtgccc   7740
accacaagtt ttcagaaaca catgctgatc ctcataattc ccgacgtggc ttttttcttct  7800
ctcacgtggg ttggctgctt gtgcgcaaac acccagctgt caaagagaag gggagtacgc   7860
tagacttgtc tgacctagaa gctgagaaac tggtgatgtt ccagaggagg tgagtgaagc   7920
cctgatggag gtggggatat ggccctggca cctggtcatt agggacccca ttttttctcc   7980
tgagactttc aaaatataag ctgagaaatt tgctgggttt gcatgttcac aatcttaatt   8040
taaaatccca atttttaaca tcccacgggc ccgtagccat agactattgc tccatttctt   8100
tctctctgac tatcttaatt aaacccatta cattcaagag atgttttattg tcctaggaca  8160
gtcatagatt caaagatgat tatagcctag ttgcctaggt ttgtttgttt gttttttgtgt  8220
ttgtgtttca acagtctttc tctcttgccc aggctggagt gcagtggcac aatcatggct   8280
cactgcagcc ttgacttccc aggctcaagc aatccttcta cctcaacctc ctgagtatct   8340
gggactacag gcacacaccg ccatgcctgg ctaattttttt gtggggacaa ggtctcactc   8400
actatattgc ccaggccggt agcttagttc ttaccttcaa aaagtttgta gcctatcggg   8460
gtggagagat aagccaagta tccagataac catggcataa ggcagaatat tttctgtact   8520
atgagaggta caaggggag ggagattgct caatgggcaa caccaaggaa gtgatatgaa    8580
ataaatagtg ttggaatcca ccaacggata gaaatttta caactatgtg tggggagaga    8640
cagtgcaaac agaagaaaca gaatgagcta aaacacgaag catgttccag caatagagtc   8700
cttttgcttg aagtataggg tatgggaaga agtaagactg gagagactaa tgccattctt   8760
gtcgagtcct aaaagcagac ttaggactta attcaataag caataggaag ccattacatc   8820
ttttgaactg caatgtggca tagttacgga cgtgctttag gaaggctgct tttagaacaa   8880
```

```
gtgtaagaaa ccactgagcc aaagtgagag gtagggacat aagttaggta atgaggaccc      8940
ctgctagcga agcagtggca gaaatggaga aaagagttgg gtgcagggaa tgtcagtgat      9000
gtaaaagtca aagacttgac tgctgaagga atgtagggaa tcagtgccct tggaatgtca      9060
atggcctggt ctacattgag aatgaagact gagaaagggc ttcctgaggg acagagagct      9120
gcaggtgatc aaggacactc aatgggtctc tgagggaaaa gaagaccaaa gaattaggga      9180
gtagctagca gaaaatggag gcatgacact aaacacagac tgaaaagag tgctgattag       9240 aaagagaaag gagcccaaag gcagatggga aaaccagcca aggatggaga gacgtctgtt      9300
cattagtttg tagtttggac ctcacctatc ttaccaatgt ggtattatgc tctagtaaaa      9360
agtcagcgat ggccgggcat ggtggctcat gcccgtaatc ccagcacttt gggaggctga      9420
ggcgggagga ttgctggaaa gttcaggcat tcgagaccag cctgggcaac atagtgagac      9480
ctcatctcta caaaaaatta aaaactaaat gggcacgatg gttcatgcct gtggtcccag      9540
ctactcagga ggctggggtg ggaggatctc ttggcccagg agttcaaggc tgtggtgaac      9600
taaggtcacg ccactgcact ccagccttgg caacagagtg agaccctgtc aaaaaaaaca      9660
aacaaaaata aataaaacaa tgaacttaga gtcagacaag caattcaaca tggaagaaag      9720
acagcccatc ccctcccaat tagtgtggaa gatccatgta ggtgtggagt cccctccat      9780 tgacctggtg tctggtctgt caatgtaggt actacaaacc tggcttgctg atgatgtgct      9840
tcatcctgcc cacgcttgtg ccctggtatt ctggggtga aacttttcaa aacagtgtgt       9900
tcgttgccac tttcttgcga tatgctgtgg tgcttaatgc cacctggctg gtgaacagtg      9960
ctgcccacct cttcggatat cgtccttatg acaagaacat tagcccccgg gagaatatcc     10020
tggtttcact tggagctgtg ggtaagtcag ctgtccaagt aagactacat ccagtggtct     10080
gctgattagg ggattaggct aggagccaga aaaactagat aaatctgttt tttatggcta     10140 cttttgtatct cagttttttcc actataaaat taggggggcag tatactggaa aacgcttttg    10200
agagtcaggc aacatgtttt atgtaaaaat gaaaggataa gaaacaaaac acaaaaaaac     10260
actgattttg attccaggtt ctaaaacaat ttccaaatgc catgtatgct ccgggcccgg     10320
cggctcatgc ctgtaatccc agcactttgg gaggctgagg cgggcaggtc acctgaggtc     10380
aggagtttga gaccagtctg gccaacacgg tgaaaccctg tttctattaa aaagcaaaac     10440
aaacaaacaa aaagaaaac caaatgccat acatgatgag caccttagag tttttccttc      10500
tttcatcaac tctgggctgg actgcagtct tgcttgaggc aaggaatgca taaatagaac     10560
aatgggatca tctgagtggc cagtaagcct ggtgttttat gaacttcaag tatgcacaca     10620
aagtattttt tatctttcca ctctactcag atatgccttg ctttaagagt gtgccgtgcc     10680
ttactgtttg gtgatgccat tatgaagggc atcaaaataa ctgctggtgg ccctttacta     10740
ccacctaccc tcttgtctcc tcttgtcctc tatttttctc tcttctactt ctattctggg     10800
ctaggaacat cccttccccc aacatgcctt caggaatctc ccaataaagc agtgtgatca     10860
caagttcctg ctcaattctc taatgttgat cttatctttt ctcttttctt tcctttcatt     10920
ttctttcttt tcttttcttt tccttttctt tctaatgaga cagggtctca ccatggtgcc     10980
caggctggtc ttgaaccctg ggctgaagtg atcctcctgc ctcagcctcc caaagtatct     11040
acattttttt ctctgtccct cttccaact gaatatagac tttcaccaag gccctgaatg      11100
aattttcctt aaatagatct ggcgacctct tcttttccagt aattggtgct attggtcatt    11160
caataatatc tagacaacca cactactcca cacatttagg caggtcattg cctaacactc     11220
attttctttt tctctttaaa aatcttcctt tatattctca accttaacca tctttattat     11280
```

```
cttttaaatt gttgttgaga cagtctcact ctgttgccca ggtttcagtg cagtggtgtg   11340
atcacagctc actgcagcta tgacctcctg ggctcaagcg atcctcgggg ttcagcctcc   11400
caagtaactg ggattacagg tgcatgccac catgcttggc taattttctt attttttgt    11460 agagacatgg ttttgccatg ttgcacaggc tggtctcgaa ctcctgagct caagtgatct   11520
tcctgccttg gcctcccaaa gtgctggaat tataatagcc gtgagccact gcgcctggcc   11580
tactatgttt attaaaagga tttattgcct gtaatcccag cactttggga ggccgaggcg   11640
ggtggatcat gaggtcagga gatcgagacc atcctggcta acaaggtgaa accccgtctc   11700
tactaaaaat acaaaaaaat tagccaggcg cagtggcggg cgcctgtagt cccagctact   11760
tgggaggctg aggcaggaga atggcgtgaa cccgggaagc ggagcttgca gtgagccgag   11820
attccgccac tgcagtccgc agtccggcct gggcgacaga gcgagactcc gtctcaaaaa   11880
aaaaaaaaaa aaaagattta tttgtctagg cgtggtggct cacacctgta atcccagcac   11940
tttgggaagc caaagtgggt ggttcacttg aggtcaggag ttagagatca gccaggccaa   12000
tatggtgaac ctctgtctct acttaaaaaa aaaaaaaaa aaagtacaa aaaacttagc     12060 caggcatggt ggcacgtgcc tgtagtccca gctactcagg aggctgaggc agaagaatcg   12120
cttgaacccg ggaggcagag gttgcaatga gccgagattg tgccactgca ctccagcctg   12180
ggtgacagag actccatctc aaaaatatat aataaaaata aaagcatttt ttttctctct   12240
ttttaacttt cacatatctc ttttcaggca ccttcttacc attgtgccta ttcttacttt   12300
aacccatgat taaaataaat catatacact gtataaatct gagattatca taggaatgga   12360
gtttctggca tgagatgttt cctgtatcgc aaatggatct ataatgacct tccccacctc   12420
cagcctctgg gtggccatga gttcaaagtg gctgccaata tctgacctgt tgttgttatc   12480
attcactcct ccttgcctgc tgctttcctc ccttatcacc tcaccctttg ttctcctcca   12540
gctctgtttc ctgccaccct aatctttttg tttcttgaat tacctccccc actgtcacat   12600
gctcatcttc tctgccaaat taaccttctc ccttgagcct ttcttgggct gtctcttgct   12660
gccccagttg caaagtcctg tcttcttttct acccgttgac cctcttcttt tttttttcctc  12720 ccttgtctct gtgtgcatct gattccattt taaatctggt aaccaaaggc ctggctagtg   12780
cttacacaca gcccagctgc aaaaccatta atggacatta ataatcctca gtacctttat   12840
tcctggcatt ctaccccct cctccccagt tcacactgca gatcatcagg tgtcacagag    12900
agaggacata ccttgaaatg ccctagatga tgtcatttac tttgcaggac ttccttgcct   12960
tgcttctgat taatgtcatg actggtctgt ctgagggtac tgttatctac aaagagccaa   13020
atattagctc ttagtagcta ttctttatcc atgcctgatt agggtcagta ttattttgg    13080 ctgtggttca gaaagaagag tcctgccaag cgttggcaaa ctctctatct gtcgagtttc   13140
caaagcttta cacgttagag aaattgctgt gaatccagaa tttgtttgtt ttcctcccctc   13200 cagcaaagtg aaatgttcat cccaagagtc ctcaaaatct cagaggttac agggtatttt   13260
tcttcctcag agagcttctg ttttatcagc acctccccca caccagggtc aaagctcaaa   13320
aaagttggag cagcccctgg gaactgcagt ggctgaggac attccagccc ctgggctggc   13380
ctttcttctg atcttttggct gcagggccca ctcttttgga acctcccacc cctagaggtg   13440
gttccagtgt ggtgggggaaa ggtgtgcttc tttactcatt tttttaagag tcatagccag   13500
agtgcttcat tctgcaagga cgtgcacatg cacatgcaca cagagccttg agggcagggc   13560
caagagtgaa tttggaattt tccaacctga taccccattcc caaaagtagg agcttctctc   13620
tagtcatttt atcctctgag aaactgtcag ttctcctccc acaaggctcc cagacagcca   13680
```

```
cgggtgacca gggtctccaa tcactcctta agatgccttt gactggctgg gcgcagtgac   13740
tcatgactgt aatcctagca cttttgggtgg tcaacgtggg agggttgctt gcaacatggc   13800
aagaccccgt ctctacaaaa aaagtaaaat aataaaagta aagatgcctc tgaggggatc   13860
tgtttggttc atattaaaag agactgaatt catccattca acaatagcga gtttctccca   13920
ggtgtgaggt accctgctag ctaactggtg tgcacaaatc aagaaaacct caatgcaccg   13980
tcactccata acttctcgct tttgtttcag gtgagggctt ccacaactac caccactcct   14040
ttccctatga ctactctgcc agtgagtacc gctggcacat caacttcacc acattcttca   14100
ttgattgcat ggccgccctc ggtctggcct atgaccggaa gaaagtctcc aaggccgcca   14160
tcttggccag gattaaaaga accggagatg gaaactacaa gagtggctga gtttggggtc   14220
cctcaggttc ctttttcaaa aaccagccag gcagaggttt taatgtctgt ttattaacta   14280
ctgaataatg ctaccaggat gctaaagatg atgatgttaa cccattccag tacagtattc   14340
ttttaaaatt caaaagtatt gaaagccaac aactctgcct ttatgatgct aagctgatat   14400
tatttcttct cttatcctct ctctcttcta ggcccattgt cctccttttc actttattgc   14460
tatcgccctc cttcccctta ttgcctccca ggcaagcagc tggtcagtct ttgctcagtg   14520
tccagcttcc aaagcctaga caaccttcct gtagcctaaa acgaatggtc tttgctccag   14580
ataactctct ttccttgagc tgttgtgagc tttgaagtag gtggcttgag ctagagataa   14640
aacagaatct tctgggtagt cccctgttga ttatcttcag cccaggcttt gctagatgg   14700 aatggaaaag caacttcatt tgacacaaag cttctaaagc aggtaaattg tcggggaga   14760 gagttagcat gtatgaatgt aaggatgagg gaagcgaagc aagaggaacc tctcgccatg   14820
atcagacata cagctgccta cctaatgagg acttcaagcc ccaccacata gcatgcttcc   14880
tttctctcct ggctcggggt aaaaagtggc tgcggtgttt ggcaatgcta attcaatgcc   14940
gcaacatata gttgaggccg aggataaaga aaagacattt taagtttgta gtaaaagtgg   15000
tctctgctgg ggaagggttt tctttcttt ttttctttaa taacaaggag atttcttagt   15060
tcatatatca agaagtcttg aagttgggtg tttccagaat tggtaaaaac agcagctcat   15120
agaattttga gtattccatg agctgctcat tacagttctt tcctctttct gctctgccat   15180
cttcaggata ttggttcttc ccctcatagt aataagatgg ctgtggcatt tccaaacatc   15240
caaaaaaagg gaaggattta aggaggtgaa gtcgggtcaa aaataaaata tatatacata   15300
tatacattgc ttagaacgtt aaactattag agtatttccc ttccaaagag ggatgtttgg   15360
aaaaaactct gaaggagagg aggaattagt tgggatgcca atttcctctc cactgctgga   15420
catgagatgg agaggctgag ggacaggatc tataggcagc ttctaagagc gaacttcaca   15480
taggaaggga tctgagaaca cgttgccagg ggcttgagaa ggttactgag tgagttattg   15540
ggagtcttaa taaataaac tagatattag gtccattcat taattagttc cagtttctcc   15600
ttgaaatgag taaaaactag aaggcttctc tccacagtgt tgtgcccctt cactcatttt   15660
tttttgagga aagggggtc tctgttaaca tctagcctaa agtatacaac tgcctggggg   15720
gcagggttag gaatctcttc actaccctga ttcttgattc ctggctctac cctgtctgtc   15780
ccttttcttt gaccagatct ttctcttccc tgaacgtttt cttctttccc tggacaggca   15840
gcctcctttg tgtgtattca gaggcagtga tgacttgctg tccaggcagc tccctcctgc   15900
acacagaatg ctcagggtca ctgaaccact gcttctcttt tgaaagtaga gctagctgcc   15960
actttcacgt ggcctccgca gtgtctccac ctacacccct gtgctcccct gccacactga   16020
tggctcaaga caaggctggc aaaccctccc agaaacatct ctggcccaga aagcctctct   16080
```

```
ctccctccct ctctcatgag gcacagccaa gccaagcgct catgttgagc cagtgggcca    16140
gccacagagc aaaagagggt ttattttcag tccctctct ctgggtcaga accagagggc    16200
atgctgaatg ccccctgctt acttggtgag ggtgccccgc ctgagtcagt gctctcagct    16260
ggcagtgcaa tgcttgtaga agtaggagga aacagttctc actgggaaga agcaagggca    16320
agaacccaag tgcctcacct cgaaaggagg ccctgttccc tggagtcagg gtgaactgca    16380
aagctttggc tgagacctgg gatttgagat accacaaacc ctgctgaaca cagtgtctgt    16440
tcagcaaact aaccagcatt ccctacagcc tagggcagac aatagtatag aagtctggaa    16500
aaaaacaaaa acagaatttg agaaccttgg accactcctg tccctgtagc tcagtcatca    16560
aagcagaagt ctggctttgc tctattaaga ttgaaaatgt acactaccaa acactcagtc    16620
cactgttgag ccccagtgct ggaagggagg aaggcctttc ttctgtgtta attgcgtaga    16680
ggctacaggg gttagcctgg actaaaggca tccttgtctt ttgagctatt cacctcagta    16740
gaaaggatc taagggaaga tcactgtagt ttagttctgt tgacctgtgc acctaccct     16800
tggaaatgtc tgctggtatt tctaattcca caggtcatca gatgcctgct tgataatata    16860
taaacaataa aaacaacttt cacttcttcc tattgtaatc gtgtgccatg gatctgatct    16920
gtaccatgac cctacataag gctggatggc acctcaggct gagggcccca atgtatgtgt    16980
ggctgtgggt gtgggtggga gtgtgtctgc tgagtaagga acacgatttt caagattcta    17040
aagctcaatt caagtgacac attaatgata aactcagatc tgatcaagag tccggatttc    17100
taacagtcct tgctttgggg ggtgtgctga caacttagct caggtgcctt acatcttttc    17160
taatcacagt gttgcatatg agcctgccct cactccctct gcagaatccc tttgcacctg    17220
agaccctact gaagtggctg gtagaaaaag gggcctgagt ggaggattat cagtatcacg    17280
atttgcagga ttcccttctg ggcttcattc tggaaacttt tgttagggct gcttttctta    17340
agtgcccaca tttgatggag ggtggaaata atttgaatgt atttgattta aagttttttt    17400
tttttttttt gggttaaaag atggttgtag catttaaaat ggaaaatttt ctccttggtt    17460
tgctagtatc ttgggtgtat tctctgtaag tgtagctcaa ataggtcatc atgaaaggtt    17520
aaaaaagcga ggtggccatg ttatgctggt ggttaaggcc agggcctctc caaccactgt    17580
gccactgact tgctgtgtga ccctgggcaa gtcacttaac tataaggtgc ctcagttttc    17640
cttctgttaa aatggggata ataatactga cctacctcaa agggcagttt tgaggcatga    17700
ctaatgcttt ttagaaagca ttttgggatc cttcagcaca ggaattctca agacctgagt    17760
atttttata ataggaatgt ccaccatgaa cttgatacgt ccgtgtgtcc cagatgctgt    17820
cattagtcta tatggttctc caagaaactg aatgaatcca ttggagaagc ggtggataac    17880
tagccagaca aaatttgaga atacataaac aacgcattgc cacggaaaca tacagaggat    17940
gccttttctg tgattgggtg ggatttttc cctttttatg tgggatatag tagttacttg    18000
tgacaagaat aattttggaa taatttctat taatatcaac tctgaagcta attgtactaa    18060
tctgagattg tgtttgttca taataaaagt gaagtgaatc tgattgcact gggtctggga    18120
gtttcttttg gctgtgattc aaagtcttgg gatttgtctc tggctcatat ctatgtctgt    18180
accctttaaga gtataaaaga agtagaagtt acaatggttg actcataccc cattaacctg    18240
ccctgctgtc ctaaaggtaa ctttaggtta aactctggga cgcaggaagc caggagtctg    18300
ctgccattaa atcaaacaca ttaacaccag ctggcaactt ggccctgggg aagtgccagg    18360
gttctcgggt gtgtcacgtg gtcggtcaca tagacctaag ataaagacac tgggagagga    18420
aaagaccagc aggagaagcg ctccctggga aagcagtttt ttgctcttgc ccaggctgga    18480
```

-continued gtgcaatggt gtgatctggg ctcactgc                                      18508

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gtgcgcgcga gcccgaaatc                                                  20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ccgtgtccgg tatttcctca                                                  20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ggcaacgggt gaccgtgtcc                                                  20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
atttaaaggc tagagctggc                                                  20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cgagccggga atttaaaggc                                                  20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gaggctccgg agcggagttc                                                  20

<210> SEQ ID NO 88
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 88
ttggctctcg gatgccggga                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gtgggccggc atcttggctc                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tcctgcagca agtgggccgg                                                    20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
agctagagat atcgtcctgc                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ccatacaggg ctcccaagtg                                                    20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gtagaacttg caggtaggaa                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gctgttatgc ccagggcact                                                    20
```

```
<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
agacatcatt ctggaatgcc                                        20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
ctgaaaactt gtggtgggca                                        20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gtgtttctga aaacttgtgg                                        20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
aagtctagcg tactcccctt                                        20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
tttgtagtac ctcctctgga                                        20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
cataaggacg atatccgaag                                        20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
``` cccaaaactca gccactcttg                                      20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
aaacctctgc ctggctggtt                                       20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gtagcattat tcagtagtta                                       20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
tactggaatg ggttaacatc                                       20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
tcagcttagc atcataaagg                                       20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
agactgacca gctgcttgcc                                       20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
gctggacact gagcaaagac                                       20

<210> SEQ ID NO 108
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 108
tttggaagct ggacactgag                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
tctggagcaa agaccattcg                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
cttcaaagct cacaacagct                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
ccacctactt caaagctcac                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
tcaagccacc tacttcaaag                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ctctagctca agccacctac                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
tgtgtcaaat gaagttgctt                                              20
```

```
<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
cccgacaatt tacctgcttt                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ttacattcat acatgctaac                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
tgtctgatca tggcgagagg                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
aaggaagcat gctatgtggt                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
ggagagaaag gaagcatgct                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
aactatatgt tgcggcattg                                               20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
```
tagatgttaa cagagacccc					20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
aatcagggta gtgaagagat					20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
gggtagagcc aggaatcaag					20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
agcagtggtt cagtgaccct					20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tactttcaaa agagaagcag					20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
cgtgaaagtg gcagctagct					20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ccttgtcttg agccatcagt					20

<210> SEQ ID NO 128
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 128
ggtttgccag ccttgtcttg                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
cactggctca acatgagcgc                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tgctctgtgg ctggcccact                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
aataaaccct cttttgctct                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gactgaaaat aaaccctctt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
agagcactga ctcaggcggg                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
ttgcactgcc agctgagagc                                               20
```

```
<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tacttctaca agcattgcac                                                    20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
actgtttcct cctacttcta                                                    20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
cttgcccttg cttcttccca                                                    20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
tttcgaggtg aggcacttgg                                                    20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tcagccaaag ctttgcagtt                                                    20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
ttctgctttg atgactgagc                                                    20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
```
atcctcggcc tcaactatat                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tccttgttat taaagaaaaa                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
ctaagaaatc tccttgttat                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
cttcttgata tatgaactaa                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
acttcaagac ttcttgatat                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
aaattccatg agctgctgtt                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
gaactgtaat gagcagctca                                              20

<210> SEQ ID NO 148
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 148
tgaagatggc agagcagaaa                                               20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
tggaaatgcc acagccatct                                               20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
cgacttcacc tccttaaatc                                               20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gcaatgtata tatgtatata                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ccagcagtgg agaggaaatt                                               20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
cagcctctcc atctcatgtc                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
ctatgtgaag ttcgctctta                                               20
```

```
<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
cgtgttctca gatcccttcc                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
aactaattaa tgaatggacc                                              20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
ttactcattt caaggagaaa                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gaagccttct agtttttact                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
cactgtggag agaagccttc                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gcacaacact gtggagagaa                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
```
aatcttaata gagcaaagcc                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
gactgagtgt ttggtagtgt                                               20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
agcctctacg caattaacac                                               20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
ctgaggtgaa tagctcaaaa                                               20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165 cctttctac tgaggtgaat                                                20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
tagaaatacc agcagacatt                                               20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
gcacacgatt acaataggaa                                               20

<210> SEQ ID NO 168
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 168
tccatggcac acgattacaa                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
tcagatccat ggcacacgat                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
aggtgccatc cagccttatg                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
gccctcagcc tgaggtgcca                                               20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
agctttagaa tcttgaaaat                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
aatgtgtcac ttgaattgag                                               20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
ctgttagaaa tccggactct                                               20
```

```
<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ccaaagcagg gactgttaga                                                   20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
caacactgtg attagaaaag                                                   20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
cttcagtagg gtctcaggtg                                                   20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
ctaccagcca cttcagtagg                                                   20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
actcaggccc cttttctac                                                    20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
gatactgata atcctccact                                                   20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
```
aatcctgcaa atcgtgatac					20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
agcagcccta acaaaagttt					20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
aaattttcca ttttaaatgc					20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
cacttacaga gaatacaccc					20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
gagctacact tacagagaat					20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
aacatggcca cctcgctttt					20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
gccttaacca ccagcataac					20

<210> SEQ ID NO 188
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 188
aggccctggc cttaaccacc                                              20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
tggagaggcc ctggccttaa                                              20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
tcatgcctca aaactgccct                                              20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
ctaaaaagca ttagtcatgc                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
agaattcctg tgctgaagga                                              20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
ggtcttgaga attcctgtgc                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
actcaggtct tgagaattcc                                              20
```

```
<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
ggacattcct attataaaaa                                       20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
acacggacgt atcaagttca                                       20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
cctctgtatg tttccgtggc                                       20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
tgcgaggagt tgactggcgc                                       20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
ggcaaagtgc gaggagttga                                       20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
ggaaactcac atcgtcctgc                                       20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
```
ggctgcttac cccaaagcca                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
ctcagttgca tttcactgta                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
gtgggaagag aagatgtcca                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
gccttctcta aggttttaag                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
tagaataccc ctgccaggag                                              20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
aacttcttac ctggaatgcc                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
ccttgcaaaa gagctcatac                                              20

<210> SEQ ID NO 208
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 208
cttcactcac ctcctctgga                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
tttgcactgt ctctccccac                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
tcagtggttt cttacacttg                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
tttgtagtac ctacattgac                                              20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
gctgacttac ccacagctcc                                              20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
tactgccccc taattttata                                              20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
ccatttgcga tacaggaaac                                              20
```

```
<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
aagccctcac ctgaaacaaa                                              20

<210> SEQ ID NO 216
<211> LENGTH: 912
<212> TYPE: DNA
<213> ORGANISM: M. musculus

<400> SEQUENCE: 216
tcccagtctc ccggggtttc tctttgctgg tgcctggaag tgggggtaga tgtgaagtta    60
gaccgagttg tgagtggcgg tagccagtgt cttcctcact tctttcgatg cgatttcccc   120
agtgaaccat ttgctaagcg ccagaccaaa gtcctaggct tgcacacaat tcctacttgg   180
aatcacgtta tcctgctctt aaagaaaagt cacccatcag cccacagcaa agaggataag   240
gagaaaaaga ggggaggaga gacggagaag ctagaggcag agggaacagc agattgcgcc   300
tagccaatgg aaaaggcagg acaaggtggc accaaattct ctttggccaa tgacaagacg   360
ggcttcacag gaggcacatt agcatttatc cccaggcagg gggttggagc agcgcgccct   420
gttgatgcct tcagcatccc ggcgcctcca aggtctactc tggaatctac ttggctttct   480
ttcccgttct tggtcccgcc ctctctctct ccctccctcc ctccctccct tcctccctcc   540
ctccctccct ccctccctcc ctcacctcca cgcctggctt ccttggctag ctatctctgc   600
gctctttacc ctttgctggc agccgataaa aggggggctga ggaaatactg aacacggtca  660
tcccatcgcc tgctctaccc tttaaaatcc cagcccagga gatctgtgca cagccagacc   720
gggctgaaca cccatcccga gagtcaggag ggcaggtttc caagcgcagt ccgccactc    780 gcctacacca acgggctccg gaaccgaagt ccacgctcga tctcagcact gggaaagtga   840
ggcgagcaac tgactatcat catgccggcc cacatgctcc aagaggtgag cttccagaag   900
cggccctcgc tc                                                      912

<210> SEQ ID NO 217
<211> LENGTH: 288
<212> TYPE: DNA
<213> ORGANISM: M. musculus

<400> SEQUENCE: 217
ttgcagatct ccagttctta cacgaccacc accaccatca ctgcacctcc ctccggaaat    60
gaacgagaga aggtgaagac agtgccctc cacctggaag aagacatccg tcctgaaatg    120
aaagaagata ttcacgaccc cacctatcag gatgaggagg accccccgcc caagctggag   180
tacgtctgga ggaacatcat tctcatggtc ctgctgcact gggaggcct gtacgggatc    240 atactggttc cctcctgcaa gctctacact gccctcttcg gtgagcag                288

<210> SEQ ID NO 218
<211> LENGTH: 144
<212> TYPE: DNA
<213> ORGANISM: M. musculus

<400> SEQUENCE: 218
ttgcagggat tttctactac atgaccagcg ctctgggcat cacagccggg gctcatcgcc    60
tctggagcca cagaacttac aaggctcggc tgcccctgcg gatcttccta atcattgcca   120
```

| | |
|---|---|
| acaccatggc gttccagtaa gaag | 144 |

<210> SEQ ID NO 219
<211> LENGTH: 221
<212> TYPE: DNA
<213> ORGANISM: M. musculus

<400> SEQUENCE: 219

| | |
|---|---|
| ttccagaaat gacgtgtacg actgggcccg agatcaccgc gcccaccaca agttctcaga | 60 |
| aacacacgcc gaccctcaca attcccgccg tggcttcttc ttctctcacg tgggttggct | 120 |
| gcttgtgcgc aaacacccgg ctgtcaaaga aagggcggaa aaactggaca tgtctgacct | 180 |
| gaaagccgag aagctggtga tgttccagag gaggtaaggg a | 221 |

<210> SEQ ID NO 220
<211> LENGTH: 247
<212> TYPE: DNA
<213> ORGANISM: M. musculus

<400> SEQUENCE: 220

| | |
|---|---|
| atgtaggtac tacaagcccg gcctcctgct gatgtgcttc atcctgccca cgctggtgcc | 60 |
| ctggtactgc tggggcgaga cttttgtaaa cagcctgttc gttagcacct tcttgcgata | 120 |
| cactctggtg ctcaacgcca cctggctggt gaacagtgcc gcgcatctct atggatatcg | 180 |
| cccctacgac aagaacattc aatcccggga gaatatcctg gtttccctgg gtgccgtggg | 240 |
| taagtca | 247 |

<210> SEQ ID NO 221
<211> LENGTH: 3660
<212> TYPE: DNA
<213> ORGANISM: M. musculus

<400> SEQUENCE: 221

| | |
|---|---|
| ttgcaggcga gggcttccac aactaccacc acaccttccc cttcgactac tctgccagtg | 60 |
| agtaccgctg gcacatcaac ttccaccacgt tcttcatcga ctgcatggct gccctgggcc | 120 |
| tggcttacga ccggaagaaa gtttctaagg ctactgtctt agccaggatt aagagaactg | 180 |
| gagacgggag tcacaagagt agctgagctt tgggcttctg agttcctgtt tcaaacgttt | 240 |
| tctggcagag atttaatatt ctgttgatta actaacaact ggatattgct atcggggtgt | 300 |
| taatgatgca tttaacctat tccggtacag tattcttata aaatgagaaa gctttgatca | 360 |
| cgttttgagg taataaatat tttatttagc taggattaac catgccacaa gacattatat | 420 |
| atttctaagc acatgata aatgcatata caattttgca caacagcttt aaataataac | 480 |
| aataaatttg aacattctat acagagagga tcaaagccaa ggaacatgct gttttgatgc | 540 |
| tagggtgagc atggtgctca gtccctgttt gtttgcatgg tgtccagctt tgtttcttct | 600 |
| ctgtcatcac caccttcagg caaatagttg accaaccact ggcctgtgtc tgtccaccct | 660 |
| ccaaagccca ggccacctttt ctgtttttctg aaatactgat ccttcctcct gaatacatcc | 720 |
| ctccttgttc ctagcttcaa gactgctgcc tcaaataggg atagcaaag tccccgctgc | 780 |
| aggttgtgct agatgggatg gagaaattat cttcatttga tacagagcaa gtagattgtc | 840 |
| tcgagagaaa agttagcatg cgtggtatga tttgtaagta aagatggaag agagagagag | 900 |
| agagagagag agagagagag agagagagag agaggtagcc atatctaaca gcctacttac | 960 |
| caaagacccc aggcctctct gcttggcatg cctcctttct gtccatcctc tgaacccag | 1020 |
| agattagtga gatttgaata attaaatcat tttcagagtg aaggggtta atgcagggtc | 1080 |

```
tgtgctaggg gagggtttta gcttttggta actgaagatt ttttcatgga aaaagtcttc   1140
gtgttcaatg tgcctagaac tgataactaa acagctgaca tttgtcgggg acagatatgg   1200
tgtgaaacta tgaaaatata agcaaaatct tcacttggaa catgaaacta tttcacttag   1260
aaaataatcg aaggacccga ggtgttgcct gggttgccag tttctttcgt ggctgggcag   1320
gaactagtga ggttgagggg cagtgtctgt aagtagctgc taagaggtgc atttccagat   1380
gaagcccttg gggaacatct gccagggatc cgcatggtgt tggctccatc cattgcttta   1440
gtttcctcct tggattgtgt agaaacttgg cttcccatgg ttttgaacct tccatgcctt   1500
ctttgctttg tggccaccca gcctgcctag tgctgcctag gaagctctta cccacctgat   1560
ttcttctgac atttctttct ttggcctttt tttctttctc cggacatgca gctagttgcc   1620
tgagtgtatc aagagcaccc aggacttgct gctgtccagg cctgttcctc ccccagtatc   1680
cgtgggtgtg gaagagctgt gtagcttcag gaagcagagc caggtgccac ctttctgtgg   1740
cttccagatc ctccctacct ccaactcatg tgcctctgtc acagtgattt caggaaagct   1800
tggtagaccc tctagcaaca tctcggttca gaaagtctct ctggtttgtg agttaacagc   1860
tcagctaagt gctgttttgt ctcagtgagt taaccactga atgcgagggt tggttgttga   1920
tctgtctcgg tgtgtgtcgg agtagacagc atatgcactt ctccctgtgc gctttgcaag   1980
gtaatgtggc tttggctgat ccatgcaggc aggtagtggt acagtgctgc tgaaaggaag   2040
aagttcccca ttttatctgt taaaacacca gagacatggg caagtgctaa tggacctcac   2100
ttcaggaaga gggtctgctt cctgaagcca gtgtgtgatg aaaagtgact gagacctgat   2160
atctaaggtg agacctgata cctaacactc tgtcacacag tccagggcca acagtgctat   2220
aggaaagtct agaagaaaac atcacatcag tattttagaa ccatcaacca tctcttgtcc   2280
ctatagccca atccagaggc ctggtttta gaactggctg tgtaaggtgc caaacactca   2340
gttcacttgt agaatcagag cctttttcc cccctatgtt aattgaacac gcgctctgag   2400
ctgttttgtt gaagtagaaa atctcataga aaaatcactg tagatctact gacctatagc   2460
cctctggaaa tgcctttgag atggttttac ttttctaggt catagatgcc tgattataaa   2520
gatgaacaat aaaatcagct ttctttcttt ctcttctgat cttattcccc agatctgatt   2580
caggccatgt tccaaagcaa ggctacattg aggtcctggt gtctttaagt aaaggacatc   2640
tttcagatcc tctcaaagaa ggatttataa cagtttccag atgaatgtac taatagcttt   2700
gggtgcctta tctctttcct aatctgtagt gcctgtgagc tcagtctcac tccttccctt   2760
agcccggaga cccttagat cgagtgggaa tagtcaagag gctggctgga gagtcatcag   2820
tacattggtt tgcagaaatc ttttacaggc tacattttgg aatttttttt ttttagtaa   2880
gtgatcaaat ttggtgggaa gtaattcgag tgtattcgat tgtattgtcg tcctcgttat   2940
cattgtcaaa catgttatag acggcagttg gcactgggc tgctaatctc tgggtgtagt   3000
ctctgaaact gtagctccag tgaggtggtg tgaaaggtta gcaaagccac catctgctgg   3060
tgctccagcc aaggtgcctc ttagccactg aattgctatg ttatcctttc tcttgtaaca   3120
aacccacccc agagataaag cctttaatca acccaagaaa ctcctgggct aagtatctga   3180
cagtctcaca tctcaacagt gtgaattaag tgtccatagc atcagctcag gaggacactc   3240
tgggagagtg ctgacaaaaa agggttatta atactgacct actacttcaa gggcagttct   3300
gaggtgatta gagcttttt taaaaaccaa gtatttgggg atcctcagca gaggtattca   3360
tacagactcc caaagaacta tatatgttcc tgagaccatc gtttagtcta cattgctctt   3420
cccagagact gacagatatg accagtcaaa gtgcaagact acctacccac tgccatgaaa   3480
```

-continued

```
accattgcag gaaacctttc ccttcctgaa tgagattttt ttttttccctt tttatgtggg   3540 gtaattattt gtgacccaag tgtaatttgg atgatttcca ttaatatcaa ctcttgaagc   3600
ctacttgtac tgattgagat tgtatttgtt cctaataaaa gtggatctgg ttgtactgtc   3660
```

<210> SEQ ID NO 222  
<211> LENGTH: 5383  
<212> TYPE: DNA  
<213> ORGANISM: M. musculus  
<220> FEATURE:  
<221> NAME/KEY: CDS  
<222> LOCATION: (862)...(1929)  
<223> OTHER INFORMATION: Antisense Oligonucleotide

<400> SEQUENCE: 222

```
tcccagtctc ccggggtttc tctttgctgg tgcctggaag tgggggtaga tgtgaagtta     60
gaccgagttg tgagtggcgg tagccagtgt cttcctcact tctttcgatg cgatttcccc    120
agtgaaccat ttgctaagcg ccagaccaaa gtcctaggct tgcacacaat tcctacttgg    180
aatcacgtta tcctgctctt aaagaaaagt cacccatcag cccacagcaa agaggataag    240
gagaaaaaga ggggaggaga gacggagaag ctagaggcag agggaacagc agattgcgcc    300
tagccaatgg aaaaggcagg acaaggtggc accaaattct ctttggccaa tgacaagacg    360
ggcttcacag gaggcacatt agcatttatc cccaggcagg gggttggagc agcgcgccct    420
gttgatgcct tcagcatccc ggcgcctcca aggtctactc tggaatctac ttggcttttct   480 ttccgttct tggtcccgcc ctctctctct ccctccctcc ctccctccct tcctccctcc    540
ctccctccct ccctccctcc ctcacctcca cgcctggctt ccttggctag ctatctctgc    600
gctctttacc ctttgctggc agccgataaa agggggctga ggaaatactg aacacggtca    660
tcccatcgcc tgctctaccc tttaaaatcc cagcccagga gatctgtgca cagccagacc    720
gggctgaaca cccatcccga gagtcaggag ggcaggtttc caagcgcagt tccgccactc    780
gcctacacca acgggctccg gaaccgaagt ccacgctcga tctcagcact gggaaagtga    840
```

```
ggcgagcaac tgactatcat c atg ccg gcc cac atg ctc caa gag atc tcc    891
                        Met Pro Ala His Met Leu Gln Glu Ile Ser
                         1               5                  10 agt tct tac acg acc acc acc atc act gca cct ccc tcc gga aat         939
Ser Ser Tyr Thr Thr Thr Thr Ile Thr Ala Pro Pro Ser Gly Asn
           15                  20                  25 gaa cga gag aag gtg aag aca gtg ccc ctc cac ctg gaa gaa gac atc     987
Glu Arg Glu Lys Val Lys Thr Val Pro Leu His Leu Glu Glu Asp Ile
        30                  35                  40 cgt cct gaa atg aaa gaa gat att cac gac ccc acc tat cag gat gag    1035
Arg Pro Glu Met Lys Glu Asp Ile His Asp Pro Thr Tyr Gln Asp Glu
    45                  50                  55 gag gga ccc ccg ccc aag ctg gag tac gtc tgg agg aac atc att ctc    1083
Glu Gly Pro Pro Pro Lys Leu Glu Tyr Val Trp Arg Asn Ile Ile Leu
60                  65                  70 atg gtc ctg ctg cac ttg gga ggc ctg tac ggg atc ata ctg gtt ccc    1131
Met Val Leu Leu His Leu Gly Gly Leu Tyr Gly Ile Ile Leu Val Pro
 75                  80                  85                  90 tcc tgc aag ctc tac act gcc ctc ttc ggg att ttc tac tac atg acc    1179
Ser Cys Lys Leu Tyr Thr Ala Leu Phe Gly Ile Phe Tyr Tyr Met Thr
                95                 100                 105 agc gct ctg ggc atc aca gcc ggg gct cat cgc ctc tgg agc cac aga    1227
Ser Ala Leu Gly Ile Thr Ala Gly Ala His Arg Leu Trp Ser His Arg
            110                 115                 120 act tac aag gct cgg ctg ccc ctg cgg atc ttc cta atc att gcc aac    1275
```

```
        Thr Tyr Lys Ala Arg Leu Pro Leu Arg Ile Phe Leu Ile Ile Ala Asn
                125                 130                 135 acc atg gcg ttc caa aat gac gtg tac gac tgg gcc cga gat cac cgc        1323
Thr Met Ala Phe Gln Asn Asp Val Tyr Asp Trp Ala Arg Asp His Arg
    140                 145                 150 gcc cac cac aag ttc tca gaa aca cac gcc gac cct cac aat tcc cgc        1371
Ala His His Lys Phe Ser Glu Thr His Ala Asp Pro His Asn Ser Arg
155                 160                 165                 170 cgt ggc ttc ttc ttc tct cac gtg ggt tgg ctg ctt gtg cgc aaa cac        1419
Arg Gly Phe Phe Phe Ser His Val Gly Trp Leu Leu Val Arg Lys His
                175                 180                 185 ccg gct gtc aaa gag aag gga gga aaa ctg gac atg tct gac ctg aaa        1467
Pro Ala Val Lys Glu Lys Gly Gly Lys Leu Asp Met Ser Asp Leu Lys
            190                 195                 200 gcc gag aag ctg gtg atg ttc cag agg agg tac tac aag ccc ggc ctc        1515
Ala Glu Lys Leu Val Met Phe Gln Arg Arg Tyr Tyr Lys Pro Gly Leu
            205                 210                 215 ctg ctg atg tgc ttc atc ctg ccc acg ctg gtg ccc tgg tac tgc tgg        1563
Leu Leu Met Cys Phe Ile Leu Pro Thr Leu Val Pro Trp Tyr Cys Trp
        220                 225                 230 ggc gag act ttt gta aac agc ctg ttc gtt agc acc ttc ttg cga tac        1611
Gly Glu Thr Phe Val Asn Ser Leu Phe Val Ser Thr Phe Leu Arg Tyr
235                 240                 245                 250 act ctg gtg ctc aac gcc acc tgg ctg gtg aac agt gcc gcg cat ctc        1659
Thr Leu Val Leu Asn Ala Thr Trp Leu Val Asn Ser Ala Ala His Leu
                255                 260                 265 tat gga tat cgc ccc tac gac aag aac att caa tcc cgg gag aat atc        1707
Tyr Gly Tyr Arg Pro Tyr Asp Lys Asn Ile Gln Ser Arg Glu Asn Ile
                270                 275                 280 ctg gtt tcc ctg ggt gcc gtg ggc gag ggc ttc cac aac tac cac cac        1755
Leu Val Ser Leu Gly Ala Val Gly Glu Gly Phe His Asn Tyr His His
            285                 290                 295 acc ttc ccc ttc gac tac tct gcc agt gag tac cgc tgg cac atc aac        1803
Thr Phe Pro Phe Asp Tyr Ser Ala Ser Glu Tyr Arg Trp His Ile Asn
        300                 305                 310 ttc acc acg ttc ttc atc gac tgc atg gct gcc ctg ggc ctg gct tac        1851
Phe Thr Thr Phe Phe Ile Asp Cys Met Ala Ala Leu Gly Leu Ala Tyr
315                 320                 325                 330 gac cgg aag aaa gtt tct aag gct act gtc tta gcc agg att aag aga        1899
Asp Arg Lys Lys Val Ser Lys Ala Thr Val Leu Ala Arg Ile Lys Arg
                335                 340                 345 act gga gac ggg agt cac aag agt agc tga gctttgggct tctgagttcc          1949
Thr Gly Asp Gly Ser His Lys Ser Ser *
            350                 355 tgtttcaaac gttttctggc agagatttaa tattctgttg attaactaac aactggatat     2009
tgctatcggg gtgttaatga tgcatttaac ctattccggt acagtattct tataaaatga     2069
gaaagctttg atcacgtttt gaggtaataa atattttatt tagctaggat taaccatgcc     2129
acaagacatt atatatttct aagcacacat gataaatgca tatacaattt tgcacaacag     2189
ctttaaataa taacaataaa tttgaacatt ctatacagag aggatcaaag ccaaggaaca     2249
tgctgttttg atgctagggt gagcatggtg ctcagtccct gtttgtttgc atggtgtcca     2309
gctttgtttc ttctctgtca tcaccacctt caggcaaata gttgaccaac cactggcctg     2369
tgtctgtcca ccctccaaag cccaggccac ctttctgttt tctgaaatac tgatccttcc     2429
tcctgaatac atccctcctt gttcctagct tcaagactgc tgcctcaaat agggatagag     2489
caagtccccg ctgcaggttg tgctagatgg gatggagaaa ttatcttcat ttgatacaga     2549
gcaagtagat tgtctcgaga gaaaagttag catgcgtggt atgatttgta agtaaagatg     2609
```

```
gaagagagag agagagagag agagagagag agagagagag agagagaggt agccatatct    2669
aacagcctac ttaccaaaga ccccaggcct ctctgcttgg catgcctcct ttctgtccat    2729
cctctgaacc ccagagatta gtgagatttg aataattaaa tcattttcag agtgaagggg    2789
gttaatgcag ggtctgtgct aggggagggt tttagctttt ggtaactgaa gatttttca    2849 tggaaaaagt cttcgtgttc aatgtgccta gaactgataa ctaaacagct gacatttgtc    2909
ggggacagat atggtgtgaa actatgaaaa tataagcaaa atcttcactt ggaacatgaa    2969
actatttcac ttagaaaata atcgaaggac ccgaggtgtt gcctgggttg ccagtttctt    3029
tcgtggctgg gcaggaacta gtgaggttga ggggcagtgt ctgtaagtag ctgctaagag    3089
gtgcatttcc agatgaagcc cttggggaac atctgccagg gatccgcatg gtgttggctc    3149
catccattgc tttagtttcc tccttggatt gtgtagaaac ttggcttccc atggttttga    3209
accttccatg ccttctttgc tttgtggcca cccagcctgc ctagtgctgc ctaggaagct    3269
cttacccacc tgatttcttc tgacatttct ttctttggcc ttttttttctt tctccggaca    3329 tgcagctagt tgcctgagtg tatcaagagc acccaggact tgctgctgtc caggcctgtt    3389
cctcccccag tatccgtggg tgtggaagag ctgtgtagct tcaggaagca gagccaggtg    3449
ccacctttct gtggcttcca gatcctccct acctccaact catgtgcctc tgtcacagtg    3509
atttcaggaa agcttggtag accctctagc aacatctcgg ttcagaaagt ctctctggtt    3569
tgtgagttaa cagctcagct aagtgctgtt ttgtctcagt gagttaacca ctgaatgcga    3629
gggttggttg ttgatctgtc tcggtgtgtg tcggagtaga cagcatatgc acttctccct    3689
gtgcgctttg caaggtaatg tggctttggc tgatccatgc aggcaggtag tggtacagtg    3749
ctgctgaaag gaagaagttc cccattttat ctgttaaaac accagagaca tgggcaagtg    3809
ctaatggacc tcacttcagg aagagggtct gcttcctgaa gccagtgtgt gatgaaaagt    3869
gactgagacc tgatatctaa ggtgagacct gataccctaac actctgtcac acagtccagg    3929
gccaacagtg ctataggaaa gtctagaaga aaacatcaca tcagtatttt agaaccatca    3989
accatctctt gtccctatag cccaatccag aggcctggtt tttagaactg gctgtgtaag    4049
gtgccaaaca ctcagttcac ttgtagaatc agagccttttt ttccccccta tgttaattga    4109
acacgcgctc tgagctgttt tgttgaagta gaaaatctca tagaaaaatc actgtagatc    4169
tactgaccta tagccctctg gaaatgcctt tgagatggtt ttactttttct aggtcataga    4229 tgcctgatta taaagatgaa caataaaatc agctttcttt cttttctcttc tgatcttatt    4289 ccccagatct gattcaggcc atgttccaaa gcaaggctac attgaggtcc tggtgtcttt    4349
aagtaaagga catctttcag atcctctcaa agaaggattt ataacagttt ccagatgaat    4409
gtactaatag ctttgggtgc cttatctctt tcctaatctg tagtgcctgt gagctcagtc    4469
tcactccttc ccttagcccg gagacccctt gatcgagtg ggaatagtca gaggctggc     4529 tggagagtca tcagtacatt ggtttgcaga aatctttac aggctacatt ttggaatttt    4589 tttttttta gtaagtgatc aaatttggtg ggaagtaatt cgagtgtatt cgattgtatt    4649
gtcgtcctcg ttatcattgt caaacatgtt atagacggca gttggcactg ggctgctaa     4709 tctctgggtg tagtctctga aactgtagct ccagtgaggt ggtgtgaaag gttagcaaag    4769
ccaccatctg ctggtgctcc agccaaggtg cctcttagcc actgaattgc tatgttatcc    4829
tttctcttgt aacaaaccca ccccagagat aaagccttta atcaacccaa gaaactcctg    4889
ggctaagtat ctgacagtct cacatctcaa cagtgtgaat taagtgtcca tagcatcagc    4949
tcaggaggac actctgggag agtgctgaca aaaaggggtt attaatactg acctactact    5009
```

```
tcaagggcag ttctgaggtg attagagctt tttttaaaaa ccaagtattt ggggatcctc     5069
agcagaggta ttcatacaga ctcccaaaga actatatatg ttcctgagac catcgtttag     5129
tctacattgc tcttcccaga gactgacaga tatgaccagt caaagtgcaa gactacctac     5189
ccactgccat gaaaaccatt gcaggaaacc tttcccttcc tgaatgagat tttttttttc     5249
cctttttatg tggggtaatt atttgtgacc caagtgtaat ttggatgatt tccattaata     5309
tcaactcttg aagcctactt gtactgattg agattgtatt tgttcctaat aaaagtggat     5369
ctggttgtac tgtc                                                        5383
```

```
<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
agatctcttg gagcatgtgg                                                    20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
cttctctcgt tcatttccgg                                                    20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
cttctttcat ttcaggacgg                                                    20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
tccctcctca tcctgatagg                                                    20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
cctccagacg tactccagct                                                    20

<210> SEQ ID NO 228
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 228
aggaccatga gaatgatgtt                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
acaggcctcc caagtgcagc                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
ggaaccagta tgatcccgta                                              20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
agtagaaaat cccgaagagg                                              20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
cggctgtgat gcccagagcg                                              20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
gctccagagg cgatgagccc                                              20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
cgagccttgt aagttctgtg                                              20
```

```
<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
gcaatgatta ggaagatccg                                               20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
tacacgtcat tttggaacgc                                               20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
ggtgatctcg ggcccagtcg                                               20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
cgtgtgtttc tgagaacttg                                               20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
cggctttcag gtcagacatg                                               20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
ctggaacatc accagcttct                                               20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
```
agcacatcag caggaggccg                                           20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
tgaagcacat cagcaggagg                                           20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
gtctcgcccc agcagtacca                                           20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
gcaccagagt gtatcgcaag                                           20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
caccagccag gtggcgttga                                           20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
tagagatgcg cggcactgtt                                           20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
ttgaatgttc ttgtcgtagg                                           20

<210> SEQ ID NO 248
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 248
cctcgcccac ggcacccagg                                               20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
gtagttgtgg aagccctcgc                                               20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
gaaggtgtgg tggtagttgt                                               20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
gcggtactca ctggcagagt                                               20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
ggtgaagttg atgtgccagc                                               20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
tcctggctaa gacagtagcc                                               20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
cccgtctcca gttctcttaa                                               20
```

```
<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
ttgtgactcc cgtctccagt                                          20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
tcagctactc ttgtgactcc                                          20

<210> SEQ ID NO 257
<211> LENGTH: 21
<212> TYPE: DNA
<213> ORGANISM: Artificial Sequence
<220> FEATURE:
<223> OTHER INFORMATION: PCR Primer

<400> SEQUENCE: 257
acaccagaga catgggcaag t                                        21

<210> SEQ ID NO 258
<211> LENGTH: 22
<212> TYPE: DNA
<213> ORGANISM: Artificial Sequence
<220> FEATURE:
<223> OTHER INFORMATION: PCR Primer

<400> SEQUENCE: 258
catcacacac tggcttcagg aa                                       22

<210> SEQ ID NO 259
<211> LENGTH: 19
<212> TYPE: DNA
<213> ORGANISM: Artificial Sequence
<220> FEATURE:
<223> OTHER INFORMATION: PCR Probe

<400> SEQUENCE: 259
ctgaagtgag gtccattag                                           19

<210> SEQ ID NO 260
<211> LENGTH: 19
<212> TYPE: DNA
<213> ORGANISM: Artificial Sequence
<220> FEATURE:
<223> OTHER INFORMATION: PCR Primer

<400> SEQUENCE: 260
gaaggtgaag gtcggagtc                                           19

<210> SEQ ID NO 261
<211> LENGTH: 20
<212> TYPE: DNA
<213> ORGANISM: Artificial Sequence
<220> FEATURE:
<223> OTHER INFORMATION: PCR Primer

<400> SEQUENCE: 261
```

```
gaagatggtg atgggatttc                                              20

<210> SEQ ID NO 262
<211> LENGTH: 20
<212> TYPE: DNA
<213> ORGANISM: Artificial Sequence
<220> FEATURE:
<223> OTHER INFORMATION: PCR Probe

<400> SEQUENCE: 262
caagcttccc gttctcagcc                                              20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
ggaagctcac ctcttggagc                                              20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
ctgctcaccg aagagggcag                                              20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
gtagtagaaa atccctgcaa                                              20

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
tcccttacct cctctggaac                                              20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
tgacttaccc acggcaccca                                              20

<210> SEQ ID NO 268
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 268
gtggaagccc tcgcctgcaa                                                    20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
ctggctaccg ccactcacaa                                                    20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
aagcctagga ctttggtctg                                                    20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
gtgtgcaagc ctaggacttt                                                    20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272
taggaattgt gtgcaagcct                                                    20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273
atctgctgtt ccctctgcct                                                    20

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274
tccagagtag accttggagg                                                    20
```

```
<210> SEQ ID NO 275
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 275
ctagccaagg aagccaggcg                                                 20

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276
gcagagatag ctagccaagg                                                 20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277
ttttatcggc tgccagcaaa                                                 20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278
ggatgaccgt gttcagtatt                                                 20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279
tggctgtgca cagatctcct                                                 20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
tcagcccggt ctggctgtgc                                                 20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281
```
gcgcttggaa acctgccctc                                              20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282
tgtaggcgag tggcggaact                                              20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
gtggacttcg gttccggagc                                              20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
ttgctcgcct cactttccca                                              20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285
gtgggccggc atgatgatag                                              20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
gaactggaga tctcttggag                                              20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
tagaaaatcc cgaagagggc                                              20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288
ggtcatgtag tagaaaatcc                                              20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
gcgctggtca tgtagtagaa                                              20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290
ggattgaatg ttcttgtcgt                                              20

<210> SEQ ID NO 291
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 291
tcccgggatt gaatgttctt                                              20

<210> SEQ ID NO 292
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 292
gatattctcc cgggattgaa                                              20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293
gtagccttag aaactttctt                                              20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294
cccaaagctc agctactctt                                              20

```
<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295
aacaggaact cagaagccca                                               20

<210> SEQ ID NO 296
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 296
cagaatatta aatctctgcc                                               20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297
agttgttagt taatcaacag                                               20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
aattgtatat gcatttatca                                               20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
ctgtatagaa tgttcaaatt                                               20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
acagcatgtt ccttggcttt                                               20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301
```
tagcatcaaa acagcatgtt                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
accatgctca ccctagcatc                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
aaggatcagt atttcagaaa                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
tctctcgaga caatctactt                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
cttcagttac caaaagctaa                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
aaatgtcagc tgtttagtta                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
ggcaacccag gcaacacctc                                               20

<210> SEQ ID NO 308
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 308
gccacgaaag aaactggcaa                                                   20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
atgttcccca agggcttcat                                                   20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
tccctggcag atgttcccca                                                   20

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311
ctggctctgc ttcctgaagc                                                   20

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312
gctgagctgt taactcacaa                                                   20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
cacacaccga gacagatcaa                                                   20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314
caggaagcag accctcttcc                                                   20
```

```
<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315
aatactgatg tgatgttttc                                                20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316
atggttctaa aatactgatg                                                20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
actgagtgtt tggcacctta                                                20

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
ggctctgatt ctacaagtga                                                20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
tcaacaaaac agctcagagc                                                20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
gattttctac ttcaacaaaa                                                20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321
```
cttaaagaca ccaggacctc                                               20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
catctggaaa ctgttataaa                                               20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
ctaagggaag gagtgagact                                               20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
ttacttccca ccaaatttga                                               20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
tgacaatgat aacgaggacg                                               20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
cagatggtgg ctttgctaac                                               20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
ttgttacaag agaaaggata                                               20

<210> SEQ ID NO 328
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 328
tcagatactt agcccaggag                                               20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
tgttgagatg tgagactgtc                                               20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
cacctcagaa ctgcccttga                                               20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331
gctctaatca cctcagaact                                               20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
ggagtctgta tgaatacctc                                               20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
tctctgggaa gagcaatgta                                               20

<210> SEQ ID NO 334
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 334
gtaggtagtc ttgcactttg                                               20
```

```
<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
aggaagggaa aggtttcctg                                                    20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
tacacttggg tcacaaataa                                                    20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
aatcatccaa attacacttg                                                    20

<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338
cttcaagagt tgatattaat                                                    20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
atacaatctc aatcagtaca                                                    20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
cacttttatt aggaacaaat                                                    20

<210> SEQ ID NO 341
<211> LENGTH: 18
<212> TYPE: DNA
<213> ORGANISM: Artificial Sequence
<220> FEATURE:
<223> OTHER INFORMATION: PCR Primer

<400> SEQUENCE: 341
```

-continued ttccgccact cgcctaca                                                    18

<210> SEQ ID NO 342
<211> LENGTH: 21
<212> TYPE: DNA
<213> ORGANISM: Artificial Sequence
<220> FEATURE:
<223> OTHER INFORMATION: PCR Primer

<400> SEQUENCE: 342
ctttcccagt gctgagatcg a                                                21

<210> SEQ ID NO 343
<211> LENGTH: 20
<212> TYPE: DNA
<213> ORGANISM: Artificial Sequence
<220> FEATURE:
<223> OTHER INFORMATION: PCR Probe

<400> SEQUENCE: 343
caacgggctc cggaaccgaa                                                  20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344
gcttgcagga gggaaccagt                                                  20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
ctaggacttt ggtctggcgc                                                  20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346
gcgcaatctg ctgttccctc                                                  20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 347
agggcgcgct gctccaaccc                                                  20

<210> SEQ ID NO 348
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 348
aagaaagcca agtagattcc                                              20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349
gtgcacagat ctcctgggct                                              20

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350
ctgccctcct gactctcggg                                              20

<210> SEQ ID NO 351
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 351
agaactggag atctcttgga                                              20

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352
cctcctcatc ctgataggtg                                              20

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353
acgtactcca gcttgggcgg                                              20

<210> SEQ ID NO 354
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 354
atgttcctcc agacgtactc                                              20
```

```
<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355
gaatgatgtt cctccagacg                                              20

<210> SEQ ID NO 356
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 356
ccatgagaat gatgttcctc                                              20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357
tcccgtacag gcctcccaag                                              20

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358
tgtagagctt gcaggaggga                                              20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359
gccatggtgt tggcaatgat                                              20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360
tctgagaact tgtggtgggc                                              20

<210> SEQ ID NO 361
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 361
```
gtgtttctga gaacttgtgg                                               20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362
ggcgtgtgtt tctgagaact                                               20

<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363
aattgtgagg gtcggcgtgt                                               20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 364
ccacggcggg aattgtgagg                                               20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365
aagaagccac ggcgggaatt                                               20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366
agcagccaac ccacgtgaga                                               20

<210> SEQ ID NO 367
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 367
tgcgcacaag cagccaaccc                                               20

<210> SEQ ID NO 368
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 368
gtgtttgcgc acaagcagcc                                              20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369
acagccgggt gtttgcgcac                                              20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370
ctttgacagc cgggtgtttg                                              20

<210> SEQ ID NO 371
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 371
cttctctttg acagccgggt                                              20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372
ccgcccttct ctttgacagc                                              20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373
atgtccagtt ttccgccctt                                              20

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374
cagacatgtc cagttttccg                                              20
```

```
<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375
caggtcagac atgtccagtt                                               20

<210> SEQ ID NO 376
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 376
gctttcaggt cagacatgtc                                               20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377
tctcggcttt caggtcagac                                               20

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378
cagcttctcg gctttcaggt                                               20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379
atcaccagct tctcggcttt                                               20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 380
ggaacatcac cagcttctcg                                               20

<210> SEQ ID NO 381
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 381
```
ctcctctgga acatcaccag                                          20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382
ttgtagtacc tcctctggaa                                          20

<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383
aggatgaagc acatcagcag                                          20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 384
agcgtgggca ggatgaagca                                          20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385
gtaccagggc accagcgtgg                                          20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386
cagcagtacc agggcaccag                                          20

<210> SEQ ID NO 387
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387
cgccccagca gtaccagggc                                          20

<210> SEQ ID NO 388
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 388
gaaggtgcta acgaacaggc                                              20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389
ctgttcacca gccaggtggc                                              20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390
gcggcactgt tcaccagcca                                              20

<210> SEQ ID NO 391
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 391
accaggatat tctcccggga                                              20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392
tggtagttgt ggaagccctc                                              20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393
tactcactgg cagagtagtc                                              20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394
agcggtactc actggcagag                                              20
```

```
<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395
gtgccagcgg tactcactgg                                           20

<210> SEQ ID NO 396
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 396
ttgatgtgcc agcggtactc                                           20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397
gtggtgaagt tgatgtgcca                                           20

<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398
aagaacgtgg tgaagttgat                                           20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399
cagtagcctt agaaactttc                                           20

<210> SEQ ID NO 400
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 400
ccagttctct taatcctggc                                           20

<210> SEQ ID NO 401
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 401
```
ccgtctccag ttctcttaat         20

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402
taacaccccg atagcaatat         20

<210> SEQ ID NO 403
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 403
gagggtggac agacacaggc         20

<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 404
cttgaagcta ggaacaagga         20

<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405
tatggctacc tctctctctc         20

<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406
ttttcatagt ttcacaccat         20

<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407
tattttctaa gtgaaatagt         20

<210> SEQ ID NO 408
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 408
taggcagcac taggcaggct                                               20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409
aggaacaggc ctggacagca                                               20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410
gagggctata ggtcagtaga                                               20

<210> SEQ ID NO 411
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 411
aagacaccag gacctcaatg                                               20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412
ccaatgtact gatgactctc                                               20

<210> SEQ ID NO 413
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 413
tcacaccacc tcactggagc                                               20

<210> SEQ ID NO 414
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 414
agtaggtcag tattaataac                                               20
```

```
<210> SEQ ID NO 415
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 415
atctcattca ggaagggaaa                                                     20

<210> SEQ ID NO 416
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 416
aaattacact tgggtcacaa                                                     20

<210> SEQ ID NO 417
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 417
caatctcaat cagtacaagt                                                     20

<210> SEQ ID NO 418
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 418
ccttccctga aggttcctcc                                                     20

<210> SEQ ID NO 419
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 419
cgagaggcgg acgggaccg                                                      19

<210> SEQ ID NO 420
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: (1)...(19)
<223> OTHER INFORMATION: bases at these positions are RNA

<400> SEQUENCE: 420
cgagaggcgg acgggaccgt t                                                   21

<210> SEQ ID NO 421
<211> LENGTH: 21
<212> TYPE: DNA
<213> ORGANISM: Artificial Sequence
```

```
<220> FEATURE:
<223> OTHER INFORMATION: Antisense Oligonucleotide
<220> FEATURE:
<221> NAME/KEY: misc_feature
<222> LOCATION: (3)...(21)
<223> OTHER INFORMATION: bases at these positions are RNA

<400> SEQUENCE: 421
ttgcucuccg ccugcccugg c                                              21
```